(12) United States Patent
Jaworski et al.

(10) Patent No.: US 12,134,647 B2
(45) Date of Patent: Nov. 5, 2024

(54) BINDING MOLECULES

(71) Applicant: Immunocore Limited, Oxon (GB)

(72) Inventors: Jakub Jaworski, Oxon (GB); Kate Atkin, Oxon (GB); Arnaud Techine, Oxon (GB); Vijaykumar Karuppiah, Oxon (GB); Florence Schlosser, Oxon (GB); Ana Pereira Ribeiro, Oxon (GB); Chandramouli Chillakuri, Oxon (GB); Nathaniel Liddy, Oxon (GB); Andrew Creese, Oxon (GB); Martin Ebner, Oxon (GB)

(73) Assignee: IMMUNOCORE LIMITED, Oxon (GB)

( * ) Notice: Subject to any disclaimer, the term of this patent is extended or adjusted under 35 U.S.C. 154(b) by 0 days.

(21) Appl. No.: 18/405,910

(22) Filed: Jan. 5, 2024

(65) Prior Publication Data

US 2024/0228617 A1 Jul. 11, 2024

(30) Foreign Application Priority Data

Jan. 6, 2023 (GB) ..................... 2300227

(51) Int. Cl.
*C07K 16/00* (2006.01)
*A61P 35/00* (2006.01)
*C07K 16/28* (2006.01)

(52) U.S. Cl.
CPC .......... *C07K 16/2809* (2013.01); *A61P 35/00* (2018.01); *C07K 2317/31* (2013.01); *C07K 2317/52* (2013.01); *C07K 2317/565* (2013.01); *C07K 2317/567* (2013.01); *C07K 2317/622* (2013.01)

(58) Field of Classification Search
CPC ............ C07K 16/2809; C07K 2317/31; C07K 2317/52; C07K 2317/565; C07K 2317/567; C07K 2317/622
See application file for complete search history.

(56) References Cited

FOREIGN PATENT DOCUMENTS

| CN | 106699874 A | 5/2017 |
|---|---|---|
| CN | 106831978 A | 6/2017 |
| CN | 116715750 A | 9/2023 |
| WO | 1998/039482 A1 | 9/1998 |
| WO | 1999/018129 A1 | 4/1999 |
| WO | 2001/062908 A2 | 8/2001 |
| WO | 2003/020763 A2 | 3/2003 |
| WO | 2004/033685 A1 | 4/2004 |
| WO | 2010/133828 A1 | 11/2010 |
| WO | 2014/096803 A1 | 6/2014 |
| WO | 2015/136072 A1 | 9/2015 |
| WO | 2017/046198 A1 | 3/2017 |
| WO | 2017/046201 A1 | 3/2017 |
| WO | 2019/012138 A1 | 1/2019 |
| WO | 2019/012141 A1 | 1/2019 |
| WO | 2021/078774 A1 | 4/2021 |
| WO | 2021/150804 A1 | 7/2021 |
| WO | 2022/234116 A1 | 11/2022 |

OTHER PUBLICATIONS

Agirre et al., "The CCP4 suite: integrative software for macromolecular crystallography." Acta. Crystal. Sect. D, Struct. Biol. 79, 449-461 (2023).
Bossi et al., "Examining the presentation of tumor-associated antigens on peptide-pulsed T2 cells," Oncoimmunol. 1;2 (11) :e26840 (2013).
Boulter et al., "Stable, soluble T-cell receptor molecules for crystallization and therapeutics," Protein Eng. 16, 707-711 (2003).
Bragado et al., "Allelic polymorphism in the coding region of human TCR Cα gene and characterization of structural variability in the α chain constant domain," International Immunology 6(2):223-30 (1994).
Cameron et al., "Identification of a Titin-derived HLA-A1-presented peptide as a cross-reactive target for engineered MAGE A3-directed T cells," Sci Transl. Med. 5 (197): 197ra103 (2013).
Doolan et al., "Prevalence and prognostic and predictive relevance of PRAME in breast cancer," Breast Cancer Res Treat. 109(2):359-365 (2008).
Emsley et al., "Features and development of Coot," Acta Crystal. Sect D Biological Crystallogr. 66, 486-501 (2010).
Epel et al., "A functional recombinant single-chain T cell receptor fragment capable of selectively targeting antigen-presenting cells," Cancer Immunol Immunother 51(10):565-73 (2002).
Epping et al., "A Causal Role for the Human Tumor Antigen Preferentially Expressed Antigen of Melanoma in Cancer," Cancer Res. 66(22):10639-42 (2006).
Epping et al., "The Human Tumor Antigen PRAME Is a Dominant Repressor of Retinoic Acid Receptor Signaling," Cell 122(6):835-847 (2005).
Garboczi et al., "HLA-A2-peptide complexes: Refolding and crystallization of molecules expressed in *Escherichia coli* and complexed with single antigenic peptides," Proc. Natl. Acad. Sci. USA 89(8): 3429-3433 (1992).
Holler et al., "In vitro evolution of a T cell receptor with high affinity for peptide/MHC," Proc. Natl. Acad. Sci. U S A. 97(10):5387-92 (2000).
Hoo et al., "Characterization of a single-chain T-cell receptor expressed in *Escherichia coli*," Proc. Natl. Acad. Sci. U S A 89(10): 4759-4763 (1992).
Ikeda et al., "Characterization of an Antigen That Is Recognized on a Melanoma Showing Partial HLA Loss by CTL Expressing an NK Inhibitory Receptor," Immunity. 6(2):199-208 (1997).

(Continued)

*Primary Examiner* — Lei Yao
(74) *Attorney, Agent, or Firm* — MEDLER FERRO WOODHOUSE & MILLS PLLC

(57) ABSTRACT

The present invention relates to binding molecules that comprise T cell receptor (TCR) variable domains and which can bind to a PRAME peptide-HLA complex. In particular, the present invention relates to binding molecules that bind to PYLGQMINL (SEQ ID NO: 1) in complex with HLA-A24. The invention also relates to the use of such molecules for the treatment of malignant diseases.

22 Claims, 15 Drawing Sheets

Specification includes a Sequence Listing.

(56) References Cited

OTHER PUBLICATIONS

Kabsch, "XDS," Acta. Crystal. Sect D Biological Crystallogr. 66, 125-132 (2010).

Kovalevskiy et al., "Overview of refinement procedures within REFMAC5: utilizing data from different sources," Acta. Crystal. Sect. D, Struct. Biol. 74, 215-227 (2018).

Li et al., "Directed evolution of human T-cell receptors with picomolar affinities by phage display," Nat Biotechnol. 23(3):349-54 (2005).

Liddy et al., "Monoclonal TCR-redirected tumor cell killing," Nat Med. 18(6):980-7 (2012).

Lissin et al., "High-Affinity Monoclonal T-cell receptor (mTCR) Fusions," in Fusion Protein Technologies for Biophamaceuticals: Applications and Challenges (Book), Chapter 32 (2013).

Mareeva et al., "How a T Cell Receptor-like Antibody Recognizes Major Histocompatibility Complex-bound Peptide," JBC 283(43):29053-29059 (2008).

Matsushita et al., "Preferentially Expressed Antigen of Melanoma (PRAME) in the Development of Diagnostic and Therapeutic Methods for Hematological Malignancies," Leuk Lymphoma. 44(3):439-44 (2003).

McCoy et al., "Phaser crystallographic software," J. Appl. Crystallogr. 40, 658-674 (2007).

Mitsuhashi et al., "Prognostic significance of PRAME expression based on immunohistochemistry for diffuse large B-cell lymphoma patients treated with R-CHOP therapy," Int. J Hematol. 100(1):88-95 (2014).

O'Callaghan et al., "BirA enzyme: production and application in the study of membrane receptor-ligand interactions by site-specific biotinylation," Anal Biochem 266(1): 9-15 (1999).

Proto-Siqueira et al., "PRAME is a membrane and cytoplasmic protein aberrantly expressed in chronic lymphocytic leukemia and mantle cell lymphoma," Leuk Res. 30(11):1333-1339 (2006).

Purbhoo et al., "Quantifying and Imaging NY-ESO-1/LAGE-1-Derived Epitopes on Tumor Cells Using High Affinity T Cell Receptors," J Immunol 176(12): 7308-7316 (2006).

Rudolph et al., "How TCRs bind MHCs, peptides, and coreceptors," Annu Rev Immunol. 24, 419-466 (2006).

Schodin et al, "Binding properties and solubility of single-chain T cell receptors expressed in *E. coli*," Molecular Immunology 33(9):819-829 (1996).

Szczepanski et al., "PRAME expression in head and neck cancer correlates with markers of poor prognosis and might help in selecting candidates for retinoid chemoprevention in pre-malignant lesions," Oral Oncol. 49(2):144-51 (2013).

Van Baren et al., "PRAME, a gene encoding an antigen recognized on a human melanoma by cytolytic T cells, is expressed in acute leukaemia cells," Br J Haematol. 102(5):1376-9 (1998).

Vonrhein et al., "Data processing and analysis with the autoPROC toolbox," Acta. Crystal. Sect D Biological Crystallogr. 67, 293-302 (2011).

Weidanz et al., "Display of functional $\alpha\beta$ single-chain T-cell receptor molecules on the surface of bacteriophage," J Immunol Methods. 221(1-2):59-76 (1998).

Willuda et al., "Tumor Targeting of Mono-, Di-, and Tetravalent Anti-p185$^{HER-2}$ Miniantibodies Multimerized by Self-associating Peptides," J. Biol. Chem. 276 (17) 14385-14392 (2001).

Wilson et al., "Specificity and degeneracy of T cells," Mol Immunol. 40(14-15):1047-55 (2004).

Winter et al., "DIALS: Implementation and evaluation of a new integration package," Acta. Cryst. Sect D Struct Biology. 74, 85-97 (2018).

Winter, "xia2: an expert system for macromolecular crystallography data reduction," J Appl. Crystal. 43, 186-190 (2010).

Wooldridge et al., "A single autoimmune T cell receptor recognizes more than a million different peptides," J Biol Chem. 287(2):1168-77 (2012).

Zhao et al., "High-affinity TCRs generated by phage display provide CD4+ T cells with the ability to recognize and kill tumor cell lines," J Immunol. 179(9):5845-54 (2007).

International Search Report and Written Opinion in PCT/EP2024/050226, dated Mar. 20, 2024.

SEQUENCE LISTING

```
Sequence total quantity: 141
SEQ ID NO: 1            moltype = AA  length = 9
FEATURE                 Location/Qualifiers
source                  1..9
                        mol_type = protein
```

```
                           organism = Homo sapiens
SEQUENCE: 1
PYLGQMINL                                                                  9

SEQ ID NO: 2            moltype = AA  length = 200
FEATURE                 Location/Qualifiers
source                  1..200
                        mol_type = protein
                        organism = synthetic construct
SEQUENCE: 2
AQSVTQLDSH VSVSEGTPVL LRCNYSSSYS PSLFWYVQHP NKGLQLLLKY TSAATLVKGI          60
NGFEAEFKKS ETSPHLTKPS AHMSDAAEYF CVVSAPNRDD KIIFGKGTRL HILPNIQNPD         120
PAVYQLRDSK SSDKSVCLFT DFDSQTNVSQ SKDSDVYITD KCVLDMRSMD FKSNSAVAWS         180
NKSDFACANA FNNSIIPEDT                                                    200

SEQ ID NO: 3            moltype = AA  length = 114
FEATURE                 Location/Qualifiers
source                  1..114
                        mol_type = protein
                        organism = synthetic construct
SEQUENCE: 3
AQSVTQLDSH VSVSEGTPVL LRCNYSSSYS PSLFWYVQHP NKGLQLLLKY TSAATLVKGI          60
NGFEAEFKKS ETSPHLTKPS AHMSDAAEYF CVVSAPNRDD KIIFGKGTRL HILP              114

SEQ ID NO: 4            moltype = AA  length = 86
FEATURE                 Location/Qualifiers
source                  1..86
                        mol_type = protein
                        organism = synthetic construct
SEQUENCE: 4
NIQNPDPAVY QLRDSKSSDK SVCLFTDFDS QTNVSQSKDS DVYITDKCVL DMRSMDFKSN          60
SAVAWSNKSD FACANAFNNS IIPEDT                                              86

SEQ ID NO: 5            moltype = AA  length = 6
FEATURE                 Location/Qualifiers
source                  1..6
                        mol_type = protein
                        organism = synthetic construct
SEQUENCE: 5
SSYSPS                                                                     6

SEQ ID NO: 6            moltype = AA  length = 8
FEATURE                 Location/Qualifiers
source                  1..8
                        mol_type = protein
                        organism = synthetic construct
SEQUENCE: 6
YTSAATLV                                                                   8

SEQ ID NO: 7            moltype = AA  length = 12
FEATURE                 Location/Qualifiers
source                  1..12
                        mol_type = protein
                        organism = synthetic construct
SEQUENCE: 7
VVSAPNRDDK II                                                             12

SEQ ID NO: 8            moltype = AA  length = 26
FEATURE                 Location/Qualifiers
source                  1..26
                        mol_type = protein
                        organism = synthetic construct
SEQUENCE: 8
AQSVTQLDSH VSVSEGTPVL LRCNYS                                              26

SEQ ID NO: 9            moltype = AA  length = 17
FEATURE                 Location/Qualifiers
source                  1..17
                        mol_type = protein
                        organism = synthetic construct
SEQUENCE: 9
LFWYVQHPNK GLQLLLK                                                        17

SEQ ID NO: 10           moltype = AA  length = 34
FEATURE                 Location/Qualifiers
source                  1..34
                        mol_type = protein
SEQUENCE: 10
```

```
KGINGFEAEF KKSETSFHLT KPSAHMSDAA EYFC                                    34

SEQ ID NO: 11           moltype = AA   length = 11
FEATURE                 Location/Qualifiers
source                  1..11
                        mol_type = protein
                        organism = synthetic construct
SEQUENCE: 11
FGKGTRLHIL P                                                            11

SEQ ID NO: 12           moltype = AA   length = 247
FEATURE                 Location/Qualifiers
source                  1..247
                        mol_type = protein
                        organism = synthetic construct
SEQUENCE: 12
DSGVTQTPKH LITATGQRVT LRCSPRSGDL SVYWYQQSLD QGLQFLIQYY NGEERAKGNI        60
LERFSAQQFP DLHSELNLSS LELGDSALYF CASSVWSSGG ASAGELFFGE GSRLTVLEDL        120
KNVFPPEVAV FEPSEAEISH TQKATLVCLA TGFYPDHVEL SWWVNGKEVH SGVCTDPQPL        180
KEQPALNDSR YALSSRLRVS ATFWQDPRNH FRCQVQFYGL SENDEWTQDR AKPVTQIVSA        240
EAWGRAD                                                                 247

SEQ ID NO: 13           moltype = AA   length = 117
FEATURE                 Location/Qualifiers
source                  1..117
                        mol_type = protein
                        organism = synthetic construct
SEQUENCE: 13
DSGVTQTPKH LITATGQRVT LRCSPRSGDL SVYWYQQSLD QGLQFLIQYY NGEERAKGNI        60
LERFSAQQFP DLHSELNLSS LELGDSALYF CASSVWSSGG ASAGELFFGE GSRLTVL          117

SEQ ID NO: 14           moltype = AA   length = 130
FEATURE                 Location/Qualifiers
source                  1..130
                        mol_type = protein
                        organism = synthetic construct
SEQUENCE: 14
EDLKNVFPPE VAVFEPSEAE ISHTQKATLV CLATGFYPDH VELSWWVNGK EVHSGVCTDP        60
QPLKEQPALN DSRYALSSRL RVSATFWQDP RNHFRCQVQF YGLSENDEWT QDRAKPVTQI        120
VSAEAWGRAD                                                              130

SEQ ID NO: 15           moltype = AA   length = 5
FEATURE                 Location/Qualifiers
source                  1..5
                        mol_type = protein
                        organism = synthetic construct
SEQUENCE: 15
SGDLS                                                                   5

SEQ ID NO: 16           moltype = AA   length = 6
FEATURE                 Location/Qualifiers
source                  1..6
                        mol_type = protein
                        organism = synthetic construct
SEQUENCE: 16
YYNGEE                                                                  6

SEQ ID NO: 17           moltype = AA   length = 16
FEATURE                 Location/Qualifiers
source                  1..16
                        mol_type = protein
                        organism = synthetic construct
SEQUENCE: 17
ASSVWSSGGA SAGELF                                                       16

SEQ ID NO: 18           moltype = AA   length = 26
FEATURE                 Location/Qualifiers
source                  1..26
                        mol_type = protein
                        organism = synthetic construct
SEQUENCE: 18
DSGVTQTPKH LITATGQRVT LRCSPR                                            26

SEQ ID NO: 19           moltype = AA   length = 17
FEATURE                 Location/Qualifiers
source                  1..17
                        mol_type = protein
                        organism = synthetic construct
SEQUENCE: 19
```

```
VYWYQQSLDQ GLQFLIQ                                                               17

SEQ ID NO: 20           moltype = AA  length = 37
FEATURE                 Location/Qualifiers
source                  1..37
                        mol_type = protein
                        organism = synthetic construct
SEQUENCE: 20
RAKGNILERF SAQQFPDLHS ELNLSSLELG DSALYFC                                          37

SEQ ID NO: 21           moltype = AA  length = 10
FEATURE                 Location/Qualifiers
source                  1..10
                        mol_type = protein
                        organism = synthetic construct
SEQUENCE: 21
FGEGSRLTVL                                                                       10

SEQ ID NO: 22           moltype = AA  length = 114
FEATURE                 Location/Qualifiers
source                  1..114
                        mol_type = protein
                        organism = synthetic construct
SEQUENCE: 22
AQSVTQLDSH VSVSEGTPVL LRCNYSSSYS PSLFWYVQHP NKGLQLLLKY TSAATLVKGI                 60
NGFEAEFKKS ETSFHLTKPS AHMSDAAEYF CVVGAPHRND KIIFGKGTRL HILP                      114

SEQ ID NO: 23           moltype = AA  length = 12
FEATURE                 Location/Qualifiers
source                  1..12
                        mol_type = protein
                        organism = synthetic construct
SEQUENCE: 23
VVGAPHRNDK II                                                                    12

SEQ ID NO: 24           moltype = AA  length = 114
FEATURE                 Location/Qualifiers
source                  1..114
                        mol_type = protein
                        organism = synthetic construct
SEQUENCE: 24
AQSVTQLDSH VSVSEGTPVL LRCNYSSSYS PSLFWYVQHP NKGLQLLLKY IGNDTLVKGI                 60
NGFEAEFKKS ETSFHLTKPS AHMSDAAEYF CVVGAPHRND KIIFGKGTRL HILP                      114

SEQ ID NO: 25           moltype = AA  length = 8
FEATURE                 Location/Qualifiers
source                  1..8
                        mol_type = protein
                        organism = synthetic construct
SEQUENCE: 25
YIGNDTLV                                                                          8

SEQ ID NO: 26           moltype = AA  length = 114
FEATURE                 Location/Qualifiers
source                  1..114
                        mol_type = protein
                        organism = synthetic construct
SEQUENCE: 26
AQSVTQLDSH VSVSEGTPVL LRCNYSSSYS PSLFWYVQHP NKGLQLLLKY IGNVTLVKGI                 60
QGFEAEFKKS ETSFHLTKPS AHMSDAAEYF CVVGAPHRND KIIFGKGTRL HILP                      114

SEQ ID NO: 27           moltype = AA  length = 8
FEATURE                 Location/Qualifiers
source                  1..8
                        mol_type = protein
                        organism = synthetic construct
SEQUENCE: 27
YIGNVTLV                                                                          8

SEQ ID NO: 28           moltype = AA  length = 34
FEATURE                 Location/Qualifiers
source                  1..34
                        mol_type = protein
                        organism = synthetic construct
SEQUENCE: 28
KGIQGFEAEF KKSETSFHLT KPSAHMSDAA EYFC                                             34

SEQ ID NO: 29           moltype = AA  length = 114
FEATURE                 Location/Qualifiers
```

```
source                  1..114
                        mol_type = protein
                        organism = synthetic construct
SEQUENCE: 29
AQSVTQLDSH VSVSEGTPVL LRCNYSSSYS PSLFWYVQHP NKGLQLLLKY IGNVTLVKGI    60
QGFEAEFKKS ETSFHLTKPS AHMSDAAEYF CVVGAPHHND KIIFGKGTRL HILP         114

SEQ ID NO: 30           moltype = AA   length = 12
FEATURE                 Location/Qualifiers
source                  1..12
                        mol_type = protein
                        organism = synthetic construct
SEQUENCE: 30
VVGAPHHNDK II                                                         12

SEQ ID NO: 31           moltype = AA   length = 117
FEATURE                 Location/Qualifiers
source                  1..117
                        mol_type = protein
                        organism = synthetic construct
SEQUENCE: 31
DSGVTQTPKH LITATGQRVT LRCSPRSGDY SVYWYQQSLD QGLQFLIQYY NGEERAKGNI    60
LERFSAQQFP DLHSELNLSS LELGDSALYF CASSVWSNGG ASSGNLSFGE GSRLTVL      117

SEQ ID NO: 32           moltype = AA   length = 5
FEATURE                 Location/Qualifiers
source                  1..5
                        mol_type = protein
                        organism = synthetic construct
SEQUENCE: 32
SGDYS                                                                  5

SEQ ID NO: 33           moltype = AA   length = 16
FEATURE                 Location/Qualifiers
source                  1..16
                        mol_type = protein
                        organism = synthetic construct
SEQUENCE: 33
ASSVWSNGGA SSGNLS                                                     16

SEQ ID NO: 34           moltype = AA   length = 117
FEATURE                 Location/Qualifiers
source                  1..117
                        mol_type = protein
                        organism = synthetic construct
SEQUENCE: 34
DSGVTQTPKH LIKATGQRVT LRCSPRSGDY SVYWYQQSLD QGPQFLFQYY NAEERAKGNI    60
PERFSAQQFP DLHSELNLSS LELGDSALYI CASSVWSIGG ASSGNLSFGE GSRLTVL      117

SEQ ID NO: 35           moltype = AA   length = 6
FEATURE                 Location/Qualifiers
source                  1..6
                        mol_type = protein
                        organism = synthetic construct
SEQUENCE: 35
YYNAEE                                                                 6

SEQ ID NO: 36           moltype = AA   length = 16
FEATURE                 Location/Qualifiers
source                  1..16
                        mol_type = protein
                        organism = synthetic construct
SEQUENCE: 36
ASSVWSIGGA SSGNLS                                                     16

SEQ ID NO: 37           moltype = AA   length = 26
FEATURE                 Location/Qualifiers
source                  1..26
                        mol_type = protein
                        organism = synthetic construct
SEQUENCE: 37
DSGVTQTPKH LIKATGQRVT LRCSPR                                          26

SEQ ID NO: 38           moltype = AA   length = 17
FEATURE                 Location/Qualifiers
source                  1..17
                        mol_type = protein
                        organism = synthetic construct
SEQUENCE: 38
```

-continued

```
VYWYQQSLDQ GPQFLFQ                                                        17

SEQ ID NO: 39           moltype = AA  length = 37
FEATURE                 Location/Qualifiers
source                  1..37
                        mol_type = protein
                        organism = synthetic construct
SEQUENCE: 39
RAKGNIPERF SAQQFPDLHS ELNLSSLELG DSALYIC                                   37

SEQ ID NO: 40           moltype = AA  length = 117
FEATURE                 Location/Qualifiers
source                  1..117
                        mol_type = protein
                        organism = synthetic construct
SEQUENCE: 40
DSGVTQTPKH LIKATGQRVT LRCSPRSGDY SVYWYQQSLD QGPQFLFQYY NAEERAKGNI          60
PERFSAQQFP DLHSELNLSS LELGDSALYI CASSIWSIGG ASSGNLSFGE GSRLTVL            117

SEQ ID NO: 41           moltype = AA  length = 16
FEATURE                 Location/Qualifiers
source                  1..16
                        mol_type = protein
                        organism = synthetic construct
SEQUENCE: 41
ASSIWSIGGA SSGNLS                                                          16

SEQ ID NO: 42           moltype = AA  length = 200
FEATURE                 Location/Qualifiers
source                  1..200
                        mol_type = protein
                        organism = synthetic construct
SEQUENCE: 42
AQSVTQLDSH VSVSEGTPVL LRCNYSSSYS PSLFWYVQHP NKGLQLLLKY TSAATLVKGI          60
NGFEAEFKKS ETSPHLTKPS AHMSDAAEYF CVVGAPHRND KIIFGKGTRL HILPNIQNPD         120
PAVYQLRDSK SSDKSVCLFT DFDSQTNVSQ SKDSDVYITD KCVLDMRSMD FKSNSAVAWS         180
NKSDFACANA FNNSIIPEDT                                                    200

SEQ ID NO: 43           moltype =     length =
SEQUENCE: 43
000

SEQ ID NO: 44           moltype = AA  length = 200
FEATURE                 Location/Qualifiers
source                  1..200
                        mol_type = protein
                        organism = synthetic construct
SEQUENCE: 44
AQSVTQLDSH VSVSEGTPVL LRCNYSSSYS PSLFWYVQHP NKGLQLLLKY IGNDTLVKGI          60
NGFEAEFKKS ETSPHLTKPS AHMSDAAEYF CVVGAPHRND KIIFGKGTRL HILPNIQNPD         120
PAVYQLRDSK SSDKSVCLFT DFDSQTNVSQ SKDSDVYITD KCVLDMRSMD FKSNSAVAWS         180
NKSDFACANA FNNSIIPEDT                                                    200

SEQ ID NO: 45           moltype = AA  length = 247
FEATURE                 Location/Qualifiers
source                  1..247
                        mol_type = protein
                        organism = synthetic construct
SEQUENCE: 45
DSGVTQTPKH LITATGQRVT LRCSPRSGDY SVYWYQQSLD QGLQFLIQYY NGEERAKGNI          60
LERFSAQQFP DLHSELNLSS LELGDSALYF CASSVWSNGG ASSGNLSFGE GSRLTVLEDL         120
KNVFPPEVAV FEPSEAEISH TQKATLVCLA TGFYPDHVEL SWWVNGKEVH SGVCTDPQPL         180
KEQPALNDSR YALSSRLRVS ATFWQDPRNH FRCQVQFYGL SENDEWTQDR AKPVTQIVSA         240
EAWGRAD                                                                  247

SEQ ID NO: 46           moltype = AA  length = 200
FEATURE                 Location/Qualifiers
source                  1..200
                        mol_type = protein
                        organism = synthetic construct
SEQUENCE: 46
AQSVTQLDSH VSVSEGTPVL LRCNYSSSYS PSLFWYVQHP NKGLQLLLKY IGNVTLVKGI          60
QGFEAEFKKS ETSPHLTKPS AHMSDAAEYF CVVGAPHRND KIIFGKGTRL HILPNIQNPD         120
PAVYQLRDSK SSDKSVCLFT DFDSQTNVSQ SKDSDVYITD KCVLDMRSMD FKSNSAVAWS         180
NKSDFACANA FNNSIIPEDT                                                    200

SEQ ID NO: 47           moltype = AA  length = 247
FEATURE                 Location/Qualifiers
source                  1..247
```

```
                        mol_type = protein
                        organism = synthetic construct
SEQUENCE: 47
DSGVTQTPKH LIKATGQRVT LRCSPRSGDY SVYWYQQSLD QGPQFLFQYY NAEERAKGNI    60
PERFSAQQFP DLHSELNLSS LELGDSALYI CASSVWSIGG ASSGNLSFGE GSRLTVLEDM   120
KNVFPPEVAV FEPSEAEISH TQKATLVCLA TGFYPDHVEL SWWVNGKEVH SGVCTDPQPL   180
KEQPALNDSR YALSSRLRVS ATFWQDPRNH FRCQVQFYGL SENDEWTQDR AKPVTQIVSA   240
EAWGRAD                                                             247

SEQ ID NO: 48           moltype = AA   length = 130
FEATURE                 Location/Qualifiers
source                  1..130
                        mol_type = protein
                        organism = synthetic construct
SEQUENCE: 48
EDMKNVFPPE VAVFEPSEAE ISHTQKATLV CLATGFYPDH VELSWWVNGK EVHSGVCTDP    60
QPLKEQPALN DSRYALSSRL RVSATFWQDP RNHFRCQVQF YGLSENDEWT QDRAKPVTQI   120
VSAEAWGRAD                                                          130

SEQ ID NO: 49           moltype = AA   length = 200
FEATURE                 Location/Qualifiers
source                  1..200
                        mol_type = protein
                        organism = synthetic construct
SEQUENCE: 49
AQSVTQLDSH VSVSEGTPVL LRCNYSSSYS PSLFWYVQHP NKGLQLLLKY IGNVTLVKGI    60
QGFEAEFKKS ETSFHLTKPS AHMSDAAEYF CVVGAPHHND KIIFGKGTRL HILPNIQNPD   120
PAVYQLRDSK SSDKSVCLFT DFDSQTNVSQ SKDSDVYITD KCVLDMRSMD FKSNSAVAWS   180
NKSDFACANA FNNSIIPEDT                                               200

SEQ ID NO: 50           moltype = AA   length = 247
FEATURE                 Location/Qualifiers
source                  1..247
                        mol_type = protein
                        organism = synthetic construct
SEQUENCE: 50
DSGVTQTPKH LIKATGQRVT LRCSPRSGDY SVYWYQQSLD QGPQFLFQYY NAEERAKGNI    60
PERFSAQQFP DLHSELNLSS LELGDSALYI CASSIWSIGG ASSGNLSFGE GSRLTVLEDM   120
KNVFPPEVAV FEPSEAEISH TQKATLVCLA TGFYPDHVEL SWWVNGKEVH SGVCTDPQPL   180
KEQPALNDSR YALSSRLRVS ATFWQDPRNH FRCQVQFYGL SENDEWTQDR AKPVTQIVSA   240
EAWGRAD                                                             247

SEQ ID NO: 51           moltype = AA   length = 253
FEATURE                 Location/Qualifiers
source                  1..253
                        mol_type = protein
                        organism = synthetic construct
SEQUENCE: 51
AIQMTQSPSS LSASVGDRVT ITCRASQDIR NYLNWYQQKP GKAPKLLIYY TSRLESGVPS    60
RFSGSGSGTD YTLTISSLQP EDFATYYCQQ GNTLPWTFGQ GTKVEIKGGG GSGGGGSGGG   120
GSGGGGSGGG SEVQLVESGG GLVQPGGSLR LSCAASGYSF TGYTMNWVRQ APGKGLEWVA   180
LINPYKGVST YNQKFKDRFT ISVDKSKNTA YLQMNSLRAE DTAVYYCARS GYYGDSDWYF   240
DVWGQGTLVT VSS                                                      253

SEQ ID NO: 52           moltype = AA   length = 6
FEATURE                 Location/Qualifiers
source                  1..6
                        mol_type = protein
                        organism = synthetic construct
SEQUENCE: 52
QDIRNY                                                              6

SEQ ID NO: 53           moltype =      length =
SEQUENCE: 53
000

SEQ ID NO: 54           moltype = AA   length = 9
FEATURE                 Location/Qualifiers
source                  1..9
                        mol_type = protein
                        organism = synthetic construct
SEQUENCE: 54
QQGNTLPWT                                                           9

SEQ ID NO: 55           moltype = AA   length = 122
FEATURE                 Location/Qualifiers
source                  1..122
                        mol_type = protein
                        organism = synthetic construct
```

```
SEQUENCE: 55
EVQLVESGGG LVQPGGSLRL SCAASGYSFT GYTMNWVRQA PGKGLEWVAL INPYKGVSTY    60
NQKFKDRFTI SVDKSKNTAY LQMNSLRAED TAVYYCARSG YYGDSDWYFD VWGQGTLVTV   120
SS                                                                  122

SEQ ID NO: 56            moltype = AA  length = 8
FEATURE                  Location/Qualifiers
source                   1..8
                         mol_type = protein
                         organism = synthetic construct
SEQUENCE: 56
GYSFTGYT                                                              8

SEQ ID NO: 57            moltype = AA  length = 8
FEATURE                  Location/Qualifiers
source                   1..8
                         mol_type = protein
                         organism = synthetic construct
SEQUENCE: 57
INPYKGVS                                                              8

SEQ ID NO: 58            moltype = AA  length = 15
FEATURE                  Location/Qualifiers
source                   1..15
                         mol_type = protein
                         organism = synthetic construct
SEQUENCE: 58
ARSGYYGDSD WYFDV                                                     15

SEQ ID NO: 59            moltype = AA  length = 24
FEATURE                  Location/Qualifiers
source                   1..24
                         mol_type = protein
                         organism = synthetic construct
SEQUENCE: 59
GGGGSGGGGS GGGGSGGGGS GGGS                                           24

SEQ ID NO: 60            moltype = AA  length = 253
FEATURE                  Location/Qualifiers
source                   1..253
                         mol_type = protein
                         organism = synthetic construct
SEQUENCE: 60
AIQMTQSPSS LSASVGDRVT ITCRASQDIR NYLNWYQQKP GKAPKLLIYY TSRLESGVPS    60
RFSGSGSGTD YTLTISSLQP EDFATYYCQQ GNTLPWTFGQ GTKVEIKGGG GSGGGGSGGG   120
GSGGGGSGGG SEVQLVESGG GLVQPGGSLR LSCAASGYSF TGYAMNWVRQ APGKGLEWVA   180
LINPYKGVST YNQKFKDRFT FSVDKSKNTA YLQMNSLRAE DTAVYYCARS GYYGDSDWYF   240
DVWGQGTLVT VSS                                                      253

SEQ ID NO: 61            moltype = AA  length = 122
FEATURE                  Location/Qualifiers
source                   1..122
                         mol_type = protein
                         organism = synthetic construct
SEQUENCE: 61
EVQLVESGGG LVQPGGSLRL SCAASGYSFT GYAMNWVRQA PGKGLEWVAL INPYKGVSTY    60
NQKFKDRFTF SVDKSKNTAY LQMNSLRAED TAVYYCARSG YYGDSDWYFD VWGQGTLVTV   120
SS                                                                  122

SEQ ID NO: 62            moltype = AA  length = 8
FEATURE                  Location/Qualifiers
source                   1..8
                         mol_type = protein
                         organism = synthetic construct
SEQUENCE: 62
GYSFTGYA                                                              8

SEQ ID NO: 63            moltype = AA  length = 505
FEATURE                  Location/Qualifiers
source                   1..505
                         mol_type = protein
                         organism = synthetic construct
SEQUENCE: 63
AIQMTQSPSS LSASVGDRVT ITCRASQDIR NYLNWYQQKP GKAPKLLIYY TSRLESGVPS    60
RFSGSGSGTD YTLTISSLQP EDFATYYCQQ GNTLPWTFGQ GTKVEIKGGG GSGGGGSGGG   120
GSGGGGSGGG SEVQLVESGG GLVQPGGSLR LSCAASGYSF TGYTMNWVRQ APGKGLEWVA   180
LINPYKGVST YNQKFKDRFT ISVDKSKNTA YLQMNSLRAE DTAVYYCARS GYYGDSDWYF   240
DVWGQGTLVT VSSGGGGSDS GVTQTPKHLI TATGQRVTLR CSPRSGDLSV YWYQQSLDQG   300
LQFLIQYYNG EERAKGNILE RFSAQQFPDL HSELNLSSLE LGDSALYFCA SSVWSSGGAS   360
```

```
AGELFFGEGS RLTVLEDLKN VFPPEVAVFE PSEAEISHTQ KATLVCLATG FYPDHVELSW    420
WVNGKEVHSG VCTDPQPLKE QPALNDSRYA LSSRLRVSAT FWQDPRNHFR CQVQFYGLSE    480
NDEWTQDRAK PVTQIVSAEA WGRAD                                         505

SEQ ID NO: 64           moltype = AA   length = 5
FEATURE                 Location/Qualifiers
source                  1..5
                        mol_type = protein
                        organism = synthetic construct
SEQUENCE: 64
GGGGS                                                               5

SEQ ID NO: 65           moltype = AA   length = 505
FEATURE                 Location/Qualifiers
source                  1..505
                        mol_type = protein
                        organism = synthetic construct
SEQUENCE: 65
AIQMTQSPSS LSASVGDRVT ITCRASQDIR NYLNWYQQKP GKAPKLLIYY TSRLESGVPS    60
RFSGSGSGTD YTLTISSLQP EDFATYYCQQ GNTLPWTFGQ GTKVEIKGGG GSGGGGSGGG    120
GSGGGGSGGG SEVQLVESGG GLVQPGGSLR LSCAASGYSF TGYTMNWVRQ APGKGLEWVA    180
LINPYKGVST YNQKFKDRFT ISVDKSKNTA YLQMNSLRAE DTAVYYCARS GYYGDSDWYF    240
DVWGQGTLVT VSSGGGGSDS GVTQTPKHLI TATGQRVTLR CSPRSGDYSV YWYQQSLDQG    300
LQFLIQYYNG EERAKGNILE RFSAQQFPDL HSELNLSSLE LGDSALYFCA SSVWSNGGAS    360
SGNLSFGEGS RLTVLEDLKN VFPPEVAVFE PSEAEISHTQ KATLVCLATG FYPDHVELSW    420
WVNGKEVHSG VCTDPQPLKE QPALNDSRYA LSSRLRVSAT FWQDPRNHFR CQVQFYGLSE    480
NDEWTQDRAK PVTQIVSAEA WGRAD                                         505

SEQ ID NO: 66           moltype = AA   length = 505
FEATURE                 Location/Qualifiers
source                  1..505
                        mol_type = protein
                        organism = synthetic construct
SEQUENCE: 66
AIQMTQSPSS LSASVGDRVT ITCRASQDIR NYLNWYQQKP GKAPKLLIYY TSRLESGVPS    60
RFSGSGSGTD YTLTISSLQP EDFATYYCQQ GNTLPWTFGQ GTKVEIKGGG GSGGGGSGGG    120
GSGGGGSGGG SEVQLVESGG GLVQPGGSLR LSCAASGYSF TGYTMNWVRQ APGKGLEWVA    180
LINPYKGVST YNQKFKDRFT ISVDKSKNTA YLQMNSLRAE DTAVYYCARS GYYGDSDWYF    240
DVWGQGTLVT VSSGGGGSDS GVTQTPKHLI KATGQRVTLR CSPRSGDYSV YWYQQSLDQG    300
PQFLFQYYNA EERAKGNIPE RFSAQQFPDL HSELNLSSLE LGDSALYICA SSVWSIGGAS    360
SGNLSFGEGS RLTVLEDMKN VFPPEVAVFE PSEAEISHTQ KATLVCLATG FYPDHVELSW    420
WVNGKEVHSG VCTDPQPLKE QPALNDSRYA LSSRLRVSAT FWQDPRNHFR CQVQFYGLSE    480
NDEWTQDRAK PVTQIVSAEA WGRAD                                         505

SEQ ID NO: 67           moltype = AA   length = 505
FEATURE                 Location/Qualifiers
source                  1..505
                        mol_type = protein
                        organism = synthetic construct
SEQUENCE: 67
AIQMTQSPSS LSASVGDRVT ITCRASQDIR NYLNWYQQKP GKAPKLLIYY TSRLESGVPS    60
RFSGSGSGTD YTLTISSLQP EDFATYYCQQ GNTLPWTFGQ GTKVEIKGGG GSGGGGSGGG    120
GSGGGGSGGG SEVQLVESGG GLVQPGGSLR LSCAASGYSF TGYAMNWVRQ APGKGLEWVA    180
LINPYKGVST YNQKFKDRFT FSVDKSKNTA YLQMNSLRAE DTAVYYCARS GYYGDSDWYF    240
DVWGQGTLVT VSSGGGGSDS GVTQTPKHLI KATGQRVTLR CSPRSGDYSV YWYQQSLDQG    300
PQFLFQYYNA EERAKGNIPE RFSAQQFPDL HSELNLSSLE LGDSALYICA SSVWSIGGAS    360
SGNLSFGEGS RLTVLEDMKN VFPPEVAVFE PSEAEISHTQ KATLVCLATG FYPDHVELSW    420
WVNGKEVHSG VCTDPQPLKE QPALNDSRYA LSSRLRVSAT FWQDPRNHFR CQVQFYGLSE    480
NDEWTQDRAK PVTQIVSAEA WGRAD                                         505

SEQ ID NO: 68           moltype = AA   length = 505
FEATURE                 Location/Qualifiers
source                  1..505
                        mol_type = protein
                        organism = synthetic construct
SEQUENCE: 68
AIQMTQSPSS LSASVGDRVT ITCRASQDIR NYLNWYQQKP GKAPKLLIYY TSRLESGVPS    60
RFSGSGSGTD YTLTISSLQP EDFATYYCQQ GNTLPWTFGQ GTKVEIKGGG GSGGGGSGGG    120
GSGGGGSGGG SEVQLVESGG GLVQPGGSLR LSCAASGYSF TGYTMNWVRQ APGKGLEWVA    180
LINPYKGVST YNQKFKDRFT ISVDKSKNTA YLQMNSLRAE DTAVYYCARS GYYGDSDWYF    240
DVWGQGTLVT VSSGGGGSDS GVTQTPKHLI KATGQRVTLR CSPRSGDYSV YWYQQSLDQG    300
PQFLFQYYNA EERAKGNIPE RFSAQQFPDL HSELNLSSLE LGDSALYICA SSIWSIGGAS    360
SGNLSFGEGS RLTVLEDMKN VFPPEVAVFE PSEAEISHTQ KATLVCLATG FYPDHVELSW    420
WVNGKEVHSG VCTDPQPLKE QPALNDSRYA LSSRLRVSAT FWQDPRNHFR CQVQFYGLSE    480
NDEWTQDRAK PVTQIVSAEA WGRAD                                         505

SEQ ID NO: 69           moltype = AA   length = 505
FEATURE                 Location/Qualifiers
source                  1..505
```

```
                              mol_type = protein
                              organism = synthetic construct
SEQUENCE: 69
AIQMTQSPSS LSASVGDRVT ITCRASQDIR NYLNWYQQKP GKAPKLLIYY TSRLESGVPS    60
RFSGSGSGTD YTLTISSLQP EDFATYYCQQ GNTLPWTFGQ GTKVEIKGGG GSGGGGSGGG   120
GSGGGGSGGG SEVQLVESGG GLVQPGGSLR LSCAASGYSF TGYAMNWVRQ APGKGLEWVA   180
LINPYKGVST YNQKFKDRFT FSVDKSKNTA YLQMNSLRAE DTAVYYCARS GYYGDSDWYF   240
DVWGQGTLVT VSSGGGGSDS GVTQTPKHLI KATGQRVTLR CSPRSGDYSV YWYQQSLDQG   300
PQFLFQYYNA EERAKGNIPE RFSAQQFPDL HSELNLSSLE LGDSALYICA SSIWSIGGAS   360
SGNLSFGEGS RLTVLEDMKN VFPPEVAVFE PSEAEISHTQ KATLVCLATG FYPDHVELSW   420
WVNGKEVHSG VCTDPQPLKE QPALNDSRYA LSSRLRVSAT FWQDPRNHFR CQVQFYGLSE   480
NDEWTQDRAK PVTQIVSAEA WGRAD                                         505

SEQ ID NO: 70                 moltype = AA    length = 5
FEATURE                       Location/Qualifiers
source                        1..5
                              mol_type = protein
                              organism = synthetic construct
SEQUENCE: 70
GGGSG                                                                 5

SEQ ID NO: 71                 moltype = AA    length = 5
FEATURE                       Location/Qualifiers
source                        1..5
                              mol_type = protein
                              organism = synthetic construct
SEQUENCE: 71
GGSGG                                                                 5

SEQ ID NO: 72                 moltype = AA    length = 5
FEATURE                       Location/Qualifiers
source                        1..5
                              mol_type = protein
                              organism = synthetic construct
SEQUENCE: 72
GSGGG                                                                 5

SEQ ID NO: 73                 moltype = AA    length = 6
FEATURE                       Location/Qualifiers
source                        1..6
                              mol_type = protein
                              organism = synthetic construct
SEQUENCE: 73
GSGGGP                                                                6

SEQ ID NO: 74                 moltype = AA    length = 5
FEATURE                       Location/Qualifiers
source                        1..5
                              mol_type = protein
                              organism = synthetic construct
SEQUENCE: 74
GGEPS                                                                 5

SEQ ID NO: 75                 moltype = AA    length = 7
FEATURE                       Location/Qualifiers
source                        1..7
                              mol_type = protein
                              organism = synthetic construct
SEQUENCE: 75
GGEGGGP                                                               7

SEQ ID NO: 76                 moltype = AA    length = 12
FEATURE                       Location/Qualifiers
source                        1..12
                              mol_type = protein
                              organism = synthetic construct
SEQUENCE: 76
GGEGGGSEGG GS                                                        12

SEQ ID NO: 77                 moltype = AA    length = 8
FEATURE                       Location/Qualifiers
source                        1..8
                              mol_type = protein
                              organism = synthetic construct
SEQUENCE: 77
GGGSGGGG                                                              8

SEQ ID NO: 78                 moltype = AA    length = 20
FEATURE                       Location/Qualifiers
```

```
                        -continued source                  1..20
                        mol_type = protein
                        organism = synthetic construct
SEQUENCE: 78
GGGGSGGGGS GGGGSGGGGS                                              20

SEQ ID NO: 79           moltype = AA   length = 5
FEATURE                 Location/Qualifiers
source                  1..5
                        mol_type = protein
                        organism = synthetic construct
SEQUENCE: 79
EAAAK                                                               5

SEQ ID NO: 80           moltype = AA   length = 15
FEATURE                 Location/Qualifiers
source                  1..15
                        mol_type = protein
                        organism = synthetic construct
SEQUENCE: 80
EAAAKEAAAK EAAAK                                                   15

SEQ ID NO: 81           moltype = AA   length = 9
FEATURE                 Location/Qualifiers
source                  1..9
                        mol_type = protein
                        organism = Homo sapiens
SEQUENCE: 81
PYTGQQISL                                                           9

SEQ ID NO: 82           moltype = AA   length = 9
FEATURE                 Location/Qualifiers
source                  1..9
                        mol_type = protein
                        organism = Homo sapiens
SEQUENCE: 82
PYLGQAPFL                                                           9

SEQ ID NO: 83           moltype = AA   length = 9
FEATURE                 Location/Qualifiers
source                  1..9
                        mol_type = protein
                        organism = Homo sapiens
SEQUENCE: 83
PYLSTMINY                                                           9

SEQ ID NO: 84           moltype = AA   length = 9
FEATURE                 Location/Qualifiers
source                  1..9
                        mol_type = protein
                        organism = Homo sapiens
SEQUENCE: 84
PYLGSKISL                                                           9

SEQ ID NO: 85           moltype = AA   length = 107
FEATURE                 Location/Qualifiers
source                  1..107
                        mol_type = protein
                        organism = synthetic construct
SEQUENCE: 85
AIQMTQSPSS LSASVGDRVT ITCRASQDIR NYLNWYQQKP GKAPKLLIYY TSRLESGVPS   60
RFSGSGSGTD YTLTISSLQP EDFATYYCQQ GNTLPWTFGQ GTKVEIK                107

SEQ ID NO: 86           moltype = AA   length = 13
FEATURE                 Location/Qualifiers
source                  1..13
                        mol_type = protein
                        organism = synthetic construct
SEQUENCE: 86
AFISWRSSGD KLT                                                     13

SEQ ID NO: 87           moltype = AA   length = 15
FEATURE                 Location/Qualifiers
source                  1..15
                        mol_type = protein
                        organism = synthetic construct
SEQUENCE: 87
ASSSPLSGPL ASPLH                                                   15
```

-continued

| | | |
|---|---|---|
| SEQ ID NO: 88<br>FEATURE<br>source | moltype = AA   length = 12<br>Location/Qualifiers<br>1..12<br>mol_type = protein<br>organism = synthetic construct | |
| SEQUENCE: 88<br>AVRGGGGADG LT | | 12 |
| SEQ ID NO: 89<br>FEATURE<br>source | moltype = AA   length = 10<br>Location/Qualifiers<br>1..10<br>mol_type = protein<br>organism = synthetic construct | |
| SEQUENCE: 89<br>ASSLVGTEAF | | 10 |
| SEQ ID NO: 90<br>FEATURE<br>source | moltype = AA   length = 13<br>Location/Qualifiers<br>1..13<br>mol_type = protein<br>organism = synthetic construct | |
| SEQUENCE: 90<br>AAHPGGTSYG KLT | | 13 |
| SEQ ID NO: 91<br>FEATURE<br>source | moltype = AA   length = 12<br>Location/Qualifiers<br>1..12<br>mol_type = protein<br>organism = synthetic construct | |
| SEQUENCE: 91<br>ASTPWLGIQG YT | | 12 |
| SEQ ID NO: 92<br>FEATURE<br>source | moltype = AA   length = 13<br>Location/Qualifiers<br>1..13<br>mol_type = protein<br>organism = synthetic construct | |
| SEQUENCE: 92<br>AVNGPNNAGN MLT | | 13 |
| SEQ ID NO: 93<br>FEATURE<br>source | moltype = AA   length = 12<br>Location/Qualifiers<br>1..12<br>mol_type = protein<br>organism = synthetic construct | |
| SEQUENCE: 93<br>ASSPGGFGQP QH | | 12 |
| SEQ ID NO: 94<br>FEATURE<br>source | moltype = AA   length = 10<br>Location/Qualifiers<br>1..10<br>mol_type = protein<br>organism = synthetic construct | |
| SEQUENCE: 94<br>AVNKGFQKLV | | 10 |
| SEQ ID NO: 95<br>FEATURE<br>source | moltype = AA   length = 12<br>Location/Qualifiers<br>1..12<br>mol_type = protein<br>organism = synthetic construct | |
| SEQUENCE: 95<br>ASSEGWGGQP QH | | 12 |
| SEQ ID NO: 96<br>FEATURE<br>source | moltype = AA   length = 11<br>Location/Qualifiers<br>1..11<br>mol_type = protein<br>organism = synthetic construct | |
| SEQUENCE: 96<br>AVPNPSARQL T | | 11 |
| SEQ ID NO: 97<br>FEATURE<br>source | moltype = AA   length = 12<br>Location/Qualifiers<br>1..12<br>mol_type = protein<br>organism = synthetic construct | |
| SEQUENCE: 97<br>ASSLEGQGVE QF | | 12 |

| | | |
|---|---|---|
| SEQ ID NO: 98<br>FEATURE<br>source | moltype = AA   length = 11<br>Location/Qualifiers<br>1..11<br>mol_type = protein<br>organism = synthetic construct | |
| SEQUENCE: 98<br>APAAAAGNKL T | | 11 |
| SEQ ID NO: 99<br>FEATURE<br>source | moltype = AA   length = 12<br>Location/Qualifiers<br>1..12<br>mol_type = protein<br>organism = synthetic construct | |
| SEQUENCE: 99<br>ASSLGHKSYE QY | | 12 |
| SEQ ID NO: 100<br>FEATURE<br>source | moltype = AA   length = 11<br>Location/Qualifiers<br>1..11<br>mol_type = protein<br>organism = synthetic construct | |
| SEQUENCE: 100<br>AVDSSNTGKL I | | 11 |
| SEQ ID NO: 101<br>FEATURE<br>source | moltype = AA   length = 11<br>Location/Qualifiers<br>1..11<br>mol_type = protein<br>organism = synthetic construct | |
| SEQUENCE: 101<br>ASSSYHAYGY T | | 11 |
| SEQ ID NO: 102<br>FEATURE<br>source | moltype = AA   length = 11<br>Location/Qualifiers<br>1..11<br>mol_type = protein<br>organism = synthetic construct | |
| SEQUENCE: 102<br>AVGRDYGQNF V | | 11 |
| SEQ ID NO: 103<br>FEATURE<br>source | moltype = AA   length = 12<br>Location/Qualifiers<br>1..12<br>mol_type = protein<br>organism = synthetic construct | |
| SEQUENCE: 103<br>ASSYQGFNQP QH | | 12 |
| SEQ ID NO: 104<br>FEATURE<br>source | moltype = AA   length = 11<br>Location/Qualifiers<br>1..11<br>mol_type = protein<br>organism = synthetic construct | |
| SEQUENCE: 104<br>GAIWSTLGRL Y | | 11 |
| SEQ ID NO: 105<br>FEATURE<br>source | moltype = AA   length = 11<br>Location/Qualifiers<br>1..11<br>mol_type = protein<br>organism = synthetic construct | |
| SEQUENCE: 105<br>SSFKGVNQPQ H | | 11 |
| SEQ ID NO: 106<br>FEATURE<br>source | moltype = AA   length = 117<br>Location/Qualifiers<br>1..117<br>mol_type = protein<br>organism = synthetic construct | |
| SEQUENCE: 106<br>DSGVTQTPKH LITATGQRVT LRCSPRPGHL SVYWYQQSLD QGLQFLTQYY NGQELAKGNI<br>LERFSAQQFP DLHSELNLSS LELGDSALYF CASSVWSYGG ASAGALFFGE GSRLTVL | | 60<br>117 |
| SEQ ID NO: 107<br>FEATURE<br>source | moltype = AA   length = 117<br>Location/Qualifiers<br>1..117<br>mol_type = protein<br>organism = synthetic construct | |

```
SEQUENCE: 107
DSGVTQTPKH LITATGQRVT LRCSPRSGDL SVYWYQQSLD QGLQFLIQYY NGEERAKGNI    60
LERFSAQQFP DLHSELNLSS LELGDSALYF CASSVWSYGG ASAGALFFGE GSRLTVL     117

SEQ ID NO: 108          moltype = AA   length = 117
FEATURE                 Location/Qualifiers
source                  1..117
                        mol_type = protein
                        organism = synthetic construct
SEQUENCE: 108
DSGVTQTPKH LITATGQRVT LRCSPRSGDL SVYWYQQSLD QGLQFLTQYY NGQELAKGNI    60
LERFSAQQFP DLHSELNLSS LELGDSALYF CASSVWSSGG ASAGELFFGE GSRLTVL     117

SEQ ID NO: 109          moltype = AA   length = 114
FEATURE                 Location/Qualifiers
source                  1..114
                        mol_type = protein
                        organism = synthetic construct
SEQUENCE: 109
AQSVTQLDSH VSVSEGTPVL LRCNYSSSYS PSLFWYVQHP NKGLQLLLKW FWGDTLVKGI    60
NGFEAEFKKS ETSFHLTKPS AHMSDAAEYF CVVGAPHRND KIIFGKGTRL HILP        114

SEQ ID NO: 110          moltype = AA   length = 114
FEATURE                 Location/Qualifiers
source                  1..114
                        mol_type = protein
                        organism = synthetic construct
SEQUENCE: 110
AQSVTQLDSH VSVSEGTPVL LRCNYSSSYS PSLFWYVQHP NKGLQLLLKY NGLKTLVKGI    60
NGFEAEFKKS ETSFHLTKPS AHMSDAAEYF CVVGAPHRND KIIFGKGTRL HILP        114

SEQ ID NO: 111          moltype = AA   length = 114
FEATURE                 Location/Qualifiers
source                  1..114
                        mol_type = protein
                        organism = synthetic construct
SEQUENCE: 111
AQSVTQLDSH VSVSEGTPVL LRCNYSSSYS PSLFWYVQHP NKGLQLLLKY TWGATLVKGI    60
NGFEAEFKKS ETSFHLTKPS AHMSDAAEYF CVVGAPHRND KIIFGKGTRL HILP        114

SEQ ID NO: 112          moltype = AA   length = 117
FEATURE                 Location/Qualifiers
source                  1..117
                        mol_type = protein
                        organism = synthetic construct
SEQUENCE: 112
DSGVTQTPKH LITATGQRVT LRCSPRSGDL SVYWYQQSLD QGLQFLIQYY NGWEAQKGNI    60
LERFSAQQFP DLHSELNLSS LELGDSALYF CASSVWSSGG ASAGELFFGE GSRLTVL     117

SEQ ID NO: 113          moltype = AA   length = 117
FEATURE                 Location/Qualifiers
source                  1..117
                        mol_type = protein
                        organism = synthetic construct
SEQUENCE: 113
DSGVTQTPKH LITATGQRVT LRCSPRSGDL SVYWYQQSLD QGLQFLIQYY NGEERAKGNI    60
LERFSAQQFP DLHSELNLSS LELGDSALYF CASSHWAVGG ASAGELFFGE GSRLTVL     117

SEQ ID NO: 114          moltype = AA   length = 117
FEATURE                 Location/Qualifiers
source                  1..117
                        mol_type = protein
                        organism = synthetic construct
SEQUENCE: 114
DSGVTQTPKH LITATGQRVT LRCSPRSGDL SVYWYQQSLD QGLQFLIQYY NGEERAKGNI    60
LERFSAQQFP DLHSELNLSS LELGDSALYF CASSVWSNGG ASSGNLSFGE GSRLTVL     117

SEQ ID NO: 115          moltype = AA   length = 117
FEATURE                 Location/Qualifiers
source                  1..117
                        mol_type = protein
                        organism = synthetic construct
SEQUENCE: 115
DSGVTQTPKH LITATGQRVT LRCSPRSGDL SVYWYQQSLD QGLQFLIKYY NGEEQAKGNI    60
LERFSAQQFP DLHSELNLSS LELGDSALYF CASSLWSSGG ASAGELSFGE GSRLTVL     117

SEQ ID NO: 116          moltype = AA   length = 117
FEATURE                 Location/Qualifiers
source                  1..117
```

```
                        mol_type = protein
                        organism = synthetic construct
SEQUENCE: 116
DSGVTQTPKH LITATGQRVT LRCSPRSGDL SVYWYQQSLD QGLQFLIQYY NGAELAKGNI    60
LERFSAQQFP DLHSELNLSS LELGDSALYF CASSVWSFGG ASAGELLFGE GSRLTVL      117

SEQ ID NO: 117          moltype = AA  length = 117
FEATURE                 Location/Qualifiers
source                  1..117
                        mol_type = protein
                        organism = synthetic construct
SEQUENCE: 117
DSGVTQTPKH LITATGQRVT LRCSPRSGDL SVYWYQQSLD QGLQFLIKYY NGEESAKGNI    60
LERFSAQQFP DLHSELNLSS LELGDSALYF CASSMWSFGG ASAGELLFGE GSRLTVL      117

SEQ ID NO: 118          moltype = AA  length = 114
FEATURE                 Location/Qualifiers
source                  1..114
                        mol_type = protein
                        organism = synthetic construct
SEQUENCE: 118
AQSVTQLDSH VSVSEGTPVL LRCNYSSSYS PSLFWYVQHP NKGLQLLLKY IGLGTLVKGI    60
NGFEAEFKKS ETSFHLTKPS AHMSDAAEYF CVVGAPHRND KIIFGKGTRL HILP         114

SEQ ID NO: 119          moltype = AA  length = 114
FEATURE                 Location/Qualifiers
source                  1..114
                        mol_type = protein
                        organism = synthetic construct
SEQUENCE: 119
AQSVTQLDSH VSVSEGTPVL LRCNYSSSYS PSLFWYVQHP NKGLQLLLKY IGLNTLVKGI    60
NGFEAEFKKS ETSFHLTKPS AHMSDAAEYF CVVGAPHRND KIIFGKGTRL HILP         114

SEQ ID NO: 120          moltype = AA  length = 117
FEATURE                 Location/Qualifiers
source                  1..117
                        mol_type = protein
                        organism = synthetic construct
SEQUENCE: 120
DSGVTQTPKH LITATGQRVT LRCSPRSGDL SVYWYQQSLD QGLQFLIQYY NGGELAKGNI    60
LERFSAQQFP DLHSELNLSS LELGDSALYF CASSVWSYGG ASAGELFFGE GSRLTVL      117

SEQ ID NO: 121          moltype = AA  length = 117
FEATURE                 Location/Qualifiers
source                  1..117
                        mol_type = protein
                        organism = synthetic construct
SEQUENCE: 121
DSGVTQTPKH LITATGQRVT LRCSPRSGDL SVYWYQQSLD QGLQFLNQYY NGVELAKGNI    60
LERFSAQQFP DLHSELNLSS LELGDSALYF CASSVWSFGG ASAGELFFGE GSRLTVL      117

SEQ ID NO: 122          moltype =     length =
SEQUENCE: 122
000

SEQ ID NO: 123          moltype = AA  length = 117
FEATURE                 Location/Qualifiers
source                  1..117
                        mol_type = protein
                        organism = synthetic construct
SEQUENCE: 123
DSGVTQTPKH LITATGQRVT LRCSPRSGDL SVYWYQQSLD QGLQFLIQYY NGEELAKGNI    60
LERFSAQQFP DLHSELNLSS LELGDSALYF CASSVWSFGG ASSGNLSFGE GSRLTVL      117

SEQ ID NO: 124          moltype = AA  length = 117
FEATURE                 Location/Qualifiers
source                  1..117
                        mol_type = protein
                        organism = synthetic construct
SEQUENCE: 124
DSGVTQTPKH LITATGQRVT LRCSPRSGDL SVYWYQQSLD QGLQFLIKYY NGEEQAKGNI    60
LERFSAQQFP DLHSELNLSS LELGDSALYF CASSVWSNGG ASSGNLSFGE GSRLTVL      117

SEQ ID NO: 125          moltype =     length =
SEQUENCE: 125
000

SEQ ID NO: 126          moltype =     length =
SEQUENCE: 126
```

```
000

SEQ ID NO: 127        moltype =    length =
SEQUENCE: 127
000

SEQ ID NO: 128        moltype = AA   length = 16
FEATURE               Location/Qualifiers
source                1..16
                      mol_type = protein
                      organism = synthetic construct
VARIANT               1..3
                      note = X can be any amino acid
VARIANT               4
                      note = X can be V or I
VARIANT               7
                      note = X can be S or I or N
VARIANT               9..10
                      note = X can be any amino acid
VARIANT               12
                      note = X can be A or S
VARIANT               13..16
                      note = X can be any amino acid
SEQUENCE: 128
XXXXWSXGXX SXXXXX                                                          16

SEQ ID NO: 129        moltype =    length =
SEQUENCE: 129
000

SEQ ID NO: 130        moltype =    length =
SEQUENCE: 130
000

SEQ ID NO: 131        moltype =    length =
SEQUENCE: 131
000

SEQ ID NO: 132        moltype = AA   length = 8
FEATURE               Location/Qualifiers
source                1..8
                      mol_type = protein
                      organism = synthetic construct
VARIANT               1
                      note = X can be Y or W or F
VARIANT               6
                      note = X can be T or S
VARIANT               7
                      note = X can be L or I or V
VARIANT               8
                      note = X can be V or I or L
SEQUENCE: 132
XIGNVXXX                                                                    8

SEQ ID NO: 133        moltype =    length =
SEQUENCE: 133
000

SEQ ID NO: 134        moltype =    length =
SEQUENCE: 134
000

SEQ ID NO: 135        moltype = AA   length = 12
FEATURE               Location/Qualifiers
source                1..12
                      mol_type = protein
                      organism = synthetic construct
VARIANT               1..2
                      note = X can be V or I or L
VARIANT               4
                      note = X can be A or G
VARIANT               9
                      note = X can be D or E
VARIANT               10
                      note = X can be K or R or H
VARIANT               11..12
                      note = X can be I or V or L
SEQUENCE: 135
XXGXPHHNXX XX                                                              12
```

| | | |
|---|---|---|
| SEQ ID NO: 136 | moltype = length = | |
| SEQUENCE: 136 | | |
| 000 | | |
| | | |
| SEQ ID NO: 137 | moltype = length = | |
| SEQUENCE: 137 | | |
| 000 | | |
| | | |
| SEQ ID NO: 138 | moltype = length = | |
| SEQUENCE: 138 | | |
| 000 | | |
| | | |
| SEQ ID NO: 139 | moltype = AA   length = 16 | |
| FEATURE | Location/Qualifiers | |
| source | 1..16 | |
| | mol_type = protein | |
| | organism = synthetic construct | |
| VARIANT | 1..3 | |
| | note = X can be any amino acid | |
| VARIANT | 4 | |
| | note = X can be V or I | |
| VARIANT | 7 | |
| | note = X can be S or I or N | |
| VARIANT | 9..10 | |
| | note = X can be any amino acid | |
| VARIANT | 12 | |
| | note = X can be A or S | |
| VARIANT | 13 | |
| | note = X can be any amino acid | |
| VARIANT | 14 | |
| | note = X can be E or N | |
| VARIANT | 15 | |
| | note = X can be any amino acid | |
| VARIANT | 16 | |
| | note = X can be F or S | |
| SEQUENCE: 139 | | |
| XXXXWSXGXX SXXXXX | | 16 |
| | | |
| SEQ ID NO: 140 | moltype = AA   length = 16 | |
| FEATURE | Location/Qualifiers | |
| source | 1..16 | |
| | mol_type = protein | |
| | organism = synthetic construct | |
| VARIANT | 1 | |
| | note = X can be A or G | |
| VARIANT | 2..3 | |
| | note = X can be S or T | |
| VARIANT | 4 | |
| | note = X can be V or I | |
| VARIANT | 7 | |
| | note = X can be S or I or N | |
| VARIANT | 9 | |
| | note = X can be G or A | |
| VARIANT | 10 | |
| | note = X can be A or G | |
| VARIANT | 12 | |
| | note = X can be A or S | |
| VARIANT | 13 | |
| | note = X can be G or A | |
| VARIANT | 14 | |
| | note = X can be E or N | |
| VARIANT | 15 | |
| | note = X can be L or I or V | |
| VARIANT | 16 | |
| | note = X can be F or S | |
| SEQUENCE: 140 | | |
| XXXXWSXGXX SXXXXX | | 16 |
| | | |
| SEQ ID NO: 141 | moltype = AA   length = 16 | |
| FEATURE | Location/Qualifiers | |
| source | 1..16 | |
| | mol_type = protein | |
| | organism = synthetic construct | |
| VARIANT | 1 | |
| | note = X can be A or G | |
| VARIANT | 2..3 | |
| | note = X can be S or T | |
| VARIANT | 9 | |

| | | |
|---|---|---|
| VARIANT | note = X can be G or A<br>10 | |
| VARIANT | note = X can be A or G<br>13 | |
| VARIANT | note = X can be G or A<br>15 | |
| | note = X can be L or I or V | |
| SEQUENCE: 141 | | |
| XXXIWSIGXX SSXNXS | | 16 |

BINDING MOLECULES

REFERENCE TO THE ELECTRONIC SEQUENCE LISTING

The application contains a Sequence Listing which has been submitted electronically in .XML format and is hereby incorporated by reference in its entirety. Said .XML copy, created on Jan. 5, 2024, is named "0282-0005US1-Seq-List.xml" and is 138,185 bytes in size. The sequence listing contained in this .XML file is part of the specification and is hereby incorporated by reference herein in its entirety.

FIELD OF THE INVENTION

The present invention relates to binding molecules that comprise T cell receptor (TCR) variable domains and which can bind to a PRAME peptide-HLA complex. The invention also relates to the use of such molecules for the treatment of malignant diseases.

BACKGROUND TO THE INVENTION

T cell receptors (TCRs) are naturally expressed by $CD4^+$ and $CD8^+$ T cells. TCRs are designed to recognize short peptide antigens that are displayed on the surface of antigen presenting cells in complex with Major Histocompatibility Complex (MHC) molecules (in humans, MHC molecules are also known as Human Leukocyte Antigens, or HLA) (Davis et al., Annu Rev Immunol. 1998; 16:523-44). $CD8^+$ T cells, which are also termed cytotoxic T cells, have TCRs that specifically recognize peptides bound to MHC class I molecules. $CD8^+$ T cells are generally responsible for finding and mediating the destruction of diseased cells, including cancerous and virally infected cells. The affinity of cancer-specific TCRs in the natural repertoire for their corresponding antigen is typically low as a result of thymic selection, meaning that cancerous cells frequently escape detection and destruction. Novel immunotherapeutic approaches aimed at promoting cancer recognition by T cells offer a highly promising strategy for the development of effective anticancer treatments.

PRAME or "Preferentially Expressed Antigen In Melanoma" was first identified as an antigen that is over expressed in melanoma (Ikeda et al Immunity. 1997 February; 6(2):199-208); it is also known as CT130, MAPE, OIP-4 and has Uniprot accession number P78395. The protein functions as a repressor of retinoic acid receptor signalling (Epping et al., Cell. 2005 Sep. 23; 122(6):835-47). PRAME belongs to the family of germline-encoded antigens known as cancer testis antigens. Cancer testis antigens are attractive targets for immunotherapeutic intervention since they typically have limited or no expression in normal adult tissues. PRAME is expressed in a number of solid tumours as well as in leukaemias and lymphomas (Doolan et al Breast Cancer Res Treat. 2008 May; 109(2): 359-65; Epping et al Cancer Res. 2006 Nov. 15; 66(22): 10639-42; Ercolak et al Breast Cancer Res Treat. 2008 May; 109(2): 359-65; Matsushita et al Leuk Lymphoma. 2003 March; 44(3):439-44; Mitsuhashi et al Int. J Hematol. 2014; 100(1):88-95; Proto-Sequeire et al Leuk Res. 2006 November; 30(11):1333-9; Szczepanski et al Oral Oncol. 2013 February; 49(2):144-51; Van Baren et al Br J Haematol. 1998 September; 102(5):1376-9). PRAME targeting therapies of the inventions may be particularly suitable for treatment of cancers including, but not limited to, melanoma (cutaneous and uveal), lung (NSCLC and SCLC), breast (including triple negative), ovarian, endometrial, oesophageal, bladder and head and neck cancers.

HLA-A24 is an HLA serotype where the alpha chains are encoded by the HLA-A*24 allele group and the beta chains are encoded by the beta-2-microglobulin locus. While there are over 90 known A*24 alleles, the HLA-A24 serotype is dominated by A*24:02. As such A*24:02 is often synonymously used with A*24. In this regard, "HLA-A24" is used herein synonymously with "HLA-A*24:02". The gene frequency of HLA-A24 (A*24:02) is different and relatively higher in certain populations as compared to the gene frequency of HLA-A2 (A*02:01).

The peptide PYLGQMINL (SEQ ID NO: 1) corresponds to amino acids 254-262 of the full length PRAME protein (UniProt id: P78395) and is presented on the cell surface in complex with HLA-A24 (i.e., "HLA-A*24:02", also referred to as "HLA-A*24"). This peptide-HLA complex provides a useful target for TCR-based immunotherapeutic intervention.

The identification of particular TCR sequences that bind to the PYLGQMINL (SEQ ID NO: 1) in complex with HLA-A24 complex with high affinity and high specificity is advantageous for the development of novel immunotherapies. Therapeutic TCRs may be used, for example, as soluble targeting agents for the purpose of delivering cytotoxic agents to the tumour site or activating immune effector functions against the tumour cells (Lissin, et al., "High-Affinity Monoclonal T-cell receptor (mTCR) Fusions" in Fusion Protein Technologies for Biophamaceuticals: Applications and Challenges. 2013. S. R. Schmidt, Wiley; Boulter et al., Protein Eng. 2003 September; 16(9):707-11; Liddy, et al., Nat Med. 2012 June; 18(6):980-7), or alternatively they may be used to engineer T cells for adoptive therapy (Fesnak et al., Nat Rev Cancer. 2016 Aug. 23; 16(9):566-81).

While TCRs that bind to PYLGQMINL (SEQ ID NO: 1) in complex with HLA-A24 have been reported previously (CN106699874 A and CN106831978 A), these TCRs were not engineered or characterized for use as therapeutic TCRs. As explained further herein, the production of a TCR engineered to have high affinity particularly when balanced with other desirable features is not straightforward, and typically has a high attrition rate.

There is therefore a need for binding molecules, such as TCRs, capable of binding with high affinity and specificity to PYLGQMINL (SEQ ID NO: 1) in complex with HLA-A24 for the development of new immunotherapies.

In the first instance, the skilled person needs to identify a suitable starting, or scaffold, sequence. Typically such sequences may be obtained from natural sources e.g. from antigen responding T cells extracted from donor blood. Given the rarity of cancer specific T cells in the natural repertoire, it is often necessary to screen many donors, for example 20 or more, before a responding T cell may be found. The screening process may take several weeks or months, and even where a responding T cell is found, it may be unsuitable for immunotherapeutic use. For example, the response may be too weak and/or may not be specific for the target antigen. Alternatively, it may not be possible to generate a clonal T cell population, nor expand or maintain a given T cell line to produce sufficient material to identify the correct TCR chain sequences. TCR sequences that are suitable as starting, or scaffold, sequences should have one or more of the following properties: a good affinity for the target peptide-HLA complex, for example 200 µM or stronger; a high level of target specificity, e.g. relatively weak or no binding to alternative peptide-HLA complexes; be amenable to use in display libraries, such as phage display; be able to be refolded and purified at high yield; and maintain stability in purified form. Given the degenerate nature of TCR recognition, it is exceptionally hard even for skilled practitioners to be able to determine whether a particular scaffold TCR sequence has a specificity profile that would make it eligible for engineering for therapeutic use (Wooldridge, et al., J Biol Chem. 2012 Jan. 6; 287(2):1168-77).

The next challenge is to engineer the TCR to have a higher affinity towards the target antigen whilst retaining desirable characteristics such as specificity and yield. TCRs, as they exist in nature, have weak affinity for target antigen (low micromolar range) compared with antibodies, and TCRs against cancer antigens typically have weaker antigen recognition than viral specific TCRs (Aleksic, et al. Eur J Immunol. 2012 December; 42(12):3174-9). This weak affinity coupled with HLA down-regulation on cancer cells means that therapeutic TCRs for cancer immunotherapy typically require engineering to increase their affinity for target antigen and thus generate a more potent response. Such affinity increases are essential for soluble TCR-based reagents. In such cases, antigen-binding affinities in the nanomolar to picomolar range, with binding half-lives of several hours, are desirable. The improved potency generated by high affinity antigen recognition at low epitope numbers is exemplified in FIGS. 1e and 1f of Liddy et al. (Liddy, et al., Nat Med. 2012 June; 18(6):980-7). The affinity maturation process, typically involves the skilled person having to engineer specific mutations and/or combinations of mutations, including but not limited to substitutions, insertions and/or deletions, on to the starting TCR sequence in order to increase the strength of antigen recognition. Affinity maturation techniques are known in the art, for example the use of display libraries (Li et al., Nat Biotechnol. 2005 March; 23(3):349-54; Holler et al., Proc Natl Acad Sci USA. 2000 May 9; 97(10):5387-92). However, to produce significant increases in the affinity of a given TCR against a given target, the skilled person may have to engineer combinations of mutations from a large pool of possible alternatives. The specific mutations that produce significant increases in affinity are not predictable and there is a high attrition rate. In many cases, it may not be possible to achieve significant increases in affinity with a given TCR starting sequence.

The affinity maturation process must also take account of the necessity of maintaining TCR antigen specificity. Increasing the affinity of a TCR for its target antigen brings a substantial risk of revealing cross reactivity with other unintended targets as a result of the inherent degeneracy of TCR antigen recognition (Wooldridge, et al., J Biol Chem. 2012 Jan. 6; 287(2):1168-77; Wilson, et al., Mol Immunol. 2004 February; 40(14-15):1047-55; Zhao et al., J Immunol. 2007 Nov. 1; 179(9):5845-54). At a natural level of affinity the recognition of the cross reactive antigen may be too low to produce a response. If a cross reactive antigen is displayed on normal healthy cells, there is a strong possibility of off-target binding in vivo which may manifest in clinical toxicity. Thus, in addition to increasing antigen binding strength, the skilled person must also engineer mutations and or combinations of mutations that allow the TCR to retain a high specificity for target antigen and demonstrate a good safety profile in preclinical testing. Again, suitable mutations and/or combinations of mutations are not predictable. The attrition rate at this stage is even higher and in many cases may not be achievable at all from a given TCR starting sequence.

DESCRIPTION OF THE INVENTION

As described further below, the present invention provides, for the first time, binding molecules comprising a TCR that are suitable for immunotherapeutic use against tumour cells that are positive for PRAME and HLA-A24. Many of the TCR immunotherapies currently in development target cells positive for HLA-A2; thus, the present invention expands the application of TCR therapies, and provides the potential to treat different patient populations that would otherwise not benefit from therapies targeting HLA-A2 tumour cells. Also, as described further below, the identification of the binding molecule of the present invention required extensive engineering efforts, none of which were straightforward, with over a dozen TCR affinity maturation series explored. Even once a particular affinity maturation series was selected for further study, additional multiple rounds of affinity maturation and removal of risky deamidation residues were performed. Subsequently, further stability enhancements were engineered into the molecule, all of which were introduced while maintaining the appropriate potency and affinity. These stability enhancements are advantageous for a TCR to be capable of use in vivo, particularly in a patient, and are also critical for such a TCR to be manufactured for such use.

Binding Molecules

In a first aspect, the present invention provides a binding molecule comprising a TCR alpha chain variable domain and a TCR beta chain variable domain, wherein the binding molecule has the property of binding to PYLGQMINL (SEQ ID NO: 1) in complex with HLA-A24, wherein each of the alpha chain variable domain and the beta chain variable domain comprises FR1-CDR1-FR2-CDR2-FR3-CDR3-FR4, where FR is a framework region and CDR is a complementarity determining region, wherein (a) the binding molecule contacts residues P1, Q5, I7 and N8 of the PYLGQMINL (SEQ ID NO: 1) peptide when the binding molecule is bound to PYLGQMINL (SEQ ID NO: 1) in complex with HLA-A24; and/or (b) the alpha chain CDR3 comprises the sequence X-X-X-X-P-N/H-R/H-X-X-X-X-X (SEQ ID NO: 125),
the beta chain CDR1 comprises the sequence X-X-X-L/Y-X (SEQ ID NO: 126),
the beta chain CDR2 comprises the sequence X-Y-X-X-X-X (SEQ ID NO: 127), and
the beta chain CDR3 comprises the sequence X-X-X-V/I-W-S-S/I/N-G-X-X-S-A/S-X-X-X-X (SEQ ID NO: 128),
where X is any amino acid.

SEQ ID NOs: 125-128 referred to above are consensus sequences based on the inventors' identification of key CDR residues that contact the target peptide when the binding molecule is bound to PYLGQMINL (SEQ ID NO: 1) in complex with HLA-A24, as described in Example 7. The sequences are shown in the section below entitled "Description of the sequences".

The inventors have surprisingly identified binding molecules, comprising TCR variable domains, with a particularly high affinity (picomolar range), and a high degree of antigen specificity for the PYLGQMINL (SEQ ID NO: 1)-HLA-A24 complex, despite the difficulties described above. Said molecules demonstrate potent killing of PRAME positive cancer cells when prepared as soluble reagents fused to a T cell redirecting moiety. The molecules of the invention thus have a particularly suitable profile for therapeutic use. Particular binding molecules of the invention were engineered from a suitable scaffold (e.g., "wild-type") TCR sequence into which a number of mutations were introduced to enhance affinity and/or stability, while maintaining high specificity.

In a second aspect, the present invention provides a binding molecule comprising a TCR alpha chain variable domain and a TCR beta chain variable domain, wherein the binding molecule has the property of binding to PYLGQMINL (SEQ ID NO: 1) in complex with HLA-A24, wherein each of the alpha chain variable domain and the beta chain variable domain comprises FR1-CDR1-FR2-CDR2-FR3-CDR3-FR4, where FR is a framework region and CDR is a complementarity determining region, wherein
  (a) the alpha chain CDRs have the following sequences:
    CDR1—SSYSPS (SEQ ID NO: 5), optionally with one, two or three mutations therein,
    CDR2—YIGNVTLV (SEQ ID NO: 27), optionally with one, two, three or four mutations therein,
    CDR3—VVGAPHHNDKII (SEQ ID NO: 30), optionally with one, two, three or four mutations therein,
and/or
  (b) the beta chain CDRs have the following sequences:
    CDR1—SGDYS (SEQ ID NO: 32), optionally with one, two or three mutations therein,
    CDR2—YYNAEE (SEQ ID NO: 35), optionally with one, two or three mutations therein,
    CDR3—ASSIWSIGGASSGNLS (SEQ ID NO: 41), optionally with one, two, three, four or five mutations therein.

In a third aspect, the present invention provides a binding molecule comprising a TCR alpha chain variable domain and a TCR beta chain variable domain, wherein the binding molecule has the property of binding to PYLGQMINL (SEQ ID NO: 1) in complex with HLA-A24, wherein each of the alpha chain variable domain and the beta chain variable domain comprises FR1-CDR1-FR2-CDR2-FR3-CDR3-FR4, where FR is a framework region and CDR is a complementarity determining region, wherein
  (a) the alpha chain CDRs have the following sequences:
    CDR1—SSYSPS (SEQ ID NO: 5), optionally with one, two or three mutations therein,
    CDR2—YTSAATLV (SEQ ID NO: 6), optionally with one, two, three or four mutations therein,
    CDR3—VVSAPNRDDKII (SEQ ID NO: 7), optionally with one, two, three or four mutations therein,
and/or
  (b) the beta chain CDRs have the following sequences:
    CDR1—SGDLS (SEQ ID NO: 15), optionally with one, two or three mutations therein,
    CDR2—YYNGEE (SEQ ID NO: 16), optionally with one, two or three mutations therein,
    CDR3—ASSVWSSGGASAGELF (SEQ ID NO: 17), optionally with one, two, three, four or five mutations therein.

In a fourth aspect, the present invention provides a binding molecule that specifically binds to a PYLGQMINL (SEQ ID NO: 1)-HLA-A24 complex, wherein the binding molecule comprises a TCR alpha chain variable domain and a TCR beta chain variable domain, wherein each variable domain comprises three complementarity determining regions designated CDR1, CDR2, and CDR3 wherein
  (a) the binding molecule contacts residues P1, Q5, I7 and N8 of the PYLGQMINL (SEQ ID NO: 1) peptide when the binding molecule is bound to the PYLGQMINL (SEQ ID NO: 1)-HLA-A24 complex; and/or
  (b) the alpha chain CDR3 comprises X-X-X-X-P-N/H-R/H-X-X-X-X-X (SEQ ID NO: 125),
    the beta chain CDR1 comprises X-X-X-L/Y-X (SEQ ID NO: 126),
    the beta chain CDR2 comprises X-Y-X-X-X-X (SEQ ID NO: 127); and
    the beta chain CDR3 comprises X-X-X-V/I-W-S-S/I/N-G-X-X-S-A/S-X-X-X-X-X (SEQ ID NO: 128);
    where X is any amino acid References herein to "the binding molecule" or "the binding molecule of the invention" are in relation to each of the binding molecules of the first, second, third and fourth aspects above, unless clearly indicated otherwise.

As used herein, the term "binding molecule" generally refers to a molecule capable of binding to a target antigen. The binding molecules of the invention comprise a TCR alpha chain variable domain and a TCR beta chain variable domain, which associate together to form a TCR binding site which is capable of binding to the PYLGQMINL (SEQ ID NO: 1)-HLA-A24 complex. As used herein, the phrase "binding to the PYLGQMINL (SEQ ID NO: 1)-HLA-A24 complex" is used interchangeably with "binding to PYLGQMINL (SEQ ID NO: 1) in complex with HLA-A24". The binding molecules of the invention may adopt a number of different formats as discussed herein. Furthermore, fragments of the binding molecules of the invention are also envisioned. A fragment refers to a portion of the binding molecule that retains binding to the target antigen.

The binding molecules of the invention comprise TCR variable domains, which may correspond to those from a native TCR, or more preferably the TCR variable domains may be engineered (i.e., contain mutations relative to the native sequence). Native TCR variable domains may also be referred to as wild-type, natural, parental, unmutated or scaffold domains. The binding molecules may have ideal therapeutic properties such as supra-physiological affinity for target, long binding half-life, high specificity for target and good stability. The invention also includes multispecific (e.g., bispecific), or multifunctional (e.g., bifunctional), or fusion, molecules that incorporate TCR variable domains described herein and, for example, a T cell redirecting moiety. Such molecules can mediate a potent and specific response against PRAME positive cancer cells by re-directing and activating T-cells. Furthermore, the use of binding molecules with supra-physiological affinity facilitates recognition of such cancer cells presenting low levels of the target peptide-HLA complex. Alternatively, the binding molecules may further comprise (e.g., by fusion) other therapeutic agents, and or diagnostic agents, and or incorporated in to engineered T cells for adoptive therapy.

The binding molecule may comprise or consist of a TCR comprising the TCR alpha chain variable domain and the TCR beta chain variable domain. The TCR may be a soluble TCR, i.e., a TCR that does not comprise a transmembrane domain and does not comprise an intracellular/cytoplasmic domain. The TCR domain sequences may be defined with reference to IMGT nomenclature which is widely known and accessible to those working in the TCR field. For example, see: LeFranc and LeFranc, (2001). "T cell Receptor Factsbook", Academic Press; Lefranc, (2011), Cold Spring Harb Protoc 2011(6): 595-603; Lefranc, (2001), Curr Protoc Immunol Appendix 1: Appendix 1O; and Lefranc, (2003), Leukemia 17(1): 260-266. Briefly, αβ TCRs consist of two disulphide linked chains. Each chain (alpha and beta) is generally regarded as having two domains, namely a variable and a constant domain. A short joining region connects the variable and constant domains and is typically considered part of the alpha variable region. Additionally, the beta chain usually contains a short diversity region next to the joining region, which is also typically considered part of the beta variable region. The variable domain of each chain is located N-terminally and comprises three Complementarity Determining Regions (CDRs) embedded in a framework sequence (FR). The CDRs comprise the recognition site for peptide-MHC binding. There are several genes coding for alpha chain variable (Vα) regions and several genes coding for beta chain variable (Vβ) regions, which are distinguished by their framework, CDR1 and CDR2 sequences, and by a partly defined CDR3 sequence. The Vα and Vβ genes are referred to in IMGT nomenclature by the prefix TRAV and TRBV respectively (Folch and Lefranc, (2000), Exp Clin Immunogenet 17(1): 42-54; Scaviner and Lefranc, (2000), Exp Clin Immunogenet 17(2): 83-96; LeFranc and LeFranc, (2001), "T cell Receptor Factsbook", Academic Press). Likewise there are several joining or J genes, termed TRAJ or TRBJ, for the alpha and beta chain respectively, and for the beta chain, a diversity or D gene termed TRBD (Folch and Lefranc, (2000), Exp Clin Immunogenet 17(2): 107-114; Scaviner and Lefranc, (2000), Exp Clin Immunogenet 17(2): 97-106; LeFranc and LeFranc, (2001), "T cell Receptor Factsbook", Academic Press). The huge diversity of T cell receptor chains results from combinatorial rearrangements between the various V, J and D genes, which include allelic variants, and junctional diversity (Arstila, et al., (1999), Science 286(5441): 958-961; Robins et al., (2009), Blood 114(19): 4099-4107.) The constant, or C, regions of TCR alpha and beta chains are referred to as TRAC and TRBC respectively (Lefranc, (2001), Curr Protoc Immunol Appendix 1: Appendix 10).

Certain binding molecules of the invention preferably have a $K_D$ for the PYLGQMINL (SEQ ID NO: 1)-HLA-A24 complex of greater than (i.e. stronger than) the native TCR (also referred to as the non-mutated, or scaffold TCR). The $K_D$ may be, for example, in the range of 1 pM to 50 μM. Binding molecules of the invention may have a $K_D$ for the target complex of from about (i.e. +/−10%) 1 pM to about 400 nM, from about 1 pM to about 1000 pM, from about 1 pM to about 500 pM or from about 1 pM to about 100 pM. Said binding molecules may additionally, or alternatively, have a binding half-life (T½) for the complex in the range of from about 0.5 min to about 50 h, from about 20 min to about 30 h, or from about 20 min to about 25 h. Preferably, binding molecules of the invention have a $K_D$ for the PYLGQMINL (SEQ ID NO: 1)-HLA-A24 complex of from about 1 pM to about 500 pM and/or a binding half-life from about 20 min to about 25 h. Such high-affinity is preferable for binding molecules in soluble format when associated with therapeutic agents and/or detectable labels. The affinity of a binding molecule may be measured at 25° C. Methods for determining affinity of binding molecules are described herein.

Binding molecules of the invention comprising native TCR variable domains may have a $K_D$ for the complex of from about 1 μM to about 200 μM, or from about 1 μM to about 100 μM. Such binding molecules may be preferable for adoptive therapy applications.

As described in the Examples herein below, the methionine at position 6 of the PYLGQMINL (SEQ ID NO: 1) peptide can be presented in oxidised or reduced form. The inventors detected both forms on cancer cell lines and in tumour tissue. The TCRs of the invention may bind to both forms. Binding affinity of a binding molecule of the invention may be assessed using either form. Binding to the reduced from of PYLGQMINL (SEQ ID NO: 1) may be stronger. Thus, binding affinity of a binding molecule of the invention may be assessed using the reduced form of PYLGQMINL (SEQ ID NO: 1) in complex with HLA-A24.

Certain preferred mutated binding molecules have a binding affinity for, and/or a binding half-life for, the PYLGQMINL (SEQ ID NO: 1)-HLA-A24 complex that is substantially higher than that of the native TCR. Increasing the binding affinity of a native TCR may reduce the specificity of the TCR for its peptide-MHC ligand, and this is demonstrated in Zhao et al., (2007) J. Immunol, 179:9, 5845-5854. However, the binding molecules of the invention surprisingly demonstrate a high level of specificity for the PYLGQMINL (SEQ ID NO: 1)-HLA-A24 complex, despite having substantially higher binding affinity than the native TCR.

The binding molecules of the invention preferably have the property of specifically binding to the PYLGQMINL (SEQ ID NO: 1)-HLA-A24 complex. As used herein, "specific" binding refers to a binding molecule that binds to the PYLGQMINL (SEQ ID NO: 1)-HLA-A24 complex with higher affinity than to other peptide-HLA complexes. Highly specific binding molecules of the invention are particularly suitable for therapeutic use due to the reduced risk of off-target effects. Specificity in the context of binding molecules of the invention can be determined according to their ability to recognise target cells that are antigen positive, whilst having minimal ability to recognise target cells that are antigen negative, and/or to bind to peptides that are similar in sequence to the target peptide but differ by up to three amino acids.

Specificity can be measured in vitro, for example, in cellular assays, such as ELISpot assays, such as those described in Examples 3, 5 and 6. To test specificity, the binding molecules may be in soluble form and associated with an immune effector, and/or may be expressed on the surface of cells, such as T cells. Specificity may be determined by measuring the level of T cell activation in the presence of antigen positive and antigen negative target cells as defined above. Minimal recognition of antigen negative target cells is defined as a level of T cell activation of less than 20%, preferably less than 10%, preferably less than 5%, and more preferably less than 1%, of the level produced in the presence of antigen positive target cells, when measured under the same conditions (i.e. using the same lots of target and effector cells) and at a therapeutically relevant TCR concentration. For soluble TCRs associated with an immune effector, a therapeutically relevant concentration may be defined as a concentration of $10^{-9}$ M or below, and/or a concentration of up to 100, preferably up to 1000, fold greater than the corresponding EC50 or IC50 value. Preferably, for soluble binding molecules associated with an immune effector there is at least a 10 fold difference, at least a 100 fold, at least 1000 fold, at least 10000 fold difference in EC50 or IC50 value between T cell activation against antigen positive cells relative to antigen negative cells—this difference may be referred to as a therapeutic window. Additionally or alternatively the therapeutic window may be calculated based on lowest effective concentrations ("LOEL") observed for normal cells and an infected cell. Antigen positive cells may be obtained by peptide-pulsing using a suitable peptide concentration to obtain a level of antigen presentation comparable to wt peptide presentation, or, they may naturally present said peptide. Preferably, both antigen positive and antigen negative cells are human cells.

Specificity may additionally, or alternatively, relate to the ability of a binding molecule to bind to the PYLGQMINL (SEQ ID NO: 1)-HLA-A24 complex and not to a panel of alternative peptide-HLA complexes. This may, for example, be determined by the Surface Plasmon Resonance (SPR) method described in Examples 1. Said panel may contain at least 2, at least 3, at least 5, or at least 10, alternative peptide-HLA complexes. The alternative peptides may share a low level of sequence identity with SEQ ID NO: 1 and may be naturally or artificially presented. Alternative peptides are preferably derived from commonly expressed proteins and or proteins expressed in healthy human tissues. Specific binding of the binding molecule to the PYLGQMINL (SEQ ID NO: 1)-HLA-A24 complex may be at least 2 fold greater than to other naturally or artificially-presented peptide HLA complexes, more preferably at least 10 fold, or at least 50 fold or at least 100 fold greater, even more preferably at least 1000 fold greater. Natural variants of PYLGQMINL (SEQ ID NO: 1) peptide may be excluded from the definition of alternative peptide-HLA complexes.

An alternative or additional approach to determine binding molecule specificity may be to identify the peptide recognition motif of the binding molecule using sequential mutagenesis, e.g. alanine scanning, of the target peptide. Residues that form part of the binding motif are those that are not permissible to substitution. Non-permissible substitutions may be defined as those peptide positions in which the binding affinity of the binding molecule is reduced by at least 50%, or preferably at least 80% relative to the binding affinity for the non-mutated peptide. Such an approach is further described in Cameron et al., (2013), Sci Transl Med. 2013 Aug. 7; 5 (197): 197ra103 and WO2014096803. Binding molecule specificity in this case may be determined by identifying alternative motif containing peptides, particularly alternative motif containing peptides in the human proteome, and testing these peptides for binding to the binding molecule. Binding of the binding molecule to one or more alternative peptides may indicate a lack of specificity. In this case further testing of binding molecule specificity via cellular assays may be required. A low tolerance for (alanine) substitutions in the central part of the peptide indicate that the TCR has a high specificity and therefore presents a low risk for cross-reactivity with alternative peptides.

A binding molecule having the property of specifically binding to the PYLGQMINL (SEQ ID NO: 1)-HLA-A24 complex may bind to this complex with higher affinity relative to another peptide-HLA-A24 complex. The binding molecule may bind to the PYLGQMINL (SEQ ID NO: 1)-HLA-A24 complex with an affinity which is at least two-fold, at least five-fold, at least 10-fold, at least 100-fold, or at least 1000-fold higher than its affinity for a PYTGQQISL (SEQ ID NO: 81)-HLA-A24 complex and/or a PYLGQAPFL (SEQ ID NO: 82)-HLA-A24 complex and/or a PYLSTMINY (SEQ ID NO: 83)-HLA-A24 and/or a PYLGSKISL (SEQ ID NO: 84)-HLA-A24 complex. These alternative peptides are referred to as Mimetic 1 ("Mim1"), Mimetic 2 ("Mim2"), Mimetic 3 ("Mim3") and Mimetic 4 ("Mim4") respectively in Example 1 herein. The binding molecule may bind to the PYLGQMINL (SEQ ID NO: 1)-HLA-A24 complex with an affinity which is at least two-fold, at least five-fold, at least 10-fold, at least 100-fold, or at least 1000-fold higher than its affinity for a PYLGQAPFL (SEQ ID NO: 82)-HLA-A24 complex and/or a PYLGSKISL (SEQ ID NO: 84)-HLA-A24 complex.

Certain binding molecules of the invention are able to generate a highly potent T cell response in vitro against antigen positive cells, in particular those cells presenting low levels of antigen (i.e. in the order of 5-100). Such binding molecules may be in soluble form and linked to an immune effector such as an anti-CD3 antibody. The T cell response that is measured may be the release of T cell activation markers such as Interferon γ or Granzyme B, or target cell killing, or other measure of T cell activation, such as T cell proliferation. Preferably a highly potent response is one with $EC_{50}$ value in the pM range, i.e. 1000 pM or lower.

The term 'mutations' encompasses designed substitutions, insertions and deletions (e.g., engineered or designed substitutions, insertions and deletions). Mutations to a native (also referred to as parental, natural, unmutated, wild type, or scaffold) binding molecule may confer beneficial therapeutic properties, such as higher affinity, higher stability, higher specificity and/or high potency. For example, mutations may include those that increase the binding affinity ($K_D$) and/or binding half life (T½) of the binding molecule to the PYLGQMINL (SEQ ID NO: 1)-HLA-A24 complex.

The term "stability" in the context of the present invention refers to physical and chemical stability and can be evaluated qualitatively and/or quantitatively using various analytical techniques that are described in the art and are reviewed in for example Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993). Such methods include the evaluation of aggregate formation (for example using size exclusion chromatography (SEC)), by measuring turbidity (for example by dynamic light scattering (DLS) or light obscuration (LO)) and/or by visual inspection (for example by determining colour and clarity).

The binding molecule of the invention may contact at least 7, or at least 8, peptide residues when bound to PYLGQMINL (SEQ ID NO: 1) in complex with HLA-A24. A binding "contact", as used herein, is a reference to a (e.g., non-covalent) interaction between atoms from one molecule and atoms from another molecule when the two molecules are bound together. For example, a peptide residue binding "contact" is a binding interaction formed between amino acid residues of the PYLGQMINL (SEQ ID NO: 1) peptide, not the HLA, and amino acid residues of the binding molecule. The binding molecule, when bound to the PYLGQMINL (SEQ ID NO: 1) HLA-A24 complex, may contact at least residues P1, Q5, I7 and N8 of the PYLGQMINL (SEQ ID NO: 1) peptide. The binding molecule, when bound to the PYLGQMINL (SEQ ID NO: 1) HLA-A24 complex, may contact all of the peptide residues in positions 1 to 8 of the PYLGQMINL (SEQ ID NO: 1) peptide. Binding contacts can be identified using any method known in the art, including x-ray crystallography and structural modelling as described herein.

Certain angles can be used to define the binding geometry of the interaction between a binding molecule of the invention and the PYLGQMINL (SEQ ID NO: 1) HLA-A24 complex. For example, the binding molecule may bind to the PYLGQMINL (SEQ ID NO: 1) HLA-A24 complex with a crossing angle in the range of 35° to 55°, or preferably in the range of 38° to 48°. The binding molecule may bind to the PYLGQMINL (SEQ ID NO: 1) HLA-A24 complex with a tilt angle in the range of −10° to 10°, preferably in the range of −1° to 9°. The binding molecule may bind to the PYLGQMINL (SEQ ID NO: 1) HLA-A24 complex with a roll angle in the range of −10° to 10°, preferably in the range of −6° to 4°. Binding geometry of a binding molecule, such as crossing, tilt and roll angles, can be identified using any method known in the art, including x-ray crystallography and structural modelling as described herein. For example, methods of calculating these angles are described in Rudolph et al. (2006). Annu Rev Immunol. 24, 419-466.

In the binding molecules of the invention, there may be at least one mutation in the TCR alpha chain variable region. There may be one, two, three, four, five, six, seven, eight, nine, ten, or more, mutations in the alpha chain CDRs (i.e. in total across all three CDRs). For example, there may be 8 mutations in the alpha chain CDRs. There may be no mutations in the alpha chain CDR1 and/or four mutations in the alpha chain CDR2 and/or four mutations in the alpha chain CDR3

The binding molecule of the first aspect of the invention may comprise an alpha chain CDR3 comprising the sequence of any one of SEQ ID NOs: 125, 133, 134 or 135.

The binding molecule of the first aspect of the invention may comprise a beta chain CDR1 comprising the sequence of any one of SEQ ID NOs: 126, 136 or 137.

The binding molecule of the first aspect of the invention may comprise a beta chain CDR2 comprising the sequence of SEQ ID NO: 127 or SEQ ID NO: 138.

The binding molecule of the first aspect of the invention may comprise a beta chain CDR3 comprising the sequence of any one of SEQ ID NOs: 128, 139, 140 or 141.

The binding molecule of the first aspect of the invention may comprise
- an alpha chain CDR3 comprising the sequence X-X-S/G-X-P-N/H-R/H-D/N-X-X-X-X (SEQ ID NO: 133),
- a beta chain CDR1 comprising the sequence S/T-G/A-D/E-L/Y-S/T (SEQ ID NO: 136),
- a beta chain CDR2 comprising the sequence Y/W/F-Y-N/Q-G/A-E/D-E/D (SEQ ID NO: 138), and
- a beta chain CDR3 comprises the sequence X-X-X-V/I-W-S-S/I/N-G-X-X-S-A/S-X-E/N-X-F/S (SEQ ID NO: 139).

The binding molecule of the first aspect of the invention may comprise
- an alpha chain CDR3 comprising the sequence V/I/L-V/I/L-S/G-A/G-P-N/H-R/H-D/N-D/E-K/R/H-I/V/L-I/V/L (SEQ ID NO: 134),
- a beta chain CDR1 comprising the sequence S/T-G/A-D/E-L/Y-S/T (SEQ ID NO: 136),
- a beta chain CDR2 comprising the sequence Y/W/F-Y-N/Q-G/A-E/D-E/D (SEQ ID NO: 138), and
- a beta chain CDR3 comprises the sequence A/G-S/T-S/T-V/I-W-S-S/I/N-G-G/A-A/G-S-A/S-G/A-E/N-L/I/V-F/S (SEQ ID NO: 140).

The binding molecule of the first aspect of the invention may comprise
- an alpha chain CDR3 comprising the sequence V/I/L-V/I/L-G-A/G-P-H-H-N-D/E-K/R/H-I/V/L-I/V/L (SEQ ID NO: 135),
- a beta chain CDR1 comprising the sequence S/T-G/A-D/E-Y-S/T (SEQ ID NO: 137),
- a beta chain CDR2 comprising the sequence Y/W/F-Y-N/Q-G/A-E/D-E/D (SEQ ID NO: 138), and
- a beta chain CDR3 comprises the sequence A/G-S/T-S/T-I-W-S-I-G-G/A-A/G-S-S-G/A-N-L/I/V-S (SEQ ID NO: 141).

The binding molecule of the first aspect of the invention may comprise
- an alpha chain CDR1 comprising the sequence S/T-S/T-Y/W/F-S/T-P-S/T (SEQ ID NO: 130),
- an alpha chain CDR2 comprising the sequence Y/W/F-I-G-N-V-T/S-L/I/V-V/I/L (SEQ ID NO: 132),
- an alpha chain CDR3 comprising the sequence V/I/L-V/I/L-G-A/G-P-H-H-N-D/E-K/R/H-I/V/L-I/V/L (SEQ ID NO: 135),
- a beta chain CDR1 comprising the sequence S/T-G/A-D/E-Y-S/T (SEQ ID NO: 137),
- a beta chain CDR2 comprising the sequence Y/W/F-Y-N/Q-G/A-E/D-E/D (SEQ ID NO: 138), and
- a beta chain CDR3 comprises the sequence A/G-S/T-S/T-I-W-S-I-G-G/A-A/G-S-S-G/A-N-L/I/V-S (SEQ ID NO: 141).

The binding molecule of the first aspect of the invention may comprise
- an alpha chain CDR3 comprising the sequence of VVGAPHHNDKII (SEQ ID NO: 30), optionally with one, two, three or four mutations at any of positions 1~4 or 8-12 of SEQ ID NO: 30 (i.e. the mutations exclude P5, H6 and H7 numbered according to SEQ ID NO: 30);
- a beta chain CDR1 comprising the sequence of SGDYS (SEQ ID NO: 32), optionally with one, two or three mutations at any of positions 1-3 or 5 of SEQ ID NO: 32 (i.e. the mutations exclude Y5 numbered according to SEQ ID NO: 32);
- a beta chain CDR2 comprising the sequence of YYNAEE (SEQ ID NO: 35), optionally with one, two or three mutations at any of positions 1 or 3-6 of SEQ ID NO: 35 (i.e. the mutations exclude Y2 numbered according to SEQ ID NO: 35); and
- a beta chain CDR3 comprising the sequence of ASSIWSIGGASSGNLS (SEQ ID NO: 41), optionally with one, two, three, four or five mutations at any of positions 1-3, 9, 10 or 13-16 of SEQ ID NO: 41 (i.e. the mutations exclude I4, W5, S6, I7, G8, S11 and S12 numbered according to SEQ ID NO: 41).

The binding molecule of the first aspect of the invention may comprise
- an alpha chain CDR3 comprising the sequence of VVGAPHHNDKII (SEQ ID NO: 30), optionally with one, two, or three mutations at any of positions 1~4 or 8-12 of SEQ ID NO: 30 (i.e. the mutations exclude P5, H6 and H7 numbered according to SEQ ID NO: 30);
- a beta chain CDR1 comprising the sequence of SGDYS (SEQ ID NO: 32), optionally with one or two mutations at any of positions 1-3 or 5 of SEQ ID NO: 32 (i.e. the mutations exclude Y5 numbered according to SEQ ID NO: 32);
- a beta chain CDR2 comprising the sequence of YYNAEE (SEQ ID NO: 35), optionally with one or two mutations at any of positions 1 or 3-6 of SEQ ID NO: 35 (i.e. the mutations exclude Y2 numbered according to SEQ ID NO: 35); and
- a beta chain CDR3 comprising the sequence of ASSIWSIGGASSGNLS (SEQ ID NO: 41), optionally with one, two or three mutations at any of positions 1-3, 9, 10 or 13-16 of SEQ ID NO: 41 (i.e. the mutations exclude I4, W5, S6, I7, G8, S11 and S12 numbered according to SEQ ID NO: 41).

The binding molecule of the first aspect of the invention may comprise
- an alpha chain CDR3 comprising the sequence of VVGAPHHNDKII (SEQ ID NO: 30), optionally with one or two mutations at any of positions 1-4 or 8-12 of SEQ ID NO: 30 (i.e. the mutations exclude P5, H6 and H7 numbered according to SEQ ID NO: 30);
- a beta chain CDR1 comprising the sequence of SGDYS (SEQ ID NO: 32), optionally with one mutation at any of positions 1-3 or 5 of SEQ ID NO: 32 (i.e. the mutations exclude Y5 numbered according to SEQ ID NO: 32);
- a beta chain CDR2 comprising the sequence of YYNAEE (SEQ ID NO: 35), optionally with one mutation at any of positions 1 or 3-6 of SEQ ID NO: 35 (i.e. the mutations exclude Y2 numbered according to SEQ ID NO: 35); and
- a beta chain CDR3 comprising the sequence of ASSIWSIGGASSGNLS (SEQ ID NO: 41), optionally with one or two mutations at any of positions 1-3, 9, 10 or 13-16 of SEQ ID NO: 41 (i.e. the mutations exclude I4, W5, S6, I7, G8, S11 and S12 numbered according to SEQ ID NO: 41).

The binding molecule of the first aspect of the invention may comprise
an alpha chain CDR3 comprising the sequence of VVGAPHHNDKII (SEQ ID NO: 30), optionally with one mutation at any of positions 1~4 or 8-12 of SEQ ID NO: 30 (i.e. the mutations exclude P5, H6 and H7 numbered according to SEQ ID NO: 30);
a beta chain CDR1 comprising the sequence of SGDYS (SEQ ID NO: 32), optionally with one mutation at any of positions 1-3 or 5 of SEQ ID NO: 32 (i.e. the mutations exclude Y5 numbered according to SEQ ID NO: 32);
a beta chain CDR2 comprising the sequence of YYNAEE (SEQ ID NO: 35), optionally with one mutation at any of positions 1 or 3-6 of SEQ ID NO: 35 (i.e. the mutations exclude Y2 numbered according to SEQ ID NO: 35); and
a beta chain CDR3 comprising the sequence of ASSIWSIGGASSGNLS (SEQ ID NO: 41), optionally with one mutation at any of positions 1-3, 9, 10 or 13-16 of SEQ ID NO: 41 (i.e. the mutations exclude I4, W5, S6, I7, G8, S11 and S12 numbered according to SEQ ID NO: 41).

The binding molecule of the first aspect of the invention may comprise
an alpha chain CDR1 comprising the sequence SSYSPS (SEQ ID NO: 5), optionally with one, two or three mutations therein, and
an alpha chain CDR2 comprising the sequence YIGNVTLV (SEQ ID NO: 27), optionally with one, two, three or four mutations therein.

The binding molecule of the first aspect of the invention may comprise
an alpha chain CDR1 comprising the sequence SSYSPS (SEQ ID NO: 5), optionally with one or two mutations therein, and
an alpha chain CDR2 comprising the sequence YIGNVTLV (SEQ ID NO: 27), optionally with one or two mutations therein.

The binding molecule of the first aspect of the invention may comprise
an alpha chain CDR1 comprising the sequence SSYSPS (SEQ ID NO: 5), optionally with one mutation therein, and
an alpha chain CDR2 comprising the sequence YIGNVTLV (SEQ ID NO: 27), optionally with one mutation therein.

The binding molecule of the first aspect of the invention may comprise an alpha chain CDR1 comprising the sequence S/T-S/T-Y/W/F-S/T-P/G-S/T (SEQ ID NO: 129) and an alpha chain CDR2 comprising the sequence Y/W/F-T/I-S/G-A/N-A/D/V-T/S-L/I/V-V/I/L (SEQ ID NO: 131). The binding molecule of the first aspect of the invention may comprise an alpha chain CDR1 comprising the sequence S/T-S/T-Y/W/F-S/T-P-S/T (SEQ ID NO: 130) and an alpha chain CDR2 comprising the sequence Y/W/F-I-G-N-V-T/S-L/I/V-V/I/L (SEQ ID NO: 132).

In the sequences specified herein, "X" represents any amino acid. The forward slash ("/") represents "or", e.g., "S/T" indicates that the amino acid can be S (Ser) or T (Thr) at the specified position in the sequence.

In the binding molecule of the third aspect of the invention, the mutations in the alpha chain CDRs may be selected from T51I, S52G, A53N, A54V, A54D, S94G, N97H, R98H and D99N, numbered according to SEQ ID NO: 3. Thus, there may be any or all of these mutations, optionally in combination with other mutations. In particular, the binding molecule may comprise the following mutations in the alpha chain CDRs, numbered according to SEQ ID NO: 3:

(a) S94G, N97H and D99N;
(b) T51I, S52G, A53N, A54D, S94G, N97H and D99N;
(c) T51I, S52G, A53N, A54V, S94G, N97H and D99N; or
(d) T51I, S52G, A53N, A54V, S94G, N97H, R98H and D99N The T51I, S52G, A53N, A54V, S94G, N97H, R98H and D99N mutations listed in part (d) above are preferred.

In the binding molecule of the second aspect of the invention, the mutations in the alpha chain CDRs may be conservative, semi-conservative, tolerated or other phenotypically silent mutations, as described herein. The mutations may be selected from I51T, G52S, N53A, V54A, D54A, G94S, H97N, H98R and N99D, numbered according to SEQ ID NO: 29. Other suitable conservative, semi-conservative, tolerated or other phenotypically silent mutations will be apparent to those skilled in the art.

A mutated alpha chain variable domain may be paired with any beta chain variable domain defined herein.

There may be at least one mutation in the TCR beta chain variable region of the binding molecules of the invention. There may be one, two, three, four, five, six, seven, eight, nine, ten or more, mutations in the beta chain CDRs (i.e. in total across all three CDRs). For example, there may be seven mutations in the beta chain CDRs. There may be one mutation in the beta chain CDR1 and/or one mutation in the beta chain CDR2 and/or five mutations in the beta chain CDR3.

In the binding molecule of the third aspect of the invention, the mutation(s) in the beta chain CDRs may be selected from L30Y, G52A, V95I, S98I, A103S, E105N and F107S, numbered according to SEQ ID NO: 13. Thus, there may be any or all of these mutations, optionally in combination with other mutations. In particular, the binding molecule may comprise the following mutations in the beta chain CDRs, numbered according to SEQ ID NO: 13:

(a) L30Y, S98N A103S, E105N and F107S;
(b) L30Y, G52A, S98I, A103S, E105N and F107S; or
(c) L30Y, G52A, V95I, S98I, A103S, E105N and F107S.

The L30Y, G52A, V95I, S98I, A103S, E105N and F107S mutations listed in part (c) above are preferred.

In the binding molecule of the second aspect of the invention, the mutations in the beta chain CDRs may be conservative, semi-conservative, tolerated or other phenotypically silent mutations, as described herein. For example, the mutations may be selected from Y30L, A52G, I95V, I98S, S103A, N105E and S107F, numbered according to SEQ ID NO: 40. Other suitable conservative, semi-conservative, tolerated or other phenotypically silent mutations will be apparent to those skilled in the art.

A mutated beta chain variable domain may be paired with any alpha chain variable region defined herein.

Mutation(s) within the CDRs, relative to a native sequence, may improve the binding affinity or stability of the binding molecule of the invention but may additionally or alternatively confer other advantages such as improved specificity or improved potency when fused to an immune effector. Mutations may also reduce the risk of destabilising post-translational modifications, such as deamidation. Mutations at one or more positions may additionally or alternatively affect the interaction of an adjacent position with the cognate pMHC complex, for example by providing a more favourable angle for interaction. Mutations may include those that result in a reduction in non-specific binding, i.e. a reduction in binding to alternative antigens relative to the PYLGQMINL (SEQ ID NO: 1)-HLA-A24 complex. Mutations may include those that increase efficacy of folding and/or stability and/or manufacturability. Some mutations may contribute to each of these characteristics; others may contribute to affinity but not to specificity, for example, or to specificity but not to affinity, or to stability but not affinity etc.

At least 3, at least 5 or at least 10 CDR mutations, relative to a wild type sequence, in total may be needed to obtain binding molecules with pM affinity for target antigen. Binding molecules with pM affinity for their target antigen are especially suitable as soluble therapeutics. Binding molecules for use in adoptive therapy applications may have lower affinity for target antigen and thus fewer CDR mutations, for example, up to 1, up to 2, up to 5, or more CDR mutations in total. In some cases the native (also referred to as unmutated) binding molecule may have a sufficiently high affinity for target antigen without the need for mutation. The binding molecules of the present invention in their native form also have advantageously high affinity and specificity.

The binding molecules of the invention may comprise one of the following combinations of alpha chain CDRs and beta chain CDRs:
(a) alpha chain CDR1, CDR2 and CDR3 amino acid sequences of SSYSPS (SEQ ID NO: 5), YTSAATLV (SEQ ID NO: 6) and VVSAPNRDDKII (SEQ ID NO: 7), respectively, and beta chain CDR1, CDR2 and CDR3 amino acid sequences of SGDLS (SEQ ID NO: 15), YYNGEE (SEQ ID NO: 16) and ASSVWSSG-GASAGELF (SEQ ID NO: 17), respectively;
(b) alpha chain CDR1, CDR2 and CDR3 amino acid sequences of SSYSPS (SEQ ID NO: 5), YTSAATLV (SEQ ID NO: 6) and VVGAPHRNDKII (SEQ ID NO: 23), respectively, and beta chain CDR1, CDR2 and CDR3 amino acid sequences of SGDLS (SEQ ID NO: 15), YYNGEE (SEQ ID NO: 16) and ASSVWSSG-GASAGELF (SEQ ID NO: 17), respectively;
(c) alpha chain CDR1, CDR2 and CDR3 amino acid sequences of SSYSPS (SEQ ID NO: 5), YIGNDTLV (SEQ ID NO: 25) and VVGAPHRNDKII (SEQ ID NO: 23), respectively, and beta chain CDR1, CDR2 and CDR3 amino acid sequences of SGDYS (SEQ ID NO: 32), YYNGEE (SEQ ID NO: 16) and ASSVWSNG-GASSGNLS (SEQ ID NO: 33), respectively;
(d) alpha chain CDR1, CDR2 and CDR3 amino acid sequences of SSYSPS (SEQ ID NO: 5), YIGNVTLV (SEQ ID NO: 27) and VVGAPHRNDKII (SEQ ID NO: 23), respectively, and beta chain CDR1, CDR2 and CDR3 amino acid sequences of SGDYS (SEQ ID NO: 32), YYNAEE (SEQ ID NO: 35) and ASSVWSIG-GASSGNLS (SEQ ID NO: 36), respectively; or
(e) alpha chain CDR1, CDR2 and CDR3 amino acid sequences of SSYSPS (SEQ ID NO: 5), YIGNVTLV (SEQ ID NO: 27) and VVGAPHHNDKII (SEQ ID NO: 30), respectively, and beta chain CDR1, CDR2 and CDR3 amino acid sequences of SGDYS (SEQ ID NO: 32), YYNAEE (SEQ ID NO: 35) and ASSIWSIG-GASSGNLS (SEQ ID NO: 41), respectively.

Preferably, the binding molecule comprises alpha chain CDR1, CDR2 and CDR3 amino acid sequences of SSYSPS (SEQ ID NO: 5), YIGNVTLV (SEQ ID NO: 27) and VVGAPHHNDKII (SEQ ID NO: 30), respectively, and beta chain CDR1, CDR2 and CDR3 amino acid sequences of SGDYS (SEQ ID NO: 32), YYNAEE (SEQ ID NO: 35) and ASSIWSIGGASSGNLS (SEQ ID NO: 41), respectively. These are the CDR sequences of the TCR referred to as "a90b152" in the Examples.

Mutations may additionally, or alternatively, be made outside of the CDRs, within the framework regions; such mutations may result in improved therapeutic properties, such as improve affinity, and/or specificity, and/or stability, and/or the yield of a purified soluble form of the binding molecule. For example, the binding molecules of the invention may, additionally or alternatively, comprise one or more mutations at the N terminus of FR1, of one of both chains, relative to the canonical framework sequences for a given TRAV and TRBV chain. Such mutations may improve the efficiency of N-terminal methionine cleavage. The removal of an N-terminal initiation methionine is often crucial for the function and stability of proteins. Inefficient cleavage may be detrimental for a therapeutic, since it may result in a heterogeneous protein product, and or the presence of the initiation methionine may be immunogenic in humans. In some cases an initiation methionine may be present in the binding molecules of the invention.

The alpha chain variable domain framework regions of the binding molecule of the invention may comprise the following sequences:
FR1—AQSVTQLDSHVSVSEGTPVLLRCNYS (SEQ ID NO: 8), optionally with one, two or three mutations therein,
FR2—LFWYVQHPNKGLQLLLK (SEQ ID NO: 9), optionally with one, two or three mutations therein,
FR3—KGINGFEAEFKKSETSFHLTKPSAHMS-DAAEYFC (SEQ ID NO: 10), optionally with one, two or three mutations therein,
FR4—FGKGTRLHILP (SEQ ID NO: 11), optionally with one, two or three mutations therein,
and/or
the beta chain variable domain framework regions may comprise the following sequences:
FR1—DSGVTQTPKHLITATGQRVTLRCSPR (SEQ ID NO: 18), optionally with one, two or three mutations therein,
FR2—VYWYQQSLDQGLQFLIQ (SEQ ID NO: 19), optionally with one, two or three mutations therein,
FR3—RAKGNILERFSAQQFPDLHSELNLSSLELGD-SALYFC (SEQ ID NO: 20), optionally with one, two or three mutations therein,
FR4—FGEGSRLTVL (SEQ ID NO: 21), optionally with one, two or three mutations therein.

The alpha chain framework regions FR1, FR2, and FR3 may comprise amino acid sequences corresponding to a TRAV8-2*01 chain and/or the beta chain framework regions FR1, FR2 and FR3, may comprise amino acid sequences corresponding to those of a TRBV9*01 chain.

The FR4 region may comprise the joining region of the alpha and beta variable chains (TRAJ and TRBJ, respectively). The TRAJ region may comprise amino acid sequences corresponding to those of TRAJ30*01. The TRBJ region may comprise amino acid sequences corresponding to those of TRBJ2-2*01.

The alpha chain variable domain framework regions may have one, two, three, four, five or more mutations in total, relative to the above sequences. The alpha chain variable domain framework regions may have one mutation, relative to the above sequences. The alpha chain variable domain framework regions may comprise a N61Q mutation, numbered according to SEQ ID NO: 3. The alpha chain variable domain framework regions may comprise no other mutations (other than N61Q).

The beta chain variable domain framework regions may have one, two, three, four, five or more mutations in total, relative to the above sequences. The beta chain variable domain framework regions may have five mutations, relative to the above sequences. The beta chain variable domain framework regions comprise one or more or all of the following mutations T13K, L43P, I47F, L61P and F90I, numbered according to SEQ ID NO: 13. The beta chain variable domain framework regions may comprise the following mutations: T13K, L43P, I47F, L61P and F90I, numbered according to SEQ ID NO: 13. The beta chain variable domain framework regions may comprise no other mutations relative to the above sequences.

The alpha chain variable domain of the binding molecule of the invention may comprise respective framework amino acid sequences that have at least 90%, at least 91%, at least 92%, at least 93%, at least 94%, at least 95%, at least 96%, at least 97%, at least 98% or at least 99% identity to SEQ ID NOs: 8, 9, 10 and 11. The beta chain variable domain of the binding molecule of the invention may comprise respective framework amino acid sequences that have at least 90%, at least 91%, at least 92%, at least 93%, at least 94%, at least 95%, at least 96%, at least 97%, at least 98% or at least 99% identity to SEQ ID NOs: 18, 19, 20 and 21. Alternatively, the stated percentage identity may be over the framework sequences when considered as a whole.

The alpha chain variable domain may comprise any one of the amino acid sequences of SEQ ID NOs: 3, 22, 24, 26, 29, 109, 110, 111, 118 or 119, or an amino acid sequence having at least 80%, at least 90%, at least 95% or at least 98% identity to any one of SEQ ID NOs: 3, 22, 24, 26, 29, 109, 110, 111, 118 or 119. The beta chain variable domain may comprise any one of the amino acid sequences of SEQ ID NOs: 13, 31, 34, 40, 106 to 108, 112 to 117 or 120 to 124, or an amino acid sequence having at least 80%, at least 90%, at least 95% or at least 98% identity to any one of SEQ ID NOs: 13, 31, 34, 40, 106 to 108, 112 to 117 or 120 to 124. As all alpha chain variable domains and beta chain variable domains are derived from the same scaffold TCR sequences (i.e., SEQ ID NO: 3 and SEQ ID NO: 13 respectively) it is expected that all alpha chain variable domain sequences are compatible with all beta chain variable domain sequences. Thus, the alpha chain variable domain may comprise an amino acid sequence provided in any one of SEQ ID NOs: 3, 22, 24, 26, 29, 109, 110, 111, 118 or 119, or an amino acid sequence with at least 90% identity thereto, and the beta chain variable domain may comprise an amino acid sequence provided in any one of SEQ ID NOs: 13, 31, 34, 40, 106 to 108, 112 to 117 or 120 to 124, or an amino acid sequence with at least 90% identity thereto.

The alpha chain variable domain may comprise any one of the amino acid sequences of SEQ ID NOs: 3, 22, 24, 26, or 29, or an amino acid sequence having at least 80%, at least 90%, at least 95% or at least 98% identity to any one of SEQ ID NOs: 3, 22, 24, 26, or 29. The beta chain variable domain may comprise any one of the amino acid sequences of SEQ ID NOs: 13, 31, 34, or 40, or an amino acid sequence having at least 80%, at least 90%, at least 95% or at least 98% identity to any one of SEQ ID NOs: 13, 31, 34, or 40. As all alpha chain variable domains and beta chain variable domains are derived from the same scaffold TCR sequences (i.e., SEQ ID NO: 3 and SEQ ID NO: 13 respectively) it is expected that all alpha chain variable domain sequences are compatible with all beta chain variable domain sequences. Thus, the alpha chain variable domain may comprise an amino acid sequence provided in any one of SEQ ID NOs: 3, 22, 24, 26, or 29, or an amino acid sequence with at least 90% identity thereto, and the beta chain variable domain may comprise an amino acid sequence provided in any one of SEQ ID NOs: 13, 31, 34, or 40, or an amino acid sequence with at least 90% identity thereto.

The binding molecule may comprise one of the following combinations of alpha and beta chain variable domains:
(a) an alpha chain variable domain comprising the amino acid sequence provided in SEQ ID NO: 22 and a beta chain variable domain comprising the amino acid sequence provided in SEQ ID NO: 13;
(b) an alpha chain variable domain comprising the amino acid sequence provided in SEQ ID NO: 24 and a beta chain variable domain comprising the amino acid sequence provided in SEQ ID NO: 31;
(c) an alpha chain variable domain comprising the amino acid sequence provided in SEQ ID NO: 26 and a beta chain variable domain comprising the amino acid sequence provided in SEQ ID NO: 34; or
(d) an alpha chain variable domain comprising the amino acid sequence provided in SEQ ID NO: 29 and a beta chain variable domain comprising the amino acid sequence provided in SEQ ID NO: 40.

Preferably, the alpha chain variable domain comprises the amino acid sequence provided in SEQ ID NO: 29 and the beta chain variable domain comprises the amino acid sequence provided in SEQ ID NO: 40. In this regard, the invention provides a binding molecule having the property of binding to PYLGQMINL (SEQ ID NO: 1) in complex with HLA-A24, wherein the binding molecule comprises an alpha chain variable domain comprising the amino acid sequence provided in SEQ ID NO: 29, or an amino acid sequence having at least 80%, at least 90%, at least 95% or at least 98% identity to SEQ ID NO: 29, and a beta chain variable domain comprising the amino acid sequence provided in SEQ ID NO: 40, or an amino acid sequence having at least 80%, at least 90%, at least 95% or at least 98% identity to SEQ ID NO: 40.

In the binding molecules of the invention, the variable domains, and where present the constant domains and/or any other domains, may be organised in any suitable format/arrangement that allows antigen binding. As used herein, a "format" of an binding molecule specifies a defined spatial arrangement of domains, in particular variable and optionally constant domains. Characteristics of such protein formats are the number of polypeptide chains (single chain, double chain or multiple chains), the type and length of linkers connecting different domains, the number of antigen binding moieties (and thus the number of valences), the number of different antigen binding moieties (and thus the number of specificities for different antigens, e.g. bispecific, multispecific), and the order and orientation of variable domains (e.g. cross-over, parallel). For example, the variable domains may be arranged in monoclonal TCR format, in which the two chains are linked by a disulphide bond, either within the constant domains or variable domains, or in which the variable domains are fused to one or more dimerization domains. Alternatively the variable domains may be arranged in single chain format in the present or absence of one or more constant domains, or the variable domains may be arranged in diabody format. Other suitable formats are described herein.

Binding molecules of the invention may comprise at least one TCR constant domain or fragment thereof, for example an alpha chain TRAC constant domain and/or a beta chain TRBC1 or TRBC2 constant domain. As will be appreciated by those skilled in the art the term TRAC and TRBC1/2 also encompasses natural polymorphic variants, for example N to K at position 4 of TRAC (Bragado et al International immunology. 1994 February; 6(2):223-30).

Where present, one or both of the constant domains may contain mutations, substitutions or deletions relative to native constant domain sequences. The constant domains may be truncated, i.e. having no transmembrane or cytoplasmic domains. Thus, the binding molecule of the invention may comprise the extracellular region of a TCR alpha chain constant domain and/or the extracellular region of a TCR beta chain constant domain. Alternatively, the constant domains may be full-length by which it is meant that extracellular, transmembrane and cytoplasmic domains are all present. The TRAC and TRBC domain sequences may be modified by truncation or substitution to delete the native disulphide bond between Cys4 of exon 2 of TRAC and Cys2 of exon 2 of TRBC1 or TRBC2. The alpha and/or beta chain constant domain sequence(s) may have an introduced disulphide bond between residues of the respective constant domains, as described, for example, in WO 03/020763. Thus, the binding molecule may comprise a non-native covalent disulphide bond that links a residue of the TCR alpha chain constant domain to a residue of the TCR beta chain constant domain. Preferably the alpha and beta constant domains may be modified by substitution of cysteine residues at position Thr 48 of TRAC and position Ser 57 of TRBC1 or TRBC2, the said cysteines forming a non-natural disulphide bond between the alpha and beta constant domains of the TCR. TRBC1 or TRBC2 may additionally include a cysteine to alanine mutation at position 75 of the constant domain and an asparagine to aspartic acid mutation at position 89 of the constant domain. One or both of the extracellular constant domains, e.g., present in an αβ heterodimer, may be further truncated at the C terminus or C termini, for example by up to 15, or up to 10, or up to 8 or fewer amino acids. One or both of the extracellular constant domains, e.g., present in an αβ heterodimer, may be truncated at the C terminus or C termini by, for example, up to 15, or up to 10 or up to 8 amino acids. The C terminus of the alpha chain extracellular constant domain may be truncated by 8 amino acids.

A binding molecule of the invention may comprise the extracellular region of a TCR alpha chain constant domain, optionally truncated at the C terminus by up to 15 amino acids, and/or the extracellular region of a TCR beta chain constant domain, optionally truncated at the C terminus by up to 15 amino acids. The binding molecule of the invention may comprise the extracellular region of a TCR beta chain constant domain comprising a L3M mutation, numbered according to SEQ ID NO: 14. Such a mutation has been identified by the inventors to provide enhanced stability of the TCRs referred to herein as a77150 and a90b152, relative to the native TCR sequence.

The extracellular region of the TCR alpha chain constant domain may comprise the amino acid sequence provided in SEQ ID NO: 4, or an amino acid sequence that has at least 90% identity to the sequence provided in SEQ ID NO: 4, and/or the extracellular region of the TCR beta chain constant domain may comprise the amino acid sequence provided in SEQ ID NO: 48, or an amino acid sequence that has at least 90% identity to the sequence provided in SEQ ID NO: 48.

The binding molecule may comprise the extracellular region of a TCR alpha chain constant domain comprising the amino acid sequence provided in SEQ ID NO: 4 and the extracellular region of a TCR beta chain constant domain comprising the amino acid sequence provided in SEQ ID NO: 48. The binding molecule may not comprise a transmembrane or cytoplasmic domain of a TCR.

Alternatively, rather than full-length or truncated constant domains there may be no TCR constant domains. Accordingly, the binding molecule of the invention may consist of the variable domains of the TCR alpha and beta chains, optionally with additional domains as described herein. Additional domains include but are not limited to immune effector domains (such as antibody domains), Fc domains or albumin binding domains, therapeutic agents or detectable labels.

The binding molecule may comprise the TCR alpha and beta chain variable domains in a single chain format. Single chain formats include, but are not limited to, αβ TCR polypeptides of the Vα-L-Vβ, Vβ-L-Vα, Vα-Cα-L-Vβ, Vα-L-Vβ-Cβ, or Vα-Cα-L-Vβ-Cβ types, wherein Vα and Vβ are TCR α and β variable regions respectively, Cα and Cβ are TCR α and β constant regions respectively, and L is a linker sequence (Weidanz et al., (1998) J Immunol Methods. December 1; 221(1-2):59-76; Epel et al., (2002), Cancer Immunol Immunother. November; 51(10):565-73; WO 2004/033685; WO9918129).

The term "linker" as used herein refers to one or more amino acid residues inserted between domains, or a domain and an agent, to provide sufficient mobility for the domains or elements, for example the domains of the binding molecules of the invention to fold correctly to form the antigen binding sites. A linker may be inserted at the transition between variable domains or between variable domains and constant domains (or other domains), respectively, at the amino acid sequence level. The transition between domains can be identified because the approximate size of antibody domains as well as TCR domains is well understood by those skilled in the art. The precise location of a domain transition can be determined by locating peptide stretches that do not form secondary structural elements such as beta-sheets or alpha-helices as demonstrated by experimental data or as can be assumed by techniques of modelling or secondary structure prediction.

Linker sequences are usually flexible, in that they are made up primarily of amino acids such as glycine, alanine and serine, which do not have bulky side chains likely to restrict flexibility. Alternatively, linkers with greater rigidity may be desirable. Usable or optimum lengths of linker sequences may be easily determined. Often the linker sequence will be less than about 12, such as less than 10, or from 2-10 amino acids in length. The linker may be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acids in length. Examples of suitable linkers that may be used in binding molecules of the invention include, but are not limited to: GGGGS (SEQ ID NO: 64), GGGSG (SEQ ID NO: 70), GGSGG (SEQ ID NO: 71), GSGGG (SEQ ID NO: 72), GSGGGP (SEQ ID NO: 73), GGEPS (SEQ ID NO: 74), GGEGGGP (SEQ ID NO: 75), GGEGGGSEGGGS (SEQ ID NO: 76), GGGSGGGG (SEQ ID NO: 77), GGGGSGGGGSGGGGSGGGGSGGGS (SEQ ID NO: 59), GGGGSGGGGSGGGGSGGGGS (SEQ ID NO: 78), EAAAK (SEQ ID NO: 79) and EAAAKEAAAKEAAAK (SEQ ID NO: 80). Where present, one or both of the constant domains may be full length, or they may be truncated and/or contain mutations as described above. Single chain TCRs may be soluble, i.e., they do not comprise a transmembrane domain. In certain embodiments single chain TCRs of the invention may have an introduced disulphide bond between residues of the respective constant domains, as described in WO 2004/033685. Single chain TCRs are further described in WO2004/033685; WO98/39482; WO01/62908; Weidanz et al. (1998) J Immunol Methods 221(1-2): 59-76; Hoo et al. (1992) Proc Natl Acad Sci USA 89(10): 4759-4763; Schodin (1996) Mol Immunol 33(9): 819-829).

Alternatively the binding molecule may comprise two or more polypeptide chains, wherein the TCR alpha chain variable domain and the TCR beta chain variable domain are comprised in separate polypeptide chains.

The TCR variable domains may be arranged in diabody format. In the diabody format two single chain fragments dimerize in a head-to-tail orientation resulting in a compact molecule with a molecular mass similar to tandem scFv (~50 kDa).

Particularly suitable TCR alpha chain sequences include, but are not limited to, any one of SEQ ID NOs: 2, 42, 44, 46 or 49. Particularly suitable TCR beta chain sequences include, but are not limited to, any one of SEQ ID NOs: 12, 45, 47 or 50. Such sequences do not comprise transmembrane or cytoplasmic domains. It is expected that every alpha chain sequence (i.e., SEQ ID NOs: 2, 42, 44, 46 or 49) is compatible with every beta chain sequence (i.e., SEQ ID NOs: 12, 45, 47 or 50), as they are all derived from the same native (scaffold) TCR sequences (SEQ ID NOs: 2 and 12 respectively).

Thus, the binding molecule of the invention may comprise a TCR alpha chain comprising an amino acid sequence as set forth in any one of SEQ ID NOs: 2, 42, 44, 46 or 49, or an amino acid sequence that has at least 90% identity, such as at least 90%, at least 91%, at least 92%, at least 93%, at least 94%, at least 95%, at least 96%, at least 97%, at least 98%, or at least 99%, to the amino acid sequence as set forth in any one of SEQ ID NOs: 2, 42, 44, 46, or 49, and a TCR beta chain comprising an amino acid sequence as set forth in any one of SEQ ID NOS: 12, 45, 47 or 50, or an amino acid sequence that has at least 90% identity, such as at least 90%, at least 91%, at least 92%, at least 93%, at least 94%, at least 95%, at least 96%, at least 97%, at least 98%, or at least 99%, to the amino acid sequence as set forth in any one of SEQ ID NOs: 12, 45, 47 or 50.

More specifically, the binding molecule may comprise
(a) a TCR alpha chain comprising the amino acid sequence of SEQ ID NO: 42 and a TCR beta chain comprising the amino acid sequence of SEQ ID NO: 12;
(b) a TCR alpha chain comprising the amino acid sequence of SEQ ID NO: 44 and a TCR beta chain comprising the amino acid sequence of SEQ ID NO: 45;
(c) a TCR alpha chain comprising the amino acid sequence of SEQ ID NO: 46 and a TCR beta chain comprising the amino acid sequence of SEQ ID NO: 47; or
(d) a TCR alpha chain comprising the amino acid sequence of SEQ ID NO: 49 and a TCR beta chain comprising the amino acid sequence of SEQ ID NO: 50.

Preferably, the binding molecule comprises a TCR alpha chain comprising the amino acid sequence of SEQ ID NO: 49 and a TCR beta chain comprising the amino acid sequence of SEQ ID NO: 50. In this regard, the invention provides a binding molecule having the property of binding to PYLGQMINL (SEQ ID NO: 1) in complex with HLA-A24, wherein the binding molecule comprises a TCR alpha chain comprising the amino acid sequence of SEQ ID NO: 49, or an amino acid sequence that has at least 90% identity, such as at least 90%, at least 91%, at least 92%, at least 93%, at least 94%, at least 95%, at least 96%, at least 97%, at least 98%, or at least 99%, to the amino acid sequence of SEQ ID NO: 49, and a TCR beta chain comprising the amino acid sequence of SEQ ID NO: 50, or an amino acid sequence that has at least 90% identity, such as at least 90%, at least 91%, at least 92%, at least 93%, at least 94%, at least 95%, at least 96%, at least 97%, at least 98%, or at least 99%, to the amino acid sequence of SEQ ID NO: 50.

Binding molecules of the invention are useful for delivering detectable labels or therapeutic agents to antigen presenting cells and tissues containing antigen presenting cells. They may therefore comprise or be associated (covalently or otherwise) with a detectable label (for diagnostic purposes wherein the binding molecule is used to detect the presence of cells presenting the cognate antigen); and or a therapeutic agent, including immune effectors; and or a pharmacokinetics (PK) modifying moiety.

Examples of PK modifying moieties include, but are not limited to, PEG (Dozier et al., (2015) Int J Mol Sci. October 28; 16(10):25831-64 and Jevsevar et al., (2010) Biotechnol J. January; 5(1):113-28), PASylation (Schlapschy et al., (2013) Protein Eng Des Sel. August; 26(8):489-501), albumin, and albumin binding domains, (Dennis et al., (2002) J Biol Chem. September 20; 277(38):35035-43), and/or unstructured polypeptides (Schellenberger et al., (2009) Nat Biotechnol. December; 27(12):1186-90). Further PK modifying moieties include immunoglobulin Fc domains. PK modifying moieties may serve to extend the in vivo half-life of binding molecules of the invention.

Where an immunoglobulin Fc domain is used, it may be any antibody Fc region. The Fc region is the tail region of an antibody that interacts with cell surface Fc receptors and some proteins of the complement system. The Fc region typically comprises two polypeptide chains both having two or three heavy chain constant domains (termed CH2, CH3 and CH4), and a hinge region. The two chains being linked by disulphide bonds within the hinge region. Fc domains from immunoglobulin subclasses IgG1, IgG2 and IgG4 bind to and undergo FcRn mediated recycling, affording a long circulatory half-life (3-4 weeks). The interaction of IgG with FcRn has been localized in the Fc region covering parts of the CH2 and CH3 domain. Particularly suitable immunoglobulin Fc for use in the present invention include but are not limited to Fc domains from IgG1 or IgG4. The Fc domain may be derived from human sequences. The Fc region may also preferably include KiH mutations which facilitate dimerization, as well as mutations to prevent interaction with activating receptors i.e. functionally silent molecules. The immunoglobulin Fc domain may be fused to the C or N terminus of the other domains (i.e., the TCR variable domains and/or TCR constant domains and/or immune effector domains), in any suitable order or configuration. The immunoglobulin Fc may be fused to one or more of the other domains (i.e., the TCR variable domains and/or TCR constant domains and/or an immune effector domains) via a linker. Suitable linker sequences are known in the art and include those described herein. Where the immunoglobulin Fc is fused to the TCR, it may be fused to either the alpha or beta chains, with or without a linker. Furthermore, individual chains of the Fc may be fused to individual chains of the TCR.

The Fc region, if present, may comprise mutations relative to a WT sequence. Mutations include substitutions, insertions and deletions. Such mutations may be made for the purpose of introducing desirable therapeutic properties. For example, to facilitate heterodimerisation, knobs into holes (KiH) mutations may be engineered into the CH3 domain. In this case, one chain is engineered to contain a bulky protruding residue (i.e. the knob), such as Y, and the other is chain engineered to contain a complementary pocket (i.e. the hole). Suitable positions for KiH mutations are known in the art. Additionally or alternatively mutations may be introduced that abrogate or reduce binding to Fcγ receptors and or increase binding to FcRn, and/or prevent Fab arm exchange, or remove protease sites. Additionally, or alternatively, mutations improve manufacturability for example to remove or alter glycosylation sites.

The PK modifying moiety may also be albumin or an albumin-binding domain, which may also act to extend half-life. As is known in the art, albumin has a long circulatory half-life of 19 days, due in part to its size, being above the renal threshold, and by its specific interaction and recycling via FcRn. Attachment to albumin is a well-known strategy to improve the circulatory half-life of a therapeutic molecule in vivo. Albumin may be attached non-covalently, through the use of a specific albumin binding domain, or covalently, by conjugation or direct genetic fusion. Examples of therapeutic molecules that have exploited attachment to albumin for improved half-life are given in Sleep et al., Biochim Biophys Acta. 2013 December; 1830 (12):5526-34.

The albumin-binding domain may be any moiety capable of binding to albumin, including any known albumin-binding moiety. Albumin binding domains may be selected from endogenous or exogenous ligands, small organic molecules, fatty acids, peptides and proteins that specifically bind albumin. Examples of preferred albumin binding domains include short peptides, such as described in Dennis et al., J Biol Chem. 2002 Sep. 20; 277(38):35035-43 (for example the peptide QRLMEDICLPRWGCLWEDDF); proteins engineered to bind albumin such as antibodies, antibody fragments and antibody like scaffolds, for example Albudab® (O'Connor-Semmes et al., Clin Pharmacol Ther. 2014 December; 96(6):704-12), commercially provided by GSK and Nanobody® (Van Roy et al., Arthritis Res Ther. 2015 May 20; 17:135), commercially provided by Ablynx; and proteins based on albumin binding domains found in nature such as Streptococcal protein G Protein (Stork et al., Eng Des Sel. 2007 November; 20(11):569-76), for example Albumod® commercially provided by Affibody. Preferably, albumin is human serum albumin (HSA). The affinity of the albumin binding domain for human albumin may be in the range of picomolar to micromolar. Given the extremely high concentration of albumin in human serum (35-50 mg/ml, approximately 0.6 mM), it is calculated that substantially all of the albumin binding domains will be bound to albumin in vivo.

The albumin-binding moiety may be fused to the C or N terminus of the other domains (i.e., the TCR variable domains and/or TCR constant domains and/or an immune effector domain), in any suitable order or configuration. The albumin-binding moiety may be fused to one or more of the other domains (i.e., the TCR variable domains and/or TCR constant domains and/or an immune effector domain) via a linker. Suitable linkers are known in the art and include those described herein. Where the albumin-binding moiety is linked to the TCR, it may be linked to either the alpha or beta chains, with or without a linker.

Detectable labels for diagnostic purposes include for instance, fluorescent labels, radiolabels, enzymes, nucleic acid probes and contrast reagents.

For some purposes, the binding molecules of the invention may be aggregated into a complex comprising several binding molecules to form a multivalent binding molecule complex. There are a number of human proteins that contain a multimerisation domain that may be used in the production of multivalent binding molecule complexes. For example the tetramerisation domain of p53 which has been utilised to produce tetramers of scFv antibody fragments which exhibited increased serum persistence and significantly reduced off-rate compared to the monomeric scFv fragment (Willuda et al. (2001) J. Biol. Chem. 276 (17) 14385-14392). Haemoglobin also has a tetramerisation domain that could be used for this kind of application. A multivalent binding molecule complex of the invention may have enhanced binding capability for the complex compared to a non-multimeric native (also referred to as parental, natural, unmutated wild type, or scaffold) T cell receptor heterodimer of the invention. Thus, multivalent complexes of binding molecules of the invention are also included within the invention. Such multivalent binding molecule complexes according to the invention are particularly useful for tracking or targeting cells presenting particular antigens in vitro or in vivo, and are also useful as intermediates for the production of further multivalent binding molecule complexes having such uses.

Therapeutic agents which may be associated with or comprised in the binding molecules of the invention include immune-modulators and effectors, radioactive compounds, enzymes (perforin for example) or chemotherapeutic agents (cis-platin for example). To ensure that the therapeutic effects are exercised in the desired location the agent could be inside a liposome or other nanoparticle structure linked to the binding molecule so that the compound is released slowly. This will prevent damaging effects during the transport in the body and ensure that the agent has maximum effect after binding of the binding molecule to the relevant antigen presenting cells.

Examples of suitable therapeutic agents include, but are not limited to:
  antibodies, or fragments thereof, including anti-T cell or NK cell determinant antibodies (e.g. anti-CD3, anti-CD28 or anti-CD16)
  alternative protein scaffolds with antibody-like binding characteristics (e.g. DARPins)
  immuno-stimulants, i.e. immune effector molecules which stimulate immune response. For example, cytokines such as IL-2 and IFN-γ,
  chemokines such as IL-8, platelet factor 4, melanoma growth stimulatory protein, etc.
  activators of the complement pathway or Fc receptors
  checkpoint inhibitors, such as those that target PD1 or PD-L1
  small molecule cytotoxic agents, i.e. compounds with the ability to kill mammalian cells having a molecular weight of less than 700 Daltons. Such compounds could also contain toxic metals capable of having a cytotoxic effect. Furthermore, it is to be understood that these small molecule cytotoxic agents also include pro-drugs, i.e. compounds that decay or are converted under physiological conditions to release cytotoxic agents. Examples of such agents include cis-platin, maytansine derivatives, rachelmycin, calicheamicin, docetaxel, etoposide, gemcitabine, ifosfamide, irinotecan, melphalan, mitoxantrone, sorfimer sodiumphotofrin II, temozolomide, topotecan, trimetreate arbourate, auristatin E vincristine and doxorubicin
  peptide cytotoxins, i.e. proteins or fragments thereof with the ability to kill mammalian cells. For example, ricin, diphtheria toxin, *pseudomonas* bacterial exotoxin A, Dnase and Rnase;

radio-nuclides, i.e. unstable isotopes of elements which decay with the concurrent emission of one or more of ax or B particles, or γ rays. For example, iodine 131, rhenium 186, indium 111, yttrium 90, bismuth 210 and 213, actinium 225 and astatine 213; chelating agents may be used to facilitate the association of these radio-nuclides to TCRs, or multimers thereof;

superantigens and mutants thereof xenogeneic protein domains, allogeneic protein domains, viral/bacterial protein domains, viral/bacterial peptides Binding molecules of the invention may be multispecific. As used herein, the term "multispecific" refers to a binding molecule comprising two or more antigen binding moieties, including the TCR antigen binding moiety formed by the TCR alpha and beta chain variable domains. Such binding molecules are able to bind to the PYLGQMINL (SEQ ID NO: 1)-HLA-A24 complex and a further one or more different antigens. For example, the binding molecule may be bispecific. Such binding molecules comprise a TCR antigen binding moiety (formed by the alpha and beta chain variable domains) that binds to the PYLGQMINL (SEQ ID NO: 1)-HLA-A24 complex and one other antigen binding moiety (e.g., an antibody antigen binding moiety) that binds to a different antigen. This other antigen binding moiety may be referred to herein as the "second antigen binding moiety" and the antigen bound by the second antigen binding moiety may be referred to herein as the "second antigen". The term "antigen binding moiety" refers to a protein or region thereof that is capable of binding to an antigen. For example, this term encompasses antigen binding sites of antibodies, including antigen binding sites from conventional and engineered antibodies.

A multispecific binding molecule may comprise an antigen-binding moiety of an antibody that is capable of binding to an antigen (i.e., the second antigen). In this regard, the binding molecule may comprise an antibody or a functional fragment or variant thereof. The term "antibody" as used herein is meant to include conventional/native antibodies and engineered antibodies, in particular functional antibody fragments, single chain antibodies, single domain antibodies, bispecific or multispecific antibodies. "Native" or "conventional" refers to an antibody that has the same type of domains and domain arrangements as an antibody found in nature and comprises antibody-derived CDR and FR sequences. In a native/conventional antibody, two heavy chains are linked to each other by disulfide bonds and each heavy chain is linked to a light chain by a disulfide bond. The variable domains of both light (VL) and heavy (VH) chains determine binding recognition and specificity to the antigen. Conventional antibody binding sites are made up of residues that are primarily from the "antibody complementarity determining regions" (CDRs) or hypervariable regions. Occasionally, residues from non-hypervariable or framework regions (FR) influence the overall domain structure and hence the binding site. CDRs refer to amino acid sequences that together define the binding affinity and specificity of the natural Fv region of a native antibody binding site. The light and heavy chains of a conventional antibody each have three CDRs, designated CDR1-L, CDR2-L, CDR3-L and CDR1-H, CDR2-H, CDR3-H, respectively. A conventional antibody antigen-binding site, therefore, includes six CDRs, comprising the CDR set from each of a VH and VL.

"Engineered" antibody formats include functional antibody fragments, single chain antibodies, single domain antibodies, and chimeric, humanized, bispecific or multispecific antibodies. Engineered antibody formats further include constructs in which TCR-derived CDRs, possibly including additional 3, 2 or 1 N and/or C terminal framework residues, or entire TCR-derived variable domains are grafted onto antibody heavy or light chains. A "functional antibody fragment" refers to a portion of a full-length antibody, or a protein that resembles a portion of a full-length antibody, that retains the ability to bind to its target antigen, in particular the antigen binding region or variable region of the full-length antibody. Examples of functional antibody "fragments" include Fv, Fab, F(ab')2, Fab', dsFv, (dsFv)2, scFv, sc(Fv)2 and diabodies. For example, a binding molecule of the invention may comprise a scFv. A functional antibody fragment may also be a single domain antibody, such as a heavy chain antibody. Thus, the binding molecule may comprise a VHH, for example. As is known in the art, the antigen binding site of a single domain antibody, such as a VHH, may comprise three CDRs (as opposed to six in a conventional antibody). The term "antigen binding moiety of an antibody", as used herein, encompasses such binding sites. Alternatively, or additionally, the binding molecule may comprise a Fab or Fv fragment. The term "Fab" denotes an antibody fragment having a molecular weight of about 50,000 Dalton and antigen binding activity, in which about a half of the N-terminal side of H chain and the entire L chain, among fragments obtained by treating IgG with a protease, e.g. papain, are bound together through a disulfide bond. The Fv fragment is the N-terminal part of the Fab fragment of an antibody and consists of the variable portions of one light chain and one heavy chain.

Binding molecules comprising an antibody antigen-binding moiety, as described above, may be referred to as bispecific TCR-antibody molecules, i.e. binding molecules which comprise at least two antigen binding moieties, wherein one is derived from an antibody and the other is derived from a TCR. Such binding molecules may comprise an antibody heavy chain variable region (VH) and an antibody light chain variable region (VL), which associate to form the antibody antigen-binding moiety that is capable of binding to an antigen. Thus, the antigen binding moiety may comprise the VH and the VL. For example, the binding molecule may comprise a scFv comprising the VH and VL. Alternatively, the antigen binding moiety of the antibody may comprise a single variable domain (e.g., a VHH).

In such bispecific TCR-antibody molecules, the variable domains may be arranged e.g. as described for the different bispecific antibody formats discussed above. Techniques to produce such bispecific molecules are also disclosed in the above cited prior art and those skilled in the art can thus easily use the CDRs or the variable domains as herein defined to generate and produce the antigen binding proteins of the invention in the herein disclosed formats. In addition, further formats are possible, e.g. formats in which on each chain, the variable domains are separated by a constant domain that mediates dimerization, such that in the final molecule the two antigen binding sites are located on two sides of the dimerized constant domains. The skilled person is entirely capable of selecting suitable linkers to ensure folding in the desired conformation.

The second antigen binding moiety (e.g., an antibody antigen binding moiety comprising a VH and VL) may bind to an antigen of an effector cell. Such a binding molecule may be referred to as a "recruiter", as it recruits an effector cell to a tumour. In the context of the present invention, "effector cell" refers to a T cell or natural killer cell (NK cell). In particular, the antigen (i.e., the second antigen) may be a T cell surface antigen.

The antigen may be selected from the group consisting of CD2, CD3 (such as the CD3γ, CD3δ and CD3ε chains), CD4, CD5, CD7, CD8, CD10, CD11b, CD11c, CD14, CD16, CD18, CD22, CD25, CD28, CD32a, CD32b, CD33, CD41, CD41b, CD42a, CD42b, CD44, CD45RA, CD49, CD55, CD56, CD61, CD64, CD68, CD90, CD94, CD95, CD117, CD123, CD125, CD134, CD137, CD152, CD163, CD193, CD203c, CD235a, CD278, CD279, CD287, Nkp46, NKG2D, GITR, FcεRI, TCRα/β, TCRγ/δ, HLA-DR and 4-1 BB, or combinations thereof. "Combinations thereof" refers to complexes of two or more of said antigens, e.g. a TCRα/β CD3 complex. Preferably, the antigen is CD3.

Suitable antigen binding moieties for binding to CD3 include binding domains derived from the CD3-specific, humanized antibody hUCHT1 (Zhu et al., Identification of heavy chain residues in a humanized anti-CD3 antibody important for efficient antigen binding and T cell activation. J Immunol, 1995, 155, 1903-1910). In particular VH and VL domains derived from the UCHT1 variants UCHT1-V17, UCHT1-V17opt, UCHT1-V21 or UCHT1-V23 may be used. Alternatively, VH and VL domains derived from the antibody BMA031, which targets the TCRα/β CD3 complex, and humanized versions thereof (Shearman et al., Construction, expression and characterization of humanized antibodies directed against the human alpha/beta T cell receptor, J Immunol, 1991, 147, 4366-73) may be used, in particular VH and VL domains derived from BMA031 variants BMA031 (V36) or BMA031(V10). Suitable BMA031 antibody variant sequences are described in WO 2022/233957. As another alternative, VH and VL domains derived from the CD3-specific antibody H2C (described in EP 2155783) may be used.

Other suitable CD3-binding moieties may be derived from the anti-CD3 scFv referred to herein as "U0" (SEQ ID NO: 51) or "U28" (SEQ ID NO: 60). For example, the binding molecule may comprise an antibody antigen-binding moiety comprising a VH and a VL and which is capable of binding to CD3, wherein
(a) the VH comprises CDRs having the following sequences:

```
CDR1-
                              (SEQ ID NO: 56)
GYSFTGYT
or
                              (SEQ ID NO: 62)
GYSFTGYA;

CDR2-
                              (SEQ ID NO: 57)
INPYKGVS;
and

CDR3-
                              (SEQ ID NO: 58)
ARSGYYGDSDWYFDV,
``` and
(b) the VL comprises CDRs having the following sequences:

```
CDR1-
                              (SEQ ID NO: 52)
QDIRNY;

CDR2-
YTS;
and
```

```
CDR3-
                              (SEQ ID NO: 54)
QQGNTLPWT.
```

The binding molecule may comprise an antibody antigen-binding moiety comprising a VH and a VL and which is capable of binding to CD3, wherein
the VH comprises an amino acid sequence as set forth in SEQ ID NO: 55 or 61, or an amino acid sequence that has at least 90% identity, such as at least 90%, at least 91%, at least 92%, at least 93%, at least 94%, at least 95%, at least 96%, at least 97%, at least 98%, or at least 99%, to the amino acid sequence as set forth in SEQ ID NO: 55 or 61; and
the VL comprises an amino acid sequence as set forth in SEQ ID NO: 85, or an amino acid sequence that has at least 90% identity, such as at least 90%, at least 91%, at least 92%, at least 93%, at least 94%, at least 95%, at least 96%, at least 97%, at least 98%, or at least 99%, to the amino acid sequence as set forth in SEQ ID NO: 85.

The binding molecule may comprise a scFv that is capable of binding to CD3. The scFv may comprise a VH comprising the amino acid sequence as set forth in SEQ ID NO: 55, and a VL comprising the amino acid sequence as set forth in SEQ ID NO: 85. Such an scFv may comprise the amino acid sequence provided in SEQ ID NO: 51.

Alternatively, the scFv may comprise a VH comprising the amino acid sequence as set forth in SEQ ID NO: 61, and a VL comprising the amino acid sequence as set forth in SEQ ID NO: 85. Such an scFv may comprise the amino acid sequence provided in SEQ ID NO: 60.

For binding molecules comprising an antibody antigen-binding moiety, the VH or VL may be covalently linked to the C- or N-terminus of the TCR alpha chain or TCR beta chain, optionally via a linker sequence. Suitable linker sequences are known in the art. Linker sequences are usually flexible, in that they are made up primarily of amino acids such as glycine, alanine and serine, which do not have bulky side chains likely to restrict flexibility. Alternatively, linkers with greater rigidity may be desirable. Usable or optimum lengths of linker sequences may be easily determined. Often the linker sequence will be less than about 12, such as less than 10, or from 2-10 amino acids in length. For example, the VH or VL may be covalently linked to the C- or N-terminus of the TCR alpha chain or TCR beta chain via a linker sequence selected from GGGGS (SEQ ID NO: 64), GGGSG (SEQ ID NO: 70), GGSGG (SEQ ID NO: 71), GSGGG (SEQ ID NO: 72), GSGGGP (SEQ ID NO: 73), GGEPS (SEQ ID NO: 74), GGEGGGP (SEQ ID NO: 75), GGEGGGSEGGGS (SEQ ID NO: 76), GGGSGGGG (SEQ ID NO: 77), GGGGSGGGGSGGGGSGGGGSGGGS (SEQ ID NO: 59), GGGGSGGGGSGGGGSGGGGS (SEQ ID NO: 78), EAAAK (SEQ ID NO: 79) and EAAAKEAAAKEAAAK (SEQ ID NO: 80).

For binding molecules comprising an antigen binding moiety of an antibody, preferably the C-terminus of the VH is covalently linked to the N-terminus of the TCR beta chain, optionally via a linker comprising the amino acid sequence provided in SEQ ID NO: 64. Preferably, such a binding molecule comprises a first polypeptide chain and a second polypeptide chain, wherein:
the first polypeptide chain comprises a TCR alpha chain (the alpha chain itself comprising a variable domain and the extracellular region of a constant domain), and the second polypeptide chain (also referred to herein as a "beta chain-anti-CD3" chain) comprises a TCR beta chain (the beta chain itself comprising a variable domain and the extracellular region of a constant domain) and an scFv comprising a VH and a VL, wherein the C-terminus of the VH is covalently linked to the N-terminus of the TCR beta chain, optionally via a linker comprising the amino acid sequence provided in SEQ ID NO: 64.

Binding molecules in the format described above include ImmTAC® molecules. Examples of such molecules include tebentafusp, which is sold under the brand name KIMMTRAK® as well as the binding molecules described in WO2010133828, WO2019012138 and WO2019012141, for example. Exemplary binding molecules of the invention in this format include a9bwt-U0 (consisting of SEQ ID NOs: 42 and 63), a18b49-U0 (consisting of SEQ ID NOs: 44 and 65), a77b150-U0 (consisting of SEQ ID NOs: 46 and 66), a77b150-U28 (consisting of SEQ ID NOs: 46 and 67), a90b152-U0 (consisting of SEQ ID NOs: 49 and 68) and a90b152-U28 (consisting of SEQ ID NOs: 49 and 69).

A binding molecule in the format described above may comprise an alpha chain amino acid sequence as set forth in any one of SEQ ID NOs: 42, 44, 46 or 49, or an alpha chain amino acid sequence that has at least 90% identity, such as at least 90%, at least 91%, at least 92%, at least 93%, at least 94%, at least 95%, at least 96%, at least 97%, at least 98%, at least 99% or 100% identity, to the amino acid sequences as set forth in any one of SEQ ID NOs: 42, 44, 46 or 49, and
a beta chain-anti-CD3 amino acid sequence as set forth in any one of SEQ ID NOs: 63, 65, 66, 67, 68 or 69, or a beta chain amino acid sequence that has at least 90% identity, such as at least 90%, at least 91%, at least 92%, at least 93%, at least 94%, at least 95%, at least 96%, at least 97%, at least 98%, at least 99% or 100% identity, to the amino acid sequences as set forth in any one of SEQ ID NOs: 63, 65, 66, 67, 68 or 69.

More particularly, a binding molecule in the format described above may comprise
(a) an alpha chain amino acid sequence as set forth in SEQ ID NO: 42 and a beta chain-anti-CD3 amino acid sequence as set forth in SEQ ID NO: 63;
(b) an alpha chain amino acid sequence as set forth in SEQ ID NO: 44 and a beta chain-anti-CD3 amino acid sequence as set forth in SEQ ID NO: 65;
(c) an alpha chain amino acid sequence as set forth in SEQ ID NO: 46 and a beta chain-anti-CD3 amino acid sequence as set forth in SEQ ID NO: 66 or 67; or
(d) an alpha chain amino acid sequence as set forth in SEQ ID NO: 49 and a beta chain-anti-CD3 amino acid sequence as set forth in SEQ ID NO: 68 or 69.

Preferably, the binding molecule comprises an alpha chain amino acid sequence as set forth in SEQ ID NO: 49 and a beta chain-anti-CD3 amino acid sequence as set forth in SEQ ID NO: 69. Thus, the invention provides a binding molecule having the property of binding to PYLGQMINL (SEQ ID NO: 1) in complex with HLA-A24, wherein the binding molecule comprises a TCR alpha chain and a TCR beta chain covalently linked to an anti-CD3 scFv, wherein the alpha chain comprises the amino acid sequence set forth in SEQ ID NO: 49 and the beta chain-antiCD3 chain comprises the amino acid sequence set forth in SEQ ID NO: 69.

The binding molecules may be bispecific T cell engaging receptors (TCER®) which are soluble Fc-containing bispecific antigen binding molecules comprising a TCR antigen binding moiety and an antibody antigen binding moiety. The antibody antigen binding moiety is formed by the heavy and light chain variable domains of an antibody. TCER® s comprise two polypeptide chains, wherein the antigen binding sites are formed by variable domains located on different polypeptide chains in a cross-over orientation. Thus, the binding molecule may comprise:
a first polypeptide chain which comprises the TCR alpha chain variable domain and the antibody VH or VL; and
a second polypeptide chain which comprises the TCR beta chain variable domain and the other of the antibody VH and VL,
wherein the respective polypeptide chains associate such that the binding molecule is capable of simultaneously binding the PYLGQMINL (SEQ ID NO: 1) HLA-A24 complex and the antigen of the antibody.

The binding molecules of the invention preferably comprise a protein. The binding molecule may be glycosylated, amidated, carboxylated, phosphorylated, esterified, N-acylated, cyclized via, e.g., a disulfide bridge, or converted into an acid addition salt and/or optionally dimerized or polymerized, or conjugated. All such forms are encompassed by the present invention.

The binding molecules may be synthetic, recombinant, isolated, engineered and/or purified. By "purified" it is meant, when referring to a polypeptide, or nucleotide sequence, that the indicated molecule is present in the substantial absence of other biological macromolecules of the same type. The term "purified" as used herein means that at least 75%, 85%, 95%, or 98% by weight, of biological macromolecules of the same type are the indicated molecule. A purified nucleic acid molecule that encodes a particular polypeptide refers to a nucleic acid molecule that is substantially free of other nucleic acid molecules that do not encode the subject polypeptide; however, the molecule may include some additional bases or moieties, which do not deleteriously affect the basic characteristics of the composition.

The term "isolated" means altered or removed from the natural state. For example, a nucleic acid or a polypeptide naturally present in a living animal is not "isolated," but the same nucleic acid or peptide partially or completely separated from the coexisting materials of its natural state is "isolated". An isolated nucleic acid or protein can exist in substantially purified form, or can exist in a non-native environment such as, for example, a host cell. An isolated binding molecule is substantially free of other binding molecules having different antigenic specificities. Moreover, an isolated binding molecule may be substantially free of other cellular material and/or chemicals.

A "recombinant" molecule is one that has been prepared, expressed, created, or isolated by recombinant means. In this regard, recombinant molecules do not exist in nature.

Amino Acid Sequences

Within the scope of the invention are phenotypically silent variants of any molecule disclosed herein. As used herein the term "phenotypically silent variants" is understood to refer to a variant which incorporates one or more further amino acid changes, including substitutions, insertions and deletions, in addition to those set out above, and which variant has a similar phenotype to the corresponding molecule without said change(s). For the purposes of this invention, phenotype comprises binding affinity ($K_D$ and/or binding half-life) and/or specificity. The phenotype for a soluble binding molecule may include potency of immune activation and purification yield, in addition to binding affinity and specificity. A phenotypically silent variant may have a $K_D$ and/or binding half-life for the PYLGQMINL (SEQ ID NO:

1) HLA-A24 complex within 50%, or more preferably within 30%, 25% or 20%, of the measured $K_D$ and/or binding half-life of the corresponding binding molecule without said change(s), when measured under identical conditions (for example at 25° C. and/or on the same SPR chip). Suitable conditions are further provided in the Examples.

Furthermore, a phenotypically silent variant may retain the same, or substantially the same, therapeutic window between binding to the PYLGQMINL (SEQ ID NO: 1) HLA-A24 complex and binding to one or more alternative peptide-HLA complexes. A phenotypically silent variant may retain the same, or substantially the same, therapeutic window between potency of immune cell activation in response to cells presenting to the PYLGQMINL (SEQ ID NO: 1) HLA-A24 complex and cells presenting one or more alternative off-target peptide-HLA complexes. The therapeutic window may be calculated based on lowest effective concentrations ("LOEL") observed for normal cells and the indication relevant cell line. The therapeutic window may be at least 10 fold different; at least 100 fold difference, at least 1000 fold difference, or more. A phenotypic variant may share the same, or substantially the same recognition motif as determined by sequential mutagenesis techniques discussed further below As is known to those skilled in the art, it may be possible to produce binding molecules that incorporate changes in the variable domains thereof compared to those detailed above without significantly altering the affinity of the interaction with the PYLGQMINL (SEQ ID NO: 1) HLA-A24 complex, and or other functional characteristics. In particular, such silent mutations may be incorporated within parts of the sequence that are known not to be directly involved in antigen binding (e.g. the framework regions and or parts of the CDRs that do not contact the antigen). Such variants are included in the scope of this invention.

Phenotypically silent variants may contain one or more conservative substitutions and/or one or more tolerated substitutions. By tolerated substitutions it is meant those substitutions which do not fall under the definition of conservative as provided below but are nonetheless phenotypically silent. The skilled person is aware that various amino acids have similar properties and thus are 'conservative'. One or more such amino acids of a protein, polypeptide or peptide can often be substituted by one or more other such amino acids without eliminating a desired activity of that protein, polypeptide or peptide.

Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); cysteine and methionine (amino acids having sulphur containing side chains); and serine and threonine (amino acids having hydroxyl-containing side chains). It should be appreciated that amino acid substitutions within the scope of the present invention can be made using naturally occurring or non-naturally occurring amino acids. For example, it is contemplated herein that the methyl group on an alanine may be replaced with an ethyl group, and/or that minor changes may be made to the peptide backbone. Whether or not natural or synthetic amino acids are used, it is preferred that only L-amino acids are present.

Substitutions of this nature are often referred to as "conservative" or "semi-conservative" amino acid substitutions. The present invention therefore extends to use of a molecule comprising any of the amino acid sequences described above but with one or more conservative substitutions and or one or more tolerated substitutions in the sequence, such that the amino acid sequence of the molecule, or any domain or region thereof, has at least 90% identity, such as 90%, 91%, 92%, 93%, 94%, 95%, 96%, 97%, 98%, 99% or 100% identity, to the sequences disclosed herein.

"Identity" as known in the art is the relationship between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. While there exist a number of methods to measure identity between two polypeptide or two polynucleotide sequences, methods commonly employed to determine identity are codified in computer programs. Preferred computer programs to determine identity between two sequences include, but are not limited to, GCG program package (Devereux, et al., Nucleic Acids Research, 12, 387 (1984), BLASTP, BLASTN, and FASTA (Atschul et al., J. Molec. Biol. 215, 403 (1990)).

One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of identity analysis are contemplated in the present invention.

The percent identity of two amino acid sequences or of two nucleic acid sequences is determined by aligning the sequences for optimal comparison purposes (e.g., gaps can be introduced in the first sequence for best alignment with the sequence) and comparing the amino acid residues or nucleotides at corresponding positions. The "best alignment" is an alignment of two sequences which results in the highest percent identity. The percent identity is determined by the number of identical amino acid residues or nucleotides in the sequences being compared (i.e., % identity=number of identical positions/total number of positions×100).

The determination of percent identity between two sequences can be accomplished using a mathematical algorithm known to those of skill in the art. An example of a mathematical algorithm for comparing two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. The BLASTn and BLASTp programs of Altschul, et al. (1990) J. Mol. Biol. 215:403-410 have incorporated such an algorithm. Determination of percent identity between two nucleotide sequences can be performed with the BLASTn program. Determination of percent identity between two protein sequences can be performed with the BLASTp program. To obtain gapped alignments for comparison purposes, Gapped BLAST can be utilised as described in Altschul et al. (1997) Nucleic Acids Res. 25:3389-3402. Alternatively, PSI-Blast can be used to perform an iterated search which detects distant relationships between molecules (Id.). When utilising BLAST, Gapped BLAST, and PSI-Blast programs, the default parameters of the respective programs (e.g., BLASTp and BLASTp) can be used. See http://www.ncbi.nlm.nih.gov. Default general parameters may include for example, Word Size=3, Expect Threshold=10. Parameters may be selected to automatically adjust for short input sequences. Another example of a mathematical algorithm utilised for the comparison of sequences is the algorithm of Myers and Miller, CABIOS (1989). The ALIGN program (version 2.0) which is part of the CGC sequence alignment software package has incorporated such an algorithm. Other algorithms for sequence analysis known in the art include ADVANCE and ADAM as described in Torellis and Robotti (1994) Comput. Appl. Biosci., 10:3-5; and FASTA described in Pearson and Lipman (1988) Proc. Natl. Acad. Sci. 85:2444-8. Within FASTA, ktup is a control option that sets the sensitivity and speed of the search. For the purposes of evaluating percent identity in the present disclosure, BLASTp with the default parameters is used as the comparison methodology. In addition, when the recited percent identity provides a non-whole number value for amino acids (i.e., a sequence of 25 amino acids having 90% sequence identity provides a value of "22.5", the obtained value is rounded down to the next whole number, thus "22"). Accordingly, in the example provided, a sequence having 22 matches out of 25 amino acids is within 90% sequence identity.

As will be obvious to those skilled in the art, it may be possible to truncate, or extend, the sequences provided at the C-terminus and/or N-terminus thereof, by 1, 2, 3, 4, 5 or more residues, without substantially affecting the functional characteristics of the molecule, for example a TCR portion. The sequences provided at the C-terminus and/or N-terminus thereof may be truncated or extended by 1, 2, 3, 4 or 5 residues. All such variants are encompassed by the present invention.

Mutations, including conservative and tolerated substitutions, insertions and deletions, may be introduced into the sequences provided using any appropriate method including, but not limited to, those based on polymerase chain reaction (PCR), restriction enzyme-based cloning, or ligation independent cloning (LIC) procedures. These methods are detailed in many of the standard molecular biology texts. For further details regarding polymerase chain reaction (PCR) and restriction enzyme-based cloning, see Sambrook & Russell, (2001) Molecular Cloning—A Laboratory Manual ($3^{rd}$ Ed.) CSHL Press. Further information on ligation independent cloning (LIC) procedures can be found in Rashtchian, (1995) *Curr Opin Biotechnol* 6(1): 30-6. The protein sequences provided herein may be obtained from recombinant expression, solid state synthesis, or any other appropriate method known in the art.

Assessing Binding Characteristics and Activity of Binding Molecules

Methods to determine binding affinity (inversely proportional to the equilibrium constant $K_D$) and binding half-life (expressed as T½) are known to those skilled in the art. Binding affinity and binding half-life may be determined using Surface Plasmon Resonance (SPR) or Bio-Layer Interferometry (BLI), for example using a BIAcore instrument or Octet instrument, respectively. For example, binding affinity of a binding molecule for a peptide-HLA complex may be determined using SPR at 25° C., wherein the peptide-HLA complex is immobilised on a solid support (e.g., a sensor chip) and is contacted with a solution comprising the binding molecule. Suitable experimental conditions and methods for determining binding parameters are described in Example 1.

It will be appreciated by those skilled in the art that a higher affinity refers to a lower numerical value for $K_D$ and indicates stronger binding. In other words, a doubling of affinity refers to halving the numerical value of the $K_D$. T½ is calculated as In2 divided by the off-rate ($K_{off}$). Therefore, doubling of T½ results in a halving in $K_{off}$. $K_D$ and $K_{off}$ values for TCRs are usually measured for soluble forms of the TCR, i.e. those forms which are truncated to remove cytoplasmic and transmembrane domain residues. To account for variation between independent measurements, and particularly for interactions with dissociation times in excess of 20 hours, the binding affinity and or binding half-life of a given protein may be measured several times, for example 3 or more times, using the same assay protocol, and an average of the results taken. To compare binding data between two samples (i.e. two different proteins and or two preparations of the same protein) it is preferable that measurements are made using the same assay conditions (e.g. temperature). Measurement methods described in relation to TCRs may also be applied to the binding molecules described herein.

Certain binding molecules of the invention are able to generate a highly potent T cell response in vitro against antigen positive cells, in particular those cells presenting low levels of antigen typical of cancer cells (i.e. in the order of 5-100, for example 50, antigens per cell (Bossi et al., (2013) Oncoimmunol. 1; 2 (11):e26840; Purbhoo et al., (2006). J Immunol 176(12): 7308-7316.). Such TCRs may be suitable for incorporation into the binding molecules described herein. The T cell response that is measured may be the release of T cell activation markers such as Interferon γ or Granzyme B, or target cell killing, or other measure of T cell activation, such as T cell proliferation. A highly potent response may be one with an $EC_{50}$ value in the nM-pM range, for example 500 nM or lower, preferably 1 nM or lower, or 500 pM or lower.

Molecules encompassed by the present invention may have an improved half-life. Methods for determining whether a protein has an improved half-life will be apparent to the skilled person. For example, the ability of a protein to bind to a neonatal Fc receptor (FcRn) is assessed. In this regard, increased binding affinity for FcRn increases the serum half-life of the protein (see for example, Kim et al. Eur J Immunol., 24:2429, 1994).

The half-life of a protein disclosed herein can also be measured by pharmacokinetic studies, e.g., according to the method described by Kim et al. Eur J of Immunol 24: 542, 1994. According to this method radiolabeled protein is injected intravenously into mice and its plasma concentration is periodically measured as a function of time, for example at 3 minutes to 72 hours after the injection. Alternatively, unlabelled protein of the disclosure can be injected and its plasma concentration periodically measured using an ELISA. The clearance curve thus obtained should be biphasic, that is, an alpha phase and beta phase. For the determination of the in vivo half-life of the protein, the clearance rate in beta-phase is calculated and compared with that of the wild type or unmodified protein.

Structural characteristics of a binding molecule described herein, such as crossing angle, tilt angle, roll angle, and peptide residue binding contacts may be determined. Methods to determine such structural characteristics may comprise determining, for example, a three-dimensional atomic structure of a binding molecule bound to the PYLGQMINL (SEQ ID NO: 1) HLA-A24 complex.

As used herein, the term "three-dimensional atomic structure" refers to a model of the three-dimensional arrangement of atoms of a protein or protein complex. The three-dimensional atomic structure may be based on a set of atomic coordinates. As used herein, the term "atomic coordinates" or "set of coordinates" refers to a set of values which define the position of one or more atoms in a protein with reference to a system of axes. The atomic coordinates may be used in a computer to generate a representation, e.g. an image of the three-dimensional structure of proteins which can be displayed by the computer and/or represented in an electronic file. Such atomic structures may be determined using techniques well known in the art, including x-ray crystallography, nuclear magnetic resonance (NMR) or cryo-electron microscopy (cryo-EM). For example, the three-dimensional atomic structure may be an x-ray crystal structure. An x-ray crystal structure is a three-dimensional atomic structure of a protein or protein complex that is obtained using x-ray crystallography. X-ray crystallography techniques are well known in the art. A suitable technique is described in Example 7 under the heading "X-ray crystallography".

An x-ray crystal structure may be obtained by an x-ray crystallography technique known as molecular replacement. Methods of molecular replacement are generally known by those skilled in the art and can be performed using publicly available software packages. Generally, molecular replacement involves the following steps: i) X-ray diffraction data are collected from a crystal of a crystallized target protein complex, then ii) the X-ray diffraction data are transformed to calculate a Patterson function, then iii) the Patterson function of the crystallized target structure is compared with a Patterson function calculated from one or more known structures (referred to in the art as a "search structure" or "search model"), iv) the Patterson function of the search structure is rotated on the target structure Patterson function to determine the correct orientation of the search structure in the crystal to obtain a rotation function, v) a translation function is then calculated to determine the location of the search structure with respect to the crystal axes. Alternatively, likelihood-based molecular replacement methods can be used to determine the location of the search structure. Once the search structure has been correctly positioned in the unit cell, initial phases for the experimental data can be calculated. These phases are necessary for calculation of an electron density map from which an initial three-dimensional atomic structure is determined and refined. Preferably, the structural features (e.g., amino acid sequence, conserved disulfide bonds, and beta-strands or beta-sheets) of the search models are related to the crystallized target complex. Suitable search models can be obtained from a protein structure database such as the RCSB Protein Data Bank (RCSB PDB). Suitable search models for determining the three-dimensional atomic structure of a complex formed by the pHLA and a binding molecule include the atomic coordinates of known TCR and pHLA structures. The electron density map can, in turn, be subjected to any well-known model building and structure refinement techniques to provide a final, accurate structure of the unknown (i.e. target) crystallized molecular structure.

Once a three-dimensional atomic structure of the binding molecule bound to the pHLA complex is obtained, structural characteristics such as the binding geometry (e.g., crossing, roll and tilt angles) and peptide residue binding contacts can be determined, based on the positions of the atoms in the structure.

The "pHLA crossing angle" or "crossing angle" (also known in the art as "docking angle") is a parameter known in the art for TCRs (see Rudolph et al. (2006) Annu. Rev. Immunol. 24:419). Specifically, the crossing angle is the angle formed between two vectors: a HLA groove vector and a TCR interdomain vector (also referred to herein as the "TCR cystine vector").

The HLA groove vector (also referred to as the "HLA peptide-binding groove vector") is the directed line segment (or vector) corresponding to the peptide positioned across the HLA peptide binding groove, i.e., from N to C-terminus of the peptide. In this regard, the HLA groove vector follows the two parallel HLA groove helices with the direction N-terminus to C-terminus of HLA helix 1 and passing through the HLA centroid. The TCR interdomain vector is the directed line segment (or vector) connecting the intrachain disulfide bond in the TCR alpha chain variable domain to the intrachain disulfide bond in the TCR beta chain variable domain (in the direction of alpha chain to beta chain).

Similarly the "tilt angle" of a binding molecule is the angle between a "TCR symmetry vector" and the HLA groove vector. The TCR symmetry vector represents the pseudo-two-fold symmetry axis of the TCR variable subunits and points in direction of its CDRs and passes through the TCR centroid.

The "roll angle" of a binding molecule is the angle formed between a "second HLA vector" or "HLA v2 vector" and the TCR symmetry vector. The second HLA vector (HLA v2 vector) is generated perpendicular to the HLA groove vector and points from HLA helix 1 to HLA helix 2. The two vectors meet at the centroid of the HLA helices.

Methods for calculating the above angles are known in the art and include those described by Rudolph et al. (2006) Annu. Rev. Immunol. 24:419 and Mareeva et al. (2006) JBC 283:29053.

A binding molecule of the invention may be assessed to determine its peptide residue binding contacts. The phrase "peptide residue binding contacts" refers to binding interactions formed between amino acid residues of the peptide within the peptide-HLA complex (not the HLA) and amino acid residues of the binding molecule. Each peptide residue that is contacted by the binding molecule, when the binding molecule is bound to the pHLA complex, is considered to be a peptide residue binding contact. For example, there may be 4, 5, 6, 7 or 8 or more, peptide residue binding contacts. Of these peptide reside binding contacts, there may be a minimum number (e.g., 4, 5, 6, 7 or 8) that are sufficient for specific binding of the binding molecule to the pHLA complex.

Amino acid residue binding contacts can be determined using any method known in the art and may comprise measuring distances between atoms in a three-dimensional atomic structure of the binding molecule bound to the pHLA complex. For example, residues in the binding molecule and the peptide may be identified to be in binding contact if the distance between any atom from a binding molecule residue and any atom from a peptide residue is equal to 4.1 Å or less. Alternatively, or additionally, binding interactions (e.g., peptide residue binding contacts) can be identified from the three-dimensional atomic structure based on known atomic interaction geometry for different types of interactions, e.g., hydrogen bonds (H-bond), electrostatic interactions, van de Waals (vdW) interactions. For example, an H-bond binding contact can be defined as an interaction between donor atom and acceptor atom, where the donor-acceptor distance in the three-dimensional atomic structure is about 3.0 Å or less, and the donor hydrogen acceptor angle is within 45° to 180°. A vdW binding contact can defined as an interaction between two heavy atoms which are within about 4 Å of one another in the three-dimensional atomic structure. Methods of identifying peptide residue binding contacts may comprise performing molecular dynamics simulations using publicly available software packages.

Nucleic Acids, Vectors and Host Cells

The present invention provides a nucleic acid encoding a binding molecule of the invention. The TCR alpha and beta chain variable domains of the binding molecule may be encoded within a single open reading frame, or within two distinct open reading frames. Alternatively, the TCR alpha and beta chain variable domains of the binding molecule may be encoded on separate nucleic acids. The term "nucleic acid" includes but is not limited to ribonucleic acid (RNA) and deoxyribonucleic acid (DNA) molecules, which may be single or double stranded. The nucleic acid may be present in whole cells, in a cell lysate, or may be in an isolated, partially purified or substantially pure form. A nucleic acid is "isolated" or "rendered substantially pure" when purified away from other cellular components or other contaminants, e.g., other cellular nucleic acids or proteins, by standard techniques. The nucleic acid may be recombinant and/or non-naturally occurring and/or engineered. The nucleic acid sequence may be codon optimised, in accordance with the expression system utilised. As is known to those skilled in the art, expression systems may include bacterial cells such as E. coli, or yeast cells, or mammalian cells, or insect cells, or they may be cell free expression systems.

The present invention also provides constructs in the form of plasmids, vectors, transcription or expression cassettes which comprise at least one nucleic acid as described above. In particular, the invention provides an expression vector comprising the nucleic acid of the invention. The terms "vector", "cloning vector" and "expression vector" refer to a vehicle by which a DNA or RNA sequence (e.g. a foreign gene) can be introduced into a host cell, so as to transform the host and optionally promote expression (e.g. transcription and translation) of the introduced sequence.

The present invention also provides a recombinant host cell which comprises one or more the constructs as above. As mentioned, a nucleic acid encoding a binding molecule of the invention forms an aspect of the present invention, as does a method of production of the binding molecule comprising expression from a nucleic acid encoding a binding molecule of the invention. Expression may conveniently be achieved by culturing recombinant host cells containing the nucleic acid under appropriate conditions. Following production by expression, a binding molecule may be isolated and/or purified using any suitable technique, then used as appropriate.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, Hela cells, baby hamster kidney cells, NSO mouse melanoma cells and many others. A common, preferred bacterial host is E. coli. The expression of antibodies and antibody fragments in prokaryotic cells such as E. coli is well established in the art. For a review, see for example Pluckthun, Bio/Technology 9:545-551 (1991). Expression in eukaryotic cells in culture is also available to those skilled in the art as an option for production of a binding molecule, see for recent review, for example Reff, Curr. Opinion Biotech. 4:573-576 (1993); Trill et al., Curr. Opinion Biotech. 6:553-560 (1995).

Suitable vectors can be chosen or constructed, containing appropriate regulatory sequences, including promoter sequences, terminator sequences, polyadenylation sequences, enhancer sequences, marker genes and other sequences as appropriate. Vectors may be any suitable vectors known in the art, including plasmids or viral vectors (e.g. 'phage, or phagemid), as appropriate. For further details see, for example, Sambrook et al., Molecular Cloning: A Laboratory Manual: 2nd Edition, Cold Spring Harbor Laboratory Press (1989). Many known techniques and protocols for manipulation of nucleic acid, for example in preparation of nucleic acid constructs, mutagenesis, sequencing, introduction of DNA into cells and gene expression, and analysis of proteins, are described in detail in Ausubel et al. eds., Short Protocols in Molecular Biology, 2nd Edition, John Wiley & Sons (1992).

The present invention also provides a host cell containing a nucleic acid as disclosed herein. The invention also provides a cell harbouring
  (a) an expression vector of the invention; or
  (b) a first expression vector comprising a nucleic acid encoding a first polypeptide comprising the TCR alpha chain variable domain of a binding molecule of the invention and a second expression vector comprising a nucleic acid encoding a second polypeptide comprising the TCR beta chain variable domain of a binding molecule of the invention. Also provided is a non-naturally occurring and/or purified and/or engineered cell, preferably a T-cell, presenting the binding molecule of the invention.

Further, the invention provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g. by culturing host cells under conditions for expression of the gene.

Suitable host cells for cloning or expression of polynucleotides and/or vectors of the present invention are known in the art. Suitable host cells for the expression of (glycosylated) proteins are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells. Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham, F. L. et al., J. Gen Virol. 36 (1977) 59-74); baby hamster kidney cells (BHK); mouse Sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells (as described, e.g., in Mather, J. P. et al., Annals N.Y. Acad. Sci. 383 (1982) 44-68); MRC 5 cells; and FS4 cells. Other useful mammalian host cell lines include Chinese hamster ovary (CHO) cells, including DHFR-CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for protein production, see, e.g., Yazaki, P. and Wu, A. M., Methods in Molecular Biology, Vol. 248, Lo, B. K. C. (ed.), Humana Press, Totowa, NJ (2004), pp. 255-268. The host cell may be eukaryotic, e.g., a Chinese Hamster Ovary (CHO) cell or lymphoid cell (e.g., Y0, NS0, Sp20 cell). Alternatively, the host cell may be prokaryotic, e.g., an E. coli cell.

The nucleic acid of the invention may be integrated into the genome (e.g. chromosome) of the host cell. Integration may be promoted by inclusion of sequences which promote recombination with the genome, in accordance with standard techniques.

Methods of Making Binding Molecules

Further provided herein are methods for producing a binding molecule of the invention. In one aspect, the methods comprise a) maintaining a cell of the invention under conditions suitable for expression of the binding molecule, and b) isolating the binding molecule. In another aspect, the methods comprise
- a) providing a first cell capable of expressing a first polypeptide comprising the TCR alpha chain variable domain of a binding molecule of the invention and a second cell capable of expressing a second polypeptide comprising the TCR beta chain variable domain of a binding molecule of the invention;
- b) maintaining the first cell under conditions suitable for expression of the first polypeptide and maintaining the second cell under conditions suitable for expression of the second polypeptide;
- c) isolating the first and second polypeptides from the cells; and
- d) complexing the first and second polypeptides to form the binding molecule of the invention.

Methods of producing recombinant proteins are well known in the art. Nucleic acids encoding the protein can be cloned into expression constructs or vectors, which are then transfected into host cells, such as E. coli cells, yeast cells, insect cells, or mammalian cells, such as simian COS cells, Chinese Hamster Ovary (CHO) cells, human embryonic kidney (HEK) cells, or myeloma cells that do not otherwise produce the protein. Exemplary mammalian cells used for expressing a protein are CHO cells, myeloma cells or HEK cells. Preferred cells for producing the binding molecules of the invention are E. coli cells. Molecular cloning techniques to achieve these ends are known in the art and described, for example in Ausubel et al. (editors), Current Protocols in Molecular Biology, Greene Pub. Associates and Wiley-Interscience (1988, including all updates until present) or Sambrook et al. Molecular Cloning: A Laboratory Manual, Cold Spring Harbor Laboratory Press (1989). A wide variety of cloning and in vitro amplification methods are suitable for the construction of recombinant nucleic acids. Methods of producing recombinant antibodies are also known in the art, see, e.g., U.S. Pat. No. 4,816,567 or 5,530,101.

The nucleic acid may be inserted operably linked to a promoter in an expression construct or expression vector for further cloning (amplification of the DNA) or for expression in a cell-free system or in cells. As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid. As used herein, the term "operably linked to" means positioning a promoter relative to a nucleic acid such that expression of the nucleic acid is controlled by the promoter.

Many vectors for expression in cells are commercially available. The vector components generally include, but are not limited to, one or more of the following: a signal sequence, a sequence encoding a protein (e.g., derived from the information provided herein), an enhancer element, a promoter, and a transcription termination sequence. The skilled person will be aware of suitable sequences for expression of a protein. Exemplary signal sequences include prokaryotic secretion signals (e.g., pelB, alkaline phosphatase, penicillinase, lpp, or heat-stable enterotoxin II), yeast secretion signals (e.g., invertase leader, a factor leader, or acid phosphatase leader) or mammalian secretion signals (e.g., herpes simplex gD signal).

Exemplary promoters active in mammalian cells include cytomegalovirus immediate early promoter (CMV-IE), human elongation factor 1-a promoter (EF1), small nuclear RNA promoters (Ula and Ulb), α-myosin heavy chain promoter, Simian virus 40 promoter (SV40), Rous sarcoma virus promoter (RSV), Adenovirus major late promoter, β-actin promoter; hybrid regulatory element comprising a CMV enhancer/β-actin promoter or an immunoglobulin promoter or an active fragment thereof. Examples of useful mammalian host cell lines are monkey kidney CV1 line transformed by SV40 (COS-7, ATCC CRL 1651); human embryonic kidney line (293 or 293 cells subcloned for growth in suspension culture); baby hamster kidney cells (BHK, ATCC CCL 10); or Chinese hamster ovary cells (CHO).

Typical promoters suitable for expression in yeast cells such as for example a yeast cell selected from the group comprising Pichia pastoris, Saccharomyces cerevisiae and S. pombe, include, but are not limited to, the ADH1 promoter, the GAL1 promoter, the GALA promoter, the CUP1 promoter, the PH05 promoter, the nmt promoter, the RPR1 promoter, or the TEF1 promoter.

The host cells used to produce the protein may be cultured in a variety of media, depending on the cell type used. Commercially available media such as Ham's F10 (Sigma), Minimal Essential Medium ((MEM), (Sigma), RPM1-1640 (Sigma), and Dulbecco's Modified Eagle's Medium ((DMEM), Sigma) are suitable for culturing mammalian cells. Media for culturing other cell types discussed herein are known in the art.

Methods for isolating a protein are known in the art. Where a protein is secreted into culture medium, supernatants from such expression systems can be first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants. Alternatively, or additionally, supernatants can be filtered and/or separated from cells expressing the protein, e.g., using continuous centrifugation.

The protein prepared from the cells can be purified using, for example, ion exchange, hydroxyapatite chromatography, hydrophobic interaction chromatography, gel electrophoresis, dialysis, affinity chromatography (e.g., protein A affinity chromatography or protein G chromatography), or any combination of the foregoing.

These methods are known in the art and described, for example in WO99/57134 or Ed Harlow and David Lane (editors) Antibodies: A Laboratory Manual, Cold Spring Harbor Laboratory, (1988). The skilled person will also be aware that a protein can be modified to include a tag to facilitate purification or detection, e.g., a poly-histidine tag, a hexa-histidine tag, an influenza virus hemagglutinin (HA) tag, a Simian Virus 5 (V5) tag, a LLAG tag, or a glutathione S-transferase (GST) tag. The resulting protein is then purified using methods known in the art, such as, affinity purification.

For example, a protein comprising a hexa-his tag is purified by contacting a sample comprising the protein with nickel-nitrilotriacetic acid (Ni-NTA) that specifically binds a hexa-his tag immobilized on a solid or semi-solid support, washing the sample to remove unbound protein, and subsequently eluting the bound protein. Alternatively, or in addition a ligand or antibody that binds to a tag is used in an affinity purification method.

Molecules of the invention may be amenable to high yield purification. Yield may be determined based on the amount of material retained during the purification process (i.e. the amount of correctly folded material obtained at the end of the purification process relative to the amount of solubilised material obtained prior to refolding), and or yield may be based on the amount of correctly folded material obtained at the end of the purification process, relative to the original culture volume. High yield means greater than 1%, or greater than 5%, or higher yield. High yield means greater than 1 mg/ml, or greater than 3 mg/ml, or greater than 5 mg/ml, or higher yield.

Pharmaceutical Compositions and Medical Methods

For administration to patients, the molecules of the invention, nucleic acids, expression vectors or cells of the invention may be provided as part of a pharmaceutical composition together with one or more pharmaceutically acceptable carriers or excipients (for example a buffering agent, also known as a "buffer"). This pharmaceutical composition may be in any suitable form, (e.g. depending upon the desired method of administering it to a patient). It may be provided in unit dosage form, and will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, such as parenteral (including subcutaneous, intramuscular, intrathecal or intravenous), enteral (including oral or rectal), inhalation or intranasal routes. Such compositions may be prepared by any method known in the art of pharmacy, for example by mixing the active ingredient with the carrier(s) or excipient(s) under sterile conditions. Methods for preparing a protein into a suitable form for administration to a subject (e.g. a pharmaceutical composition) are known in the art and include, for example, methods as described in Remington's Pharmaceutical Sciences (18th ed., Mack Publishing Co., Easton, Pa., 1990) and U.S. Pharmacopeia: National Formulary (Mack Publishing Company, Easton, Pa., 1984).

The pharmaceutical compositions will commonly comprise a solution of the binding molecule of the invention (or the nucleic acid, cell, or vector of the invention) dissolved in a pharmaceutically acceptable carrier, for example an aqueous carrier. A variety of aqueous carriers can be used, e.g., buffered saline and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of molecules of the present invention in these formulations can vary widely, and will be selected primarily based on fluid volumes, viscosities, body weight and the like in accordance with the particular mode of administration selected and the patient's needs. Exemplary carriers include water, saline, Ringer's solution, dextrose solution, and 5% human serum albumin. Nonaqueous vehicles such as mixed oils and ethyl oleate may also be used. Liposomes may also be used as carriers. The vehicles may contain minor amounts of additives that enhance isotonicity and chemical stability, e.g., buffers and preservatives.

Binding molecules, pharmaceutical compositions, vectors, nucleic acids and cells of the invention may be provided in substantially pure form, for example, at least 80%, at least 85%, at least 90%, at least 91%, at least 92%, at least 93%, at least 94%, at least 95%, at least 96%, at least 97%, at least 98%, at least 99% or 100% pure.

Binding molecules of the invention may have an ideal safety profile for use as therapeutic reagents. "Safety profile", as used herein, refers to the capacity to distinguish a tumor cell, in particular a PYLGQMINL (SEQ ID NO: 1)-HLA-A24 complex presenting tumor cell, from a healthy cell. This capacity is often expressed by indication of a safety window. In this case the binding molecules may be in soluble form and may preferably be fused to an immune effector. Suitable immune effectors are described herein and include but are not limited to, cytokines, such as IL-2 and IFN-γ; superantigens and mutants thereof; chemokines such as IL-8, platelet factor 4, melanoma growth stimulatory protein; antibodies and antibody like scaffolds, including fragments, derivatives and variants thereof that bind to antigens on immune cells such as T cells or NK cell (e.g. anti-CD3, anti-CD28 or anti-CD16); and Fc receptor or complement activators. An ideal safety profile means that in addition to demonstrating good specificity, the binding molecules of the invention may have passed further preclinical safety tests. Examples of such tests include whole blood assays to confirm minimal cytokine release in the presence of whole blood and thus low risk of causing a potential cytokine release syndrome in vivo, and alloreactivity tests to confirm low potential for recognition of alternative HLA types.

Suitable dosages of the molecules of the present invention can vary between wide limits, depending upon the disease or disorder to be treated, the age and condition of the subject to be treated, etc. Preferably, the subject is a human. A physician may ultimately determine appropriate dosages to be used. Administration of the TCR anti-CD3 fusion molecule may be in a "therapeutically effective amount," this being an amount sufficient to show benefit to the patient.

The binding molecule of the invention may be further associated with a therapeutic agent. Therapeutic agents which may be associated with the molecules of the invention include immune-modulators and effectors, radioactive compounds, enzymes (perforin for example) or chemotherapeutic agents (cis-platin for example). To ensure that toxic effects are exercised in the desired location the toxin could be inside a liposome linked to the binding molecule described herein so that the compound is released slowly. This will prevent damaging effects during the transport in the body and ensure that the toxin has maximum effect after binding of the binding molecule described herein to the relevant antigen presenting cells.

The binding molecule, nucleic acid, vector, pharmaceutical composition and cell of the invention may be used for treating diseases such as cancer. The cancer to be treated may be a cancer associated with PRAME expression. By "associated with PRAME expression" it is meant that the cancer comprises cancer cells that express PRAME. In this regard, the cancer may be a PRAME-positive cancer. The cancer may be known to be associated with expression of PRAME. For example, it may be known that the prevalence of PRAME expression is elevated in the cancer and thus PRAME expression may not be assessed, or may be assessed retrospectively. Alternatively, PRAME expression can be assessed using any method known in the art, including, for example, histological methods or other quantitative or qualitative measurements, including PCR, RNA expression analysis, and/or kits or sequence panels designed to measure the expression level of PRAME. The invention is not intended to be limited to the treatment of cancers for which PRAME expression can be detected by histological methods. Rather, the binding molecules of the invention may be useful for the treatment of cancers and tumour types which are considered to be associated with PRAME expression.

PRAME expression, when detected by histological methods like immunohistochemistry (IHC), can be quantified using an H-score. Expression of PRAME in individual cells or their sub-cellular compartments within a tumour are first detected and classified as either positive or negative. The positive cells can be further classified into high, medium, or low based on the IHC signal intensity. The H-score captures both the intensity and the proportion of the biomarker of interest from the IHC image and comprises values between 0 and 300, thereby offering a dynamic range to quantify abundance or a particular marker or gene.

Cancers associated with PRAME expression include, but are not limited to, melanoma, lung cancer, breast cancer, ovarian cancer, endometrial cancer, oesophageal cancer, bladder cancer, head and neck cancer, uterine cancer, Acute myeloid leukemia, chronic myeloid leukemia, and Hodgkin's lymphoma. For example, the cancer associated with PRAME expression may be melanoma. The melanoma may be uveal melanoma or cutaneous melanoma. The lung cancer may be non-small cell lung carcinoma (NSCLC) or small cell lung cancer (SCLC). The breast cancer may be triple-negative breast cancer (TNBC). The bladder cancer may be urothelial carcinoma. The oesophageal cancer may be gastroesophageal junction (GEJ) adenocarcinoma. The ovarian cancer may be epithelial ovarian cancer, such as high grade serous ovarian cancer. In particular, the cancer may be cutaneous melanoma, ovarian cancer, NSCLC or endometrial cancer.

The antigen PRAME constitutes a cancer marker and, therefore, has the potential to be used to indicate the effectiveness of an anti-cancer therapy or detecting recurrence of the disease. Thus, in another aspect, the invention provides the binding molecule, the nucleic acid, the vector, the host cell, or the pharmaceutical composition of the invention, for use as a diagnostic agent, in particular for use as an in vivo diagnostic agent. In preferred embodiments, the diagnostic agent is for the diagnosis of a proliferative disease. In more preferred embodiments, the diagnostic agent is for the diagnosis of a cancer that presents a peptide comprising or consisting of the amino acid sequence of PYLGQMINL (SEQ ID NO: 1) in complex with HLA-A24.

Also provided by the invention are:
- a binding molecule, nucleic acid, vector, pharmaceutical composition or cell of the invention for use in medicine, preferably for use in a human subject and/or preferably for use in a method of treating cancer or a tumour;
- use of a binding molecule, nucleic acid, vector, pharmaceutical composition or cell of the invention in the manufacture of a medicament for treating cancer or a tumour;
- a method of treating cancer or a tumour in a patient, comprising administering to the patient a binding molecule, nucleic acid, vector, pharmaceutical composition or cell of the invention;
- an injectable formulation for administering to a human subject comprising a binding molecule, nucleic acid, vector pharmaceutical composition or cell of the invention.

Kits and Articles of Manufacture

In another aspect, a kit or an article of manufacture containing materials useful for the treatment and/or prevention of the diseases described above is provided.

The kit may comprise (a) a container comprising the binding molecule, nucleic acid, vector or cell of the invention, optionally in a pharmaceutically acceptable carrier or diluent; and (b) a package insert with instructions for treating a disease (e.g., cancer) in a subject. The kit may further comprise (c) at least one further therapeutically active compound or drug.

The package insert may be on or associated with the container. Suitable containers include, for example, bottles, vials, syringes, etc. The containers may be formed from a variety of materials such as glass or plastic. The container holds or contains a composition that comprises the molecule, nucleic acid, vector or cell of the invention and may have a sterile access port (for example, the container may be an intravenous solution bag or a vial having a stopper pierceable by a hypodermic injection needle). At least one active agent in the composition is the binding molecule, nucleic acid, vector or cell of the invention. The label or package insert indicates that the composition is used for treating a subject eligible for treatment, e.g., one having or predisposed to developing a disease described herein, with specific guidance regarding dosing amounts and intervals of the composition and any other medicament being provided. The kit may further comprise an additional container comprising a pharmaceutically acceptable diluent buffer, such as bacteriostatic water for injection (BWFI), phosphate-buffered saline, Ringer's solution, and/or dextrose solution. The kit may further include other materials desirable from a commercial and user standpoint, including other buffers, diluents, filters, needles, and syringes.

The invention also includes particles displaying binding molecules of the invention and the inclusion of said particles within a library of particles. Such particles include but are not limited to phage, yeast cells, ribosomes, or mammalian cells. Method of producing such particles and libraries are known in the art (for example see WO2004/044004; WO01/48145, Chervin et al. (2008) J. Immuno. Methods 339.2: 175-184).

Various modifications of the invention in addition to those shown and described herein will become apparent to those skilled in the art from the foregoing description and fall within the scope of the appended claims. Preferred features of each aspect of the invention are as for each of the other aspects mutatis mutandis. The documents referred to herein are incorporated by reference to the fullest extent permitted by law.

FIG. 5 is a series of bar charts showing levels of T cell activation induced by selected TCR-anti-CD3 fusion molecules for normal cells from healthy tissues, as described in Example 5.

FIG. 6 a series of line graphs showing levels of T cell activation induced by selected TCR-anti-CD3 fusion molecules for various cancer cell lines, as described in Example 6.

FIG. 7 is an image of an x-ray crystal structure of the TCR-peptide interface formed by the TCR "S11" when bound to PYLGQMINL (SEQ ID NO: 1) in complex with HLA-A24. Key residue changes introduced during affinity maturation are indicated.

FIG. 8 is an image of the computationally modelled structure of TCR-peptide interface formed by the TCR variant a90b152 when bound to PYLGQMINL (SEQ ID NO: 1) in complex with HLA-A24. Key residue changes introduced during affinity maturation are labelled.

DESCRIPTION OF THE SEQUENCES

HLA-A24 Restricted Peptides

Source protein gene is indicated in brackets below.

SEQ ID NO: 1 (PRAME):
PYLGQMINL

SEQ ID NO: 81 (PLEC):
PYTGQQISL

SEQ ID NO: 82 (SYNRG):
PYLGQAPFL

-continued

SEQ ID NO: 83 (PLCB4):
PYLSTMINY

SEQ ID NO: 84 (LSM14B):
PYLGSKISL

Alpha Chain of an Exemplary Scaffold TCR (SEQ ID NO: 2)

SEQ ID NO: 2 is an amino acid sequence of the alpha chain of an exemplary wild type (e.g., "scaffold") TCR (comprising the alpha chain of SEQ ID NO: 2 and the beta chain of SEQ ID NO: 12) that binds to PYLGQMINL (SEQ ID NO: 1) in complex with HLA-A24. This TCR is referred to as "S11" herein. The alpha chain comprises a variable domain (SEQ ID NO: 3) and a constant domain (SEQ ID NO: 4, italics). CDRs (CDR1, CDR2 and CDR3) are underlined and are designated SEQ ID NO: 5, 6 and 7 respectively, framework regions (FR1, FR2, FR3 and FR4) are in regular text and are designated SEQ ID NO: 8, 9, 10 and 11 respectively. The constant domain includes a T48C (numbered according to SEQ ID NO: 4) mutation (relative to a wild type constant domain), in bold text, to introduce a non-native covalent disulfide bond between the alpha and beta chains.

SEQ ID NO: 2:
AQSVTQLDSHVSVSEGTPVLLRCNYSSSYSPSLFWYVQHP
NKGLQLLLKYTSAATLVKGINGFEAEFKKSETSFHLTKPS
AHMSDAAEYFCVVSAPNRDDKIIFGKGTRLHILPNIQNPD
PAVYQLRDSKSSDKSVCLFTDFDSQTNVSQSKDSDVYITD
KCVLDMRSMDFKSNSAVAWSNKSDFACANAFNNSIIPEDT

Beta Chain of an Exemplary Scaffold TCR (SEQ ID NO: 12)

SEQ ID NO: 12 is an amino acid sequence of the beta chain of an exemplary wild type (e.g., "scaffold") TCR (comprising the alpha chain of SEQ ID NO: 2 and the beta chain of SEQ ID NO: 12) that binds to PYLGQMINL (SEQ ID NO: 1) in complex with HLA-A24. This TCR is referred to as "S11" herein. The beta chain comprises a variable domain (SEQ ID NO: 13) and a constant domain (SEQ ID NO: 14, italics). CDRs (CDR1, CDR2 and CDR3) are underlined and are designated SEQ ID NO: 15, 16 and 17 respectively, framework regions (FR1, FR2, FR3 and FR4) are in regular text and are designated SEQ ID NO: 18, 19, 20 and 21 respectively. The constant domain includes a S57C (numbered according to SEQ ID NO: 14) mutation (relative to a wild type constant domain), in bold text, to introduce a non-native covalent disulfide bond between the alpha and beta chains. Also in bold text is a C75A mutation (numbered according to SEQ ID NO: 14 which removes a native cysteine to decrease incorrect disulphide formation.

SEQ ID NO: 12:
DSGVTQTPKHLITATGQRVTLRCSPRSGDLSVYWYQQSLD
QGLQFLIQYYNGEERAKGNILERFSAQQFPDLHSELNLSS
LELGDSALYFCASSVWSSGGASAGELFFGEGSRLTVLEDL
KNVFPPEVAVFEPSEAEISHTQKATLVCLATGFYPDHVEL
SWWVNGKEVHSGVCTDPQPLKEQPALNDSRYALSSRLRVS

ATFWQDPRNHFRCQVQFYGLSENDEWTQDRAKPVTQIVSA

EAWGRAD

Figure 1:
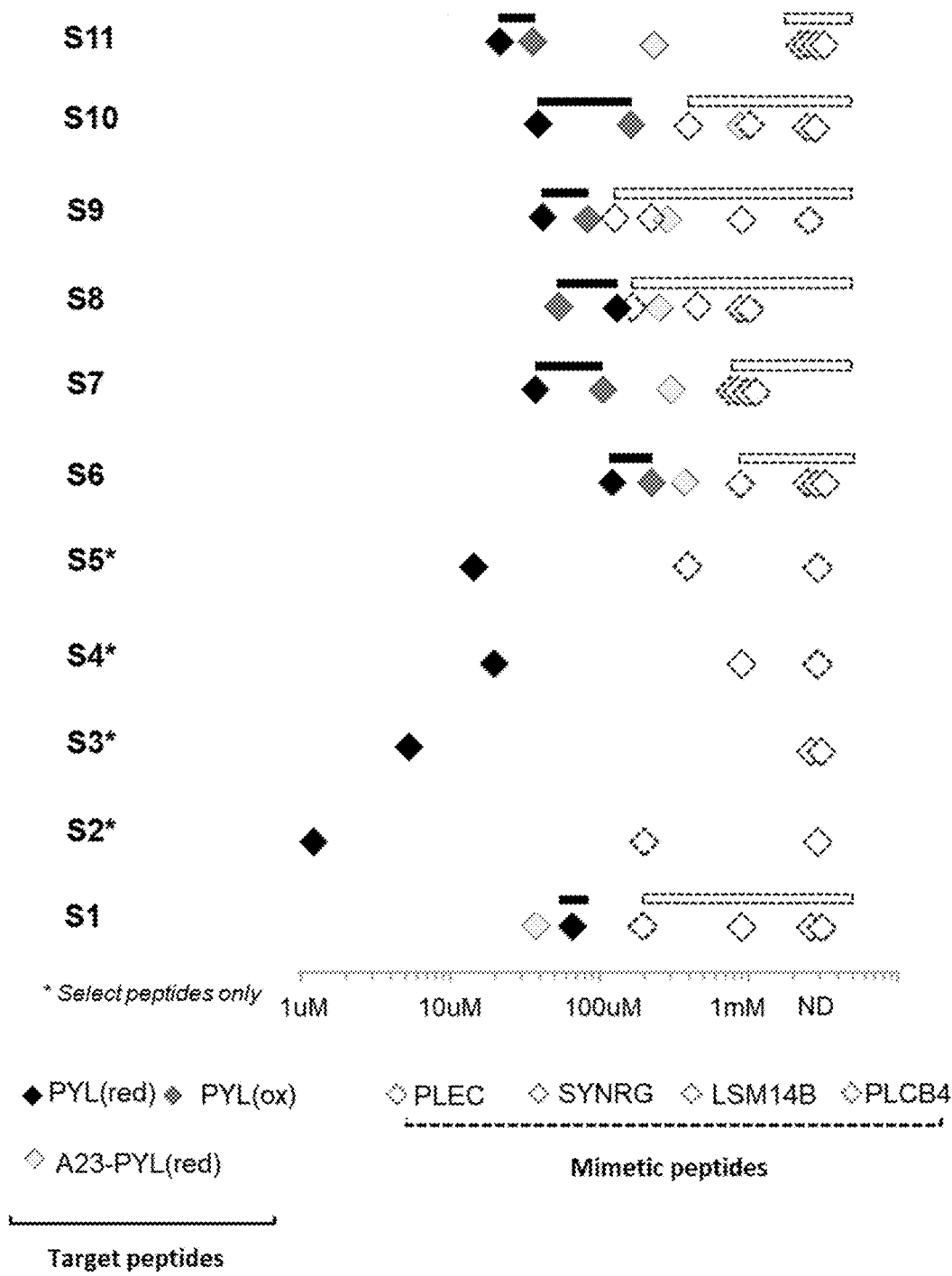
FIG. 1 is a chart showing the binding affinities of exemplary native TCRs to the target (PYLGQMINL, SEQ ID NO: 1) and mimetic peptide HLA complexes, as described in Example 1.

Exemplary Mutated TCR Alpha Chain Variable Domains

The following sequences are exemplary alpha chain variable domains which contain mutations relative to the wild type sequence in SEQ ID NO: 3. The CDRs are underlined and the mutations are shown in bold.

Alpha chain variable domain "a9" (SEQ ID NO: 22) comprising CDRs (CDR1, CDR2 and CDR3) designated SEQ ID NO: 5, 6 and 23, respectively, and framework regions (FR1, FR2, FR3 and FR4) designated SEQ ID NO: 8, 9, 10 and 11, respectively. This sequence includes the following mutations: S94G, N97H, D99N, which were found by the inventors to enhance affinity. SEQ ID NO: 22:

```
SEQ ID NO: 26:
AQSVTQLDSHVSVSEGTPVLLRCNYSSSYSPSLFWYVQHP

NKGLQLLLKYTSAATLVKGINGFEAEFKKSETSFHLTKPS

AHMSDAAEYFCVVGAPHRNDKIIFGKGTRLHILP
```

Alpha chain variable domain "a18" (SEQ ID NO: 24) comprising CDRs (CDR1, CDR2 and CDR3) designated SEQ ID NO: 5, 25 and 23, respectively, and framework regions (FR1, FR2, FR3 and FR4) designated SEQ ID NO: 8, 9, 10 and 11, respectively. This sequence includes the following mutations: T51I, S52G, A53N, A54D, S94G, N97H, D99N, which were found by the inventors to enhance affinity. SEQ ID NO: 24:

```
SEQ ID NO: 24:
AQSVTQLDSHVSVSEGTPVLLRCNYSSSYSPSLFWYVQHP

NKGLQLLLKYIGNDTLVKGINGFEAEFKKSETSFHLTKPS

AHMSDAAEYFCVVGAPHRNDKIIFGKGTRLHILP
```

Alpha chain variable domain "a77" (SEQ ID NO: 26) comprising CDRs (CDR1, CDR2 and CDR3) designated SEQ ID NO: 5, 27 and 23, respectively, and framework regions (FR1, FR2, FR3 and FR4) designated SEQ ID NO: 8, 9, 28 and 11, respectively. This sequence includes the following mutations: T51I, S52G, A53N, S94G, N97H, D99N, which were found by the inventors to enhance affinity; A54V and N61Q, which reduce deamidation risk. SEQ ID NO: 26:

```
SEQ ID NO: 26:
AQSVTQLDSHVSVSEGTPVLLRCNYSSSYSPSLFWYVQHP

NKGLQLLLKYIGNVTLVKGIQGFEAEFKKSETSFHLTKPS

AHMSDAAEYFCVVGAPHRNDKIIFGKGTRLHILP
```

Alpha chain variable domain "a90" (SEQ ID NO: 29) comprising CDRs (CDR1, CDR2 and CDR3) designated SEQ ID NO: 5, 27 and 30, respectively, and framework regions (FR1, FR2, FR3 and FR4) designated SEQ ID NO: 8, 9, 28 and 11, respectively. This sequence includes the following mutations: T51I, S52G, A53N, S94G, N97H, D99N, which were found by the inventors to enhance affinity; A54V and N61Q, which reduce deamidation risk; R98H, which was found to enhance affinity and stability. SEQ ID NO: 29:

```
SEQ ID NO: 29:
AQSVTQLDSHVSVSEGTPVLLRCNYSSSYSPSLFWYVQHP

NKGLQLLLKYIGNVTLVKGIQGFEAEFKKSETSFHLTKPS

AHMSDAAEYFCVVGAPHHNDKIIFGKGTRLHILP
```

Exemplary Mutated TCR Beta Chain Variable Domains

The following sequences are exemplary beta chain variable domains which contain mutations relative to the wild type sequence in SEQ ID NO: 13. The CDRs are underlined and the mutations are shown in bold.

Beta chain variable domain "b49" (SEQ ID NO: 31) comprising CDRs (CDR1, CDR2 and CDR3) designated SEQ ID NO: 32, 16 and 33, respectively, and framework regions (FR1, FR2, FR3 and FR4) designated SEQ ID NO: 18, 19, 20 and 21, respectively. This sequence includes the following mutations: L30Y, S98N, A103S, E105N, F107S, which were found by the inventors to enhance affinity. SEQ ID NO: 31:

```
SEQ ID NO: 31:
DSGVTQTPKHLITATGQRVTLRCSPRSGDYSVYWYQQSLDQGLQF

LIQYYNGEERAKGNILERFSAQQFPDLHSELNLSSLELGDSALYF

CASSVWSNGGASSGNLSFGEGSRLTVL
```

Beta chain variable domain "b150" (SEQ ID NO: 34) comprising CDRs (CDR1, CDR2 and CDR3) designated SEQ ID NO: 32, 35 and 36, respectively, and framework regions (FR1, FR2, FR3 and FR4) designated SEQ ID NO: 37, 38, 39 and 21, respectively. This sequence includes the following mutations: L30Y, A103S, E105N, F107S, which were found by the inventors to enhance affinity; G52 Å and S98I, which reduce deamidation risk; T13K, L43P, I47F, L61P, F90I, which were found to enhance stability. SEQ ID NO: 34:

```
SEQ ID NO: 34:
DSGVTQTPKHLIKATGQRVTLRCSPRSGDYSVYWYQQSLDQGPQF

LFQYYNAEERAKGNIPERFSAQQFPDLHSELNLSSLELGDSALYI

CASSVWSIGGASSGNLSFGEGSRLTVL
```

Beta chain variable domain "b152" (SEQ ID NO: 40) comprising CDRs (CDR1, CDR2 and CDR3) designated SEQ ID NO: 32, 35 and 41, respectively, and framework regions (FR1, FR2, FR3 and FR4) designated SEQ ID NO: 37, 38, 39 and 21, respectively. This sequence includes the following mutations: L30Y, A103S, E105N, F107S, which were found by the inventors to enhance affinity; G52A and S98I, which reduce deamidation risk; T13K, L43P, I47F, L61P, F90I, which were found to enhance stability, V95I, which was found to enhance affinity and stability. SEQ ID NO: 40:

```
SEQ ID NO: 40:
DSGVTQTPKHLIKATGQRVTLRCSPRSGDYSVYWYQQSLDQGPQF

LFQYYNAEERAKGNIPERFSAQQFPDLHSELNLSSLELGDSALYI

CASSIWSIGGASSGNLSFGEGSRLTVL
```

Exemplary TCRs

The following sequences are TCRs comprising exemplary combinations of the alpha and beta chain variable domains provided above. The TCRs are named "aXXbXX" (e.g., "a90b152"), where "aXX" denotes the alpha chain and "bXX" denotes the beta chain. Constant domains are shown in italics. The CDRs are underlined and the mutations relative to the scaffold TCR sequence (i.e., SEQ ID NO: 2 or 12) are shown in bold.

a9bwt TCR

TCR "a9bwt" alpha chain sequence (SEQ ID NO: 42), comprising the a9 variable domain (SEQ ID NO: 22) described above and the constant domain (SEQ ID NO: 4) from the scaffold TCR described above:

AQSVTQLDSHVSVSEGTPVLLRCNYSSSYSPSLFWYVQHPNKGLQ

LLLKYTSAATLVKGINGFEAEFKKSETSFHLTKPSAHMSDAAEYF

CVVGAPHRNDKIIFGKGTRLHILPNIQNPDPAVYQLRDSKSSDKS

VCLFTDFDSQTNVSQSKDSDVYITDKCVLDMRSMDFKSNSAVAWS

NKSDFACANAFNNSIIPEDT

TCR "a9bwt" beta chain sequence (SEQ ID NO: 12), comprising the wild type variable domain (SEQ ID NO: 13) and the constant domain (SEQ ID NO: 14) from the scaffold TCR described above:

DSGVTQTPKHLITATGQRVTLRCSPRSGDLSVYWYQQSLDQGLQF

LIQYYNGEERAKGNILERFSAQQFPDLHSELNLSSLELGDSALYF

CASSVWSSGGASAGELFFGEGSRLTVLEDLKNVFPPEVAVFEPSE

AEISHTQKATLVCLATGFYPDHVELSWWVNGKEVHSGVCTDPQPL

KEQPALNDSRYALSSRLRVSATFWQDPRNHFRCQVQFYGLSENDE

WTQDRAKPVTQIVSAEAWGRAD a18b49 TCR

TCR "a18b49" alpha chain sequence (SEQ ID NO: 44), comprising the a18 variable domain (SEQ ID NO: 24) described above and the constant domain (SEQ ID NO: 4) from the scaffold TCR described above:

AQSVTQLDSHVSVSEGTPVLLRCNYSSSYSPSLFWYVQHPNKGLQ

LLLKYIGNDTLVKGINGFEAEFKKSETSFHLTKPSAHMSDAAEYF

CVVGAPHRNDKIIFGKGTRLHILPNIQNPDPAVYQLRDSKSSDKS

VCLFTDFDSQTNVSQSKDSDVYITDKCVLDMRSMDFKSNSAVAWS

NKSDFACANAFNNSIIPEDT

TCR "a18b49" beta chain sequence (SEQ ID NO: 45), comprising the b49 variable domain (SEQ ID NO: 31) and the constant domain (SEQ ID NO: 14) from the scaffold TCR described above:

DSGVTQTPKHLITATGQRVTLRCSPRSGDYSVYWYQQSLDQGLQF

LIQYYNGEERAKGNILERFSAQQFPDLHSELNLSSLELGDSALYF

CASSVWSNGGASSGNLSFGEGSRLTVLEDLKNVFPPEVAVFEPSE

AEISHTQKATLVCLATGFYPDHVELSWWVNGKEVHSGVCTDPQPL

KEQPALNDSRYALSSRLRVSATFWQDPRNHFRCQVQFYGLSENDE

WTQDRAKPVTQIVSAEAWGRAD a77b150 TCR

TCR "a77b150" alpha chain sequence (SEQ ID NO: 46), comprising the a77 variable domain (SEQ ID NO: 26) described above and the constant domain (SEQ ID NO: 4) from the scaffold TCR described above:

AQSVTQLDSHVSVSEGTPVLLRCNYSSSYSPSLFWYVQHPNKGLQ

LLLKYIGNVTLVKGIQGFEAEFKKSETSFHLTKPSAHMSDAAEYF

CVVGAPHRNDKIIFGKGTRLHILPNIQNPDPAVYQLRDSKSSDKS

VCLFTDFDSQTNVSQSKDSDVYITDKCVLDMRSMDFKSNSAVAWS

NKSDFACANAFNNSIIPEDT

TCR "a77b150" beta chain sequence (SEQ ID NO: 47), comprising the b150 variable domain (SEQ ID NO: 34) and a constant domain (SEQ ID NO: 48) comprising a L3M mutation relative to the scaffold TCR:

DSGVTQTPKHLIKATGQRVTLRCSPRSGDYSVYWYQQSLDQGPQF

LFQYYNAEERAKGNIPERFSAQQFPDLHSELNLSSLELGDSALYI

CASSVWSIGGASSGNLSFGEGSRLTVLEDMKNVFPPEVAVFEPSE

AEISHTQKATLVCLATGFYPDHVELSWWVNGKEVHSGVCTDPQPL

KEQPALNDSRYALSSRLRVSATFWQDPRNHFRCQVQFYGLSENDE

WTQDRAKPVTQIVSAEAWGRAD a90b152 TCR

TCR "a90b152" alpha chain sequence (SEQ ID NO: 49), comprising the a90 variable domain (SEQ ID NO: 29) described above and the constant domain (SEQ ID NO: 4) from the scaffold TCR described above:

AQSVTQLDSHVSVSEGTPVLLRCNYSSSYSPSLFWYVQHPNKGLQ

LLLKYIGNVTLVKGIQGFEAEFKKSETSFHLTKPSAHMSDAAEYF

CVVGAPHHNDKIIFGKGTRLHILPNIQNPDPAVYQLRDSKSSDKS

VCLFTDFDSQTNVSQSKDSDVYITDKCVLDMRSMDFKSNSAVAWS

NKSDFACANAFNNSIIPEDT

TCR "a90b152" beta chain sequence (SEQ ID NO: 50), comprising the b152 variable domain (SEQ ID NO: 40) and a constant domain (SEQ ID NO: 48) comprising a L3M mutation relative to the scaffold TCR:

DSGVTQTPKHLIKATGQRVTLRCSPRSGDYSVYWYQQSLDQGPQF

LFQYYNAEERAKGNIPERFSAQQFPDLHSELNLSSLELGDSALYI

CASSIWSIGGASSGNLSFGEGSRLTVLEDMKNVFPPEVAVFEPSE

AEISHTQKATLVCLATGFYPDHVELSWWVNGKEVHSGVCTDPQPL

KEQPALNDSRYALSSRLRVSATFWQDPRNHFRCQVQFYGLSENDE

WTQDRAKPVTQIVSAEAWGRAD

Exemplary Anti-CD3 Antibody Sequences
anti-CD3 scFv: U0
SEQ ID NO: 51 is the amino acid sequence of an exemplary anti-CD3 scFv referred to herein as "U0". The light chain variable domain (VL) is in italics and is designated SEQ ID NO: 85. The light chain CDRs (CDR1, CDR2 and CDR3) are underlined and CDR1 and CDR3 are designated SEQ ID NO: 52 and 54 respectively. The heavy chain variable domain (VH) is shown in bold and is designated SEQ ID NO: 55. The heavy chain CDRs (CDR1, CDR2 and CDR3) are underlined and are designated SEQ ID NO: 56, 57 and 58. A glycine-serine linker, linking the VL and VH, is shown in plain text and is designated SEQ ID NO: 59.

SEQ ID NO: 51:

```
SEQ ID NO: 51:
AIQMTQSPSSLSASVGDRVTITCRASQDIRNYLNWYQQKPGKAPK

LLIYYTSRLESGVPSRFSGSGSGTDYTLTISSLQPEDFATYYCQQ

GNTLPWTFGQGTKVEIKGGGGSGGGGSGGGGSGGGGSGGGSEVQL

VESGGGLVQPGGSLRLSCAASGYSFTGYTMNWVRQAPGKGLEWVA

LINPYKGVSTYNQKFKDRFTISVDKSKNTAYLQMNSLRAEDTAVY

YCARSGYYGDSDWYFDVWGQGTLVTVSS
``` anti-CD3 scFv: U28

SEQ ID NO: 60 is the amino acid sequence of another exemplary anti-CD3 scFv referred to herein as "U28". This sequence is the same as SEQ ID NO: 51 above, except for two substitutions double-underlined (T164A and I201F). The light chain variable domain (VL) is in italics and is designated SEQ ID NO: 85. The light chain CDRs (CDR1, CDR2 and CDR3) are underlined and CDR1 and CDR3 are designated SEQ ID NO: 52 and 54 respectively. The heavy chain variable domain (VH) is shown in bold and is designated SEQ ID NO: 61. The heavy chain CDRs (CDR1, CDR2 and CDR3) are underlined (CDR1 includes the double underlined alanine residue) and are designated SEQ ID NO: 62, 57 and 58. A glycine-serine linker, linking the VL and VH, is shown in plain text and is designated SEQ ID NO: 59.

SEQ ID NO: 60:

```
SEQ ID NO: 60:
AIQMTQSPSSLSASVGDRVTITCRASQDIRNYLNWYQQKPGKAPK

LLIYYTSRLESGVPSRFSGSGSGTDYTLTISSLQPEDFATYYCQQ

GNTLPWTFGQGTKVEIKGGGGSGGGGSGGGGSGGGGSGGGSEVQL

VESGGGLVQPGGSLRLSCAASGYSFTGYAMNWVRQAPGKGLEWVA

LINPYKGVSTYNQKFKDRFTFSVDKSKNTAYLQMNSLRAEDTAVY

YCARSGYYGDSDWYFDVWGQGTLVTVSS
```

Exemplary TCR-Anti-CD3 Fusion Sequences a9bwt-U0

"a9bwt-U0" is a binding molecule comprising the TCR "a9bwt" alpha chain (SEQ ID NO: 42) described above and a TCR beta chain-anti-CD3 fusion (SEQ ID NO: 63). The beta chain-anti-CD3 fusion sequence (SEQ ID NO: 63) is shown below and comprises the U0 anti-CD3 scFv (SEQ ID NO: 51, italics, CDRs underlined) described above fused to the TCR "a9bwt" beta chain (SEQ ID NO: 43, bold, CDRs underlined) described above. The TCR beta chain and anti-CD3 scFv sequences are covalently linked via a glycine-serine linker (plain text), designated SEQ ID NO: 64.

```
SEQ ID NO: 63:
AIQMTQSPSSLSASVGDRVTITCRASQDIRNYLNWYQQKPGKAPK

LLIYYTSRLESGVPSRFSGSGSGTDYTLTISSLQPEDFATYYCQQ

GNTLPWTFGQGTKVEIKGGGGSGGGGSGGGGSGGGGSGGGSEVQL

VESGGGLVQPGGSLRLSCAASGYSFTGYTMNWVRQAPGKGLEWVA

LINPYKGVSTYNQKFKDRFTISVDKSKNTAYLQMNSLRAEDTAVY

YCARSGYYGDSDWYFDVWGQGTLVTVSSGGGGSDSGVTQTPKHLI

TATGQRVTLRCSPRSGDLSVYWYQQSLDQGLQFLIQYYNGEERAK

GNILERFSAQQFPDLHSELNLSSLELGDSALYFCASSVWSSGGAS

AGELFFGEGSRLTVLEDLKNVFPPEVAVFEPSEAEISHTQKATLV

CLATGFYPDHVELSWWVNGKEVHSGVCTDPQPLKEQPALNDSRYA

LSSRLRVSATFWQDPRNHFRCQVQFYGLSENDEWTQDRAKPVTQI

VSAEAWGRAD
``` a18b49-U0

"a18b49-U0" is a binding molecule comprising the TCR "a18b49" alpha chain (SEQ ID NO: 44) described above and a TCR beta chain-anti-CD3 fusion (SEQ ID NO: 65). The beta chain-anti-CD3 fusion sequence (SEQ ID NO: 65) is shown below and comprises the U0 anti-CD3 scFv (SEQ ID NO: 51, italics, CDRs underlined) described above fused to the TCR "a18b49" beta chain (SEQ ID NO: 45, bold, CDRs underlined) described above. The TCR beta chain and anti-CD3 scFv sequences are covalently linked via a glycine-serine linker (plain text), designated SEQ ID NO: 64.

```
SEQ ID NO: 65:
AIQMTQSPSSLSASVGDRVTITCRASQDIRNYLNWYQQKPGKAPK

LLIYYTSRLESGVPSRFSGSGSGTDYTLTISSLQPEDFATYYCQQ

GNTLPWTFGQGTKVEIKGGGGSGGGGSGGGGSGGGGSGGGSEVQL

VESGGGLVQPGGSLRLSCAASGYSFTGYTMNWVRQAPGKGLEWVA

LINPYKGVSTYNQKFKDRFTISVDKSKNTAYLQMNSLRAEDTAVY

YCARSGYYGDSDWYFDVWGQGTLVTVSSGGGGSDSGVTQTPKHLI

TATGQRVTLRCSPRSGDYSVYWYQQSLDQGLQFLIQYYNGEERAK

GNILERFSAQQFPDLHSELNLSSLELGDSALYFCASSVWSNGGAS

SGNLSFGEGSRLTVLEDLKNVFPPEVAVFEPSEAEISHTQKATLV

CLATGFYPDHVELSWWVNGKEVHSGVCTDPQPLKEQPALNDSRYA

LSSRLRVSATFWQDPRNHFRCQVQFYGLSENDEWTQDRAKPVTQI

VSAEAWGRAD
``` a77b150-U0

"a77b150-U0" is a binding molecule comprising the TCR "a77b150" alpha chain (SEQ ID NO: 46) described above and a TCR beta chain-anti-CD3 fusion (SEQ ID NO: 66). The beta chain-anti-CD3 fusion sequence (SEQ ID NO: 66) is shown below and comprises the U0 anti-CD3 scFv (SEQ ID NO: 51, italics, CDRs underlined) described above fused to the TCR "a77b150" beta chain (SEQ ID NO: 47, bold, CDRs underlined) described above. The TCR beta chain and anti-CD3 scFv sequences are covalently linked via a glycine-serine linker (plain text), designated SEQ ID NO: 64.

SEQ ID NO: 66:
*AIQMTQSPSSLSASVGDRVTITCRAS<u>QDIRNYL</u>NWYQQKPGKAPK*

*LLIY<u>YTS</u>RLESGVPSRFSGSGSGTDYTLTISSLQPEDFATYYC<u>QQ</u>*

*<u>GNTLPWT</u>FGQGTKVEIKGGGGSGGGGSGGGGSGGGGSGGGSEVQL*

*VESGGGLVQPGGSLRLSCAAS<u>GYSFTGYT</u>MNWVRQAPGKGLEWVA*

*<u>LINPYKGVST</u>YNQKFKDRFTISVDKSKNTAYLQMNSLRAEDTAVY*

*YC<u>ARSGYYGDSDWYFDV</u>WGQGTLVTVSSGGGGS*DSGVTQTPKHL

IKATGQRVTLRCS<u>PRSGDYS</u>VYWYQQSLDQGPQFLFQ<u>YYNAEERA</u>

KGNIPERFSAQQFPDLHSELNLSSLELGDSALYIC<u>ASSVWSIGGA</u>

<u>SSGNLS</u>FGEGSRLTVLEDMKNVFPPEVAVFEPSEAEISHTQKATL

VCLATGFYPDHVELSWWVNGKEVHSGVCTDPQPLKEQPALNDSRY

ALSSRLRVSATFWQDPRNHFRCQVQFYGLSENDEWTQDRAKPVTQ

IVSAEAWGRAD a77b150-U28

"a77b150-U28" is a binding molecule comprising the TCR "a77b150" alpha chain (SEQ ID NO: 46) described above and a TCR beta chain-anti-CD3 fusion (SEQ ID NO: 67). The beta chain-anti-CD3 fusion sequence (SEQ ID NO: 67) is shown below and comprises the U28 anti-CD3 scFv (SEQ ID NO: 60, italics, CDRs underlined) described above fused to the TCR "a77b150" beta chain (SEQ ID NO: 47, bold, CDRs underlined) described above. The TCR beta chain and anti-CD3 scFv sequences are covalently linked via a glycine-serine linker (plain text), designated SEQ ID NO: 64.

SEQ ID NO: 67:
*AIQMTQSPSSLSASVGDRVTITCRAS<u>QDIRNYL</u>NWYQQKPGKAPK*

*LLIY<u>YTS</u>RLESGVPSRFSGSGSGTDYTLTISSLQPEDFATYYC<u>QQ</u>*

*<u>GNTLPWT</u>FGQGTKVEIKGGGGSGGGGSGGGGSGGGGSGGGSEVQL*

*VESGGGLVQPGGSLRLSCAAS<u>GYSFTGYA</u>MNWVRQAPGKGLEWVA*

*<u>LINPYKGVST</u>YNQKFKDRFTFSVDKSKNTAYLQMNSLRAEDTAVY*

*YC<u>ARSGYYGDSDWYFDV</u>WGQGTLVTVSSGGGGS*DSGVTQTPKHL

IKATGQRVTLRCS<u>PRSGDYS</u>VYWYQQSLDQGPQFLFQ<u>YYNAEERA</u>

KGNIPERFSAQQFPDLHSELNLSSLELGDSALYIC<u>ASSVWSIGGA</u>

<u>SSGNLS</u>FGEGSRLTVLEDMKNVFPPEVAVFEPSEAEISHTQKATL

VCLATGFYPDHVELSWWVNGKEVHSGVCTDPQPLKEQPALNDSRY

ALSSRLRVSATFWQDPRNHFRCQVQFYGLSENDEWTQDRAKPVTQ

IVSAEAWGRAD a90b152-U0

"a90b152-U0" is a binding molecule comprising the TCR "a90b152" alpha chain (SEQ ID NO: 49) described above and a TCR beta chain-anti-CD3 fusion (SEQ ID NO: 68). The beta chain-anti-CD3 fusion sequence (SEQ ID NO: 68) is shown below and comprises the U0 anti-CD3 scFv (SEQ ID NO: 51, italics, CDRs underlined) described above fused to the TCR "a90b152" beta chain (SEQ ID NO: 50, bold, CDRs underlined) described above. The TCR beta chain and anti-CD3 scFv sequences are covalently linked via a glycine-serine linker (plain text), designated SEQ ID NO: 64.

SEQ ID NO: 68:
*AIQMTQSPSSLSASVGDRVTITCRAS<u>QDIRNYL</u>NWYQQKPGKAPK*

*LLIY<u>YTS</u>RLESGVPSRFSGSGSGTDYTLTISSLQPEDFATYYC<u>QQ</u>*

*<u>GNTLPWT</u>FGQGTKVEIKGGGGSGGGGSGGGGSGGGGSGGGSEVQL*

*VESGGGLVQPGGSLRLSCAAS<u>GYSFTGYT</u>MNWVRQAPGKGLEWVA*

*<u>LINPYKGVST</u>YNQKFKDRFTISVDKSKNTAYLQMNSLRAEDTAVY*

*YC<u>ARSGYYGDSDWYFDV</u>WGQGTLVTVSSGGGGS*DSGVTQTPKHL

IKATGQRVTLRCS<u>PRSGDYS</u>VYWYQQSLDQGPQFLFQ<u>YYNAEERA</u>

KGNIPERFSAQQFPDLHSELNLSSLELGDSALYIC<u>ASSIWSIGGA</u>

<u>SSGNLS</u>FGEGSRLTVLEDMKNVFPPEVAVFEPSEAEISHTQKATL

VCLATGFYPDHVELSWWVNGKEVHSGVCTDPQPLKEQPALNDSRY

ALSSRLRVSATFWQDPRNHFRCQVQFYGLSENDEWTQDRAKPVTQ

IVSAEAWGRAD a90b152-U28

"a90b152-U28" is a binding molecule comprising the TCR "a90b152" alpha chain (SEQ ID NO: 49) described above and a TCR beta chain-anti-CD3 fusion (SEQ ID NO: 69). The beta chain-anti-CD3 fusion sequence (SEQ ID NO: 69) is shown below and comprises the U28 anti-CD3 scFv (SEQ ID NO: 60, italics, CDRs underlined) described above fused to the TCR "a90b152" beta chain (SEQ ID NO: 50, bold, CDRs underlined) described above. The TCR beta chain and anti-CD3 scFv sequences are covalently linked via a glycine-serine linker (plain text), designated SEQ ID NO: 64.

SEQ ID NO: 69:
*AIQMTQSPSSLSASVGDRVTITCRAS<u>QDIRNYL</u>NWYQQKPGKAPK*

*LLIY<u>YTS</u>RLESGVPSRFSGSGSGTDYTLTISSLQPEDFATYYC<u>QQ</u>*

*<u>GNTLPWT</u>FGQGTKVEIKGGGGSGGGGSGGGGSGGGGSGGGSEVQL*

*VESGGGLVQPGGSLRLSCAAS<u>GYSFTGYA</u>MNWVRQAPGKGLEWVA*

*<u>LINPYKGVST</u>YNQKFKDRFTFSVDKSKNTAYLQMNSLRAEDTAVY*

*YC<u>ARSGYYGDSDWYFDV</u>WGQGTLVTVSSGGGGS*DSGVTQTPKHL

IKATGQRVTLRCS<u>PRSGDYS</u>VYWYQQSLDQGPQFLFQ<u>YYNAEERA</u>

KGNIPERFSAQQFPDLHSELNLSSLELGDSALYIC<u>ASSIWSIGGA</u>

<u>SSGNLS</u>FGEGSRLTVLEDMKNVFPPEVAVFEPSEAEISHTQKATL

VCLATGFYPDHVELSWWVNGKEVHSGVCTDPQPLKEQPALNDSRY

ALSSRLRVSATFWQDPRNHFRCQVQFYGLSENDEWTQDRAKPVTQ

IVSAEAWGRAD

Exemplary Amino Acid Linker Sequences

| | |
|---|---|
| GGGGS, | (SEQ ID NO: 64) |
| GGGSG, | (SEQ ID NO: 70) |
| GGSGG, | (SEQ ID NO: 71) |

-continued

GSGGG, (SEQ ID NO: 72)

GSGGGP, (SEQ ID NO: 73)

GGEPS, (SEQ ID NO: 74)

GGEGGGP, (SEQ ID NO: 75)

GGEGGGSEGGGS, (SEQ ID NO: 76)

GGGSGGGG, (SEQ ID NO: 77)

GGGGSGGGGSGGGGSGGGGSGGGS, (SEQ ID NO: 59)

-continued

GGGGSGGGGGGGGSGGGGS, (SEQ ID NO: 78)

EAAAK (SEQ ID NO: 79)

and

EAAAKEAAAKEAAAK. (SEQ ID NO: 80)

Figure 7:
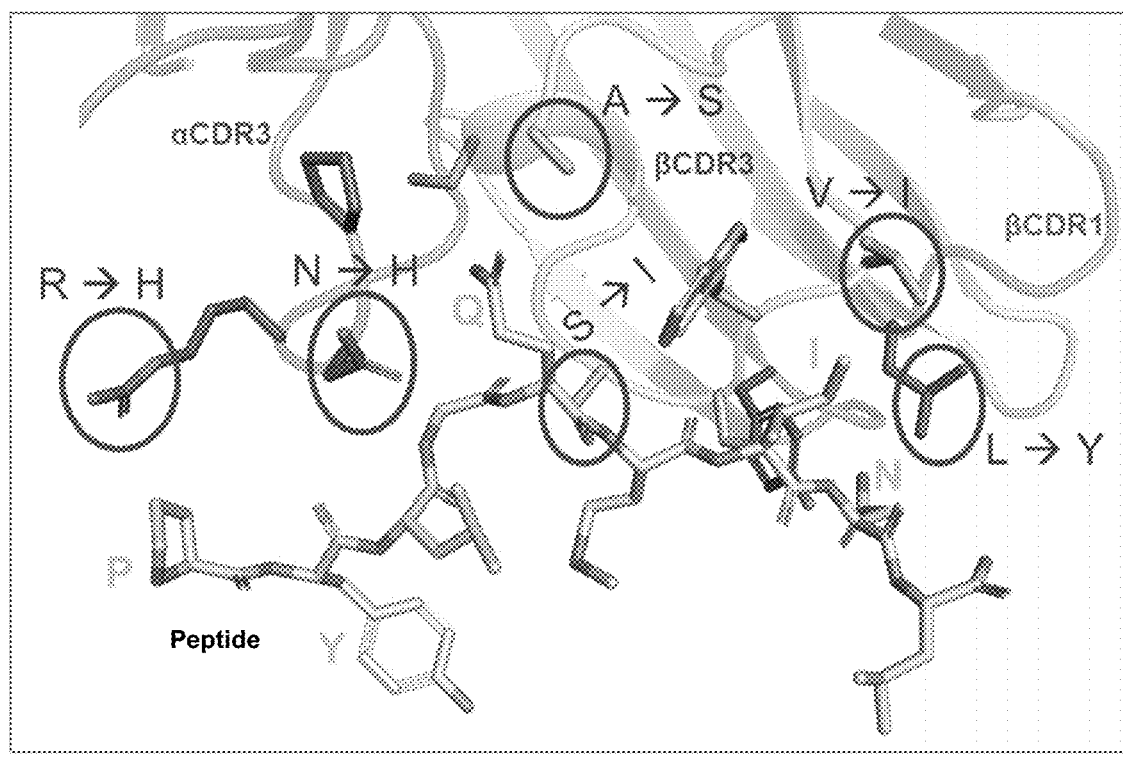

TCR CDR Amino Acid Residues Critical for Binding to the PYLGQMINL (SEQ ID NO: 1) HLA-A24 Complex The structures of the TCRs "S11" and variant "a90b152" bound to the PYLGQMINL (SEQ ID NO: 1) HLA-A24 complex (described in Example 7 and shown in FIGS. 7 and 8) were used to determine amino acid sequences of CDRs that confer specific binding of the TCR to the pHLA complex based on the key CDR residues contacting the peptide in the complex. In the following tables, "X" represents any amino acid. The forward slash ("/") represents "or", e.g., "S/T" indicates that the amino acid can be S (Ser) or T (Thr) at the specified position in the sequence.

TCR Alpha Chain CDR 1 Sequences:

| SEQ ID NO | Sequence | | | | | |
|---|---|---|---|---|---|---|
| | 1 | 2 | 3 | 4 | 5 | 6 |
| 129 | S/T | S/T | Y/W/F | S/T | P/G | S/T |
| 130 | S/T | S/T | Y/W/F | S/T | P | S/T |

TCR Alpha Chain CDR 2 Sequences:

| SEQ ID NO | Sequence | | | | | | | |
|---|---|---|---|---|---|---|---|---|
| | 1 | 2 | 3 | 4 | 5 | 6 | 7 | 8 |
| 131 | Y/W/F | T/I | S/G | A/N | A/D/V | T/S | L/I/V | V/I/L |
| 132 | Y/W/F | I | G | N | V | T/S | L/I/V | V/I/L |

TCR Alpha Chain CDR 3 Sequences:

| SEQ ID NO | Sequence | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| 125 | X | X | X | X | P | N/H | R/H | X | X | X | X | X |
| 133 | X | X | S/G | X | P | N/H | R/H | D/N | X | X | X | X |
| 134 | V/I/L | V/I/L | S/G | A/G | P | N/H | R/H | D/N | D/E | K/R/H | I/V/L | I/V/L |
| 135 | V/I/L | V/I/L | G | A/G | P | H | H | N | D/E | K/R/H | I/V/L | I/V/L |

TCR Beta Chain CDR 1 Sequences:

| SEQ ID NO | Sequence | | | | |
|---|---|---|---|---|---|
| | 1 | 2 | 3 | 4 | 5 |
| 126 | X | X | X | L/Y | X |
| 136 | S/T | G/A | D/E | L/Y | S/T |
| 137 | S/T | G/A | D/E | Y | S/T |

TCR Beta Chain CDR 2 Sequences:

| SEQ ID NO | Sequence | | | | | |
|---|---|---|---|---|---|---|
| | 1 | 2 | 3 | 4 | 5 | 6 |
| 127 | X | Y | X | X | X | X |
| 138 | Y/W/F | Y | N/Q | G/A | E/D | E/D |

TCR Beta Chain CDR 3 Sequences:

| SEQ ID | Sequence | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| 128 | X | X | X | V/I | W | S | S/I/N | G | X | X | S | A/S | X | X | X | X |
| 139 | X | X | X | V/I | W | S | S/I/N | G | X | X | S | A/S | X | E/N | X | F/S |
| 140 | A/G | S/T | S/T | V/I | W | S | S/I/N | G | G/A | A/G | S | A/S | G/A | E/N | L/I/V | F/S |
| 141 | A/G | S/T | S/T | I | W | S | I | G | G/A | A/G | S | S | G/A | N | L/I/V | S |

Other Amino Acid Sequences Referred to Herein
Other Native TCR Sequences

SEQ ID NOs: 86 to 105 are the alpha chain and beta chain CDR3 sequences of the native TCRs, S1 to S10, described in Example 1. S11 is the exemplary native TCR described above. The CDR3 sequences for SEQ ID NOs: 86 to 105 are provided in the table in Example 1 below.

Other Mutated TCR Sequences, Containing Mutations Relative to the Exemplary Native TCR "S11"

CDRs are underlined and mutations relative to the exemplary native TCR "S11" (alpha chain of SEQ ID NO: 2 and beta chain of SEQ ID NO: 12) are shown in bold text.

```
a19 alpha chain variable domain (SEQ ID NO: 109):
AQSVTQLDSHVSVSEGTPVLLRCNYSSSYSPSLFWYVQHPNKGLQLLLKWFWGDTLVKGINGFEAE

FKKSETSFHLTKPSAHMSDAAEYFCVVGAPHRNDKIIFGKGTRLHILP a20 alpha chain variable domain (SEQ ID NO: 110):
AQSVTQLDSHVSVSEGTPVLLRCNYSSSYSPSLFWYVQHPNKGLQLLLKYNGLKTLVKGINGFEAEF

KKSETSFHLTKPSAHMSDAAEYFCVVGAPHRNDKIIFGKGTRLHILP a23 alpha chain variable domain (SEQ ID NO: 111):
AQSVTQLDSHVSVSEGTPVLLRCNYSSSYSPSLFWYVQHPNKGLQLLLKYTWGATLVKGINGFEAEF

KKSETSFHLTKPSAHMSDAAEYFCVVGAPHRNDKIIFGKGTRLHILP a25 alpha chain variable domain (SEQ ID NO: 118):
AQSVTQLDSHVSVSEGTPVLLRCNYSSSYSPSLFWYVQHPNKGLQLLLKYIGLGTLVKGINGFEAEFK

KSETSFHLTKPSAHMSDAAEYFCVVGAPHRNDKIIFGKGTRLHILP a26 alpha chain variable domain (SEQ ID NO: 119):
AQSVTQLDSHVSVSEGTPVLLRCNYSSSYSPSLFWYVQHPNKGLQLLLKYIGLNTLVKGINGFEAEFK

KSETSFHLTKPSAHMSDAAEYFCVVGAPHRNDKIIFGKGTRLHILP b10 beta chain variable domain (SEQ ID NO: 106):
DSGVTQTPKHLITATGQRVTLRCSPRPGHLSVYWYQQSLDQGLQFLTQYYNGQELAKGNILERFSA

QQFPDLHSELNLSSLELGDSALYFCASSVWSYGGASAGALFFGEGSRLTVL b12 beta chain variable domain (SEQ ID NO: 107):
DSGVTQTPKHLITATGQRVTLRCSPRSGDLSVYWYQQSLDQGLQFLIQYYNGEERAKGNILERFSAQ

QFPDLHSELNLSSLELGDSALYFCASSVWSYGGASAGALFFGEGSRLTVL b13 beta chain variable domain (SEQ ID NO: 108):
DSGVTQTPKHLITATGQRVTLRCSPRSGDLSVYWYQQSLDQGLQFLTQYYNGQELAKGNILERFSA

QQFPDLHSELNLSSLELGDSALYFCASSVWSSGGASAGELFFGEGSRLTVL b16 beta chain variable domain (SEQ ID NO: 112):
DSGVTQTPKHLITATGQRVTLRCSPRSGDLSVYWYQQSLDQGLQFLIQYYNGWEAQKGNILERFSA

QQFPDLHSELNLSSLELGDSALYFCASSVWSSGGASAGELFFGEGSRLTVL b17 beta chain variable domain (SEQ ID NO: 113):
DSGVTQTPKHLITATGQRVTLRCSPRSGDLSVYWYQQSLDQGLQFLIQYYNGEERAKGNILERFSAQ

QFPDLHSELNLSSLELGDSALYFCASSHWAVGGASAGELFFGEGSRLTVL b19 beta chain variable domain (SEQ ID NO: 114):
DSGVTQTPKHLITATGQRVTLRCSPRSGDLSVYWYQQSLDQGLQFLIQYYNGEERAKGNILERFSAQ

QFPDLHSELNLSSLELGDSALYFCASSVWSNGGASSGNLSFGEGSRLTVL b20 beta chain variable domain (SEQ ID NO: 115):
DSGVTQTPKHLITATGQRVTLRCSPRSGDLSVYWYQQSLDQGLQFLIKYYNGEEQAKGNILERFSAQ

QFPDLHSELNLSSLELGDSALYFCASSLWSSGGASAGELSFGEGSRLTVL b29 beta chain variable domain (SEQ ID NO: 116):
DSGVTQTPKHLITATGQRVTLRCSPRSGDLSVYWYQQSLDQGLQFLIQYYNGAELAKGNILERFSAQ

QFPDLHSELNLSSLELGDSALYFCASSVWSFGGASAGELLFGEGSRLTVL b32 beta chain variable domain (SEQ ID NO: 117):
DSGVTQTPKHLITATGQRVTLRCSPRSGDLSVYWYQQSLDQGLQFLIKYYNGEESAKGNILERFSAQ

QFPDLHSELNLSSLELGDSALYFCASSMWSFGGASAGELLFGEGSRLTVL b39 beta chain variable domain (SEQ ID NO: 120):
DSGVTQTPKHLITATGQRVTLRCSPRSGDLSVYWYQQSLDQGLQFLIQYYNGGELAKGNILERFSAQ

QFPDLHSELNLSSLELGDSALYFCASSVWSYGGASAGELFFGEGSRLTVL
```

-continued b42 beta chain variable domain (SEQ ID NO: 121):
DSGVTQTPKHLITATGQRVTLRCSPR<u>SGDLSV</u>YWYQQSLDQGLQFLNQYYNGVELAKGNILERFSA QQFPDLHSELNLSSLELGDSALYFC<u>ASSVWSFGGASAGELF</u>FGEGSRLTVL b50 beta chain variable domain (SEQ ID NO: 123):
DSGVTQTPKHLITATGQRVTLRCSPR<u>SGDLSV</u>YWYQQSLDQGLQFLIQYYNGEELAKGNILERFSAQ QFPDLHSELNLSSLELGDSALYFC<u>ASSVWSFGGASSGNLSF</u>GEGSRLTVL b51 beta chain variable domain (SEQ ID NO: 124):
DSGVTQTPKHLITATGQRVTLRCSPR<u>SGDLSV</u>YWYQQSLDQGLQFLIKYYNGEEQAKGNILERFSAQ QFPDLHSELNLSSLELGDSALYFC<u>ASSVWSNGGASSGNLSF</u>GEGSRLTVL

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the purview of this application and scope of the appended claims.

Example 1—Identification of a Native TCR with Suitable Therapeutic Properties TCRs that bind to the PYLGQMINL-HLA-A*24 complex were isolated from T cell clones obtained from human donors, or from TCR phage libraries, and the amino acid sequences of alpha and beta variable regions determined. The construction of native TCR phage libraries has been described previously (e.g., in WO 2015/136072, WO 2017/046198 and WO 2017/046201). Soluble versions of the TCRs were produced by fusing variable regions to truncated versions of the respective alpha and beta chain constant domains, a non-native interchain disulphide bond was incorporated between constant domain residues as previously described (WO 2003/020763).

Alpha and beta chains were expressed separately in E. coli inclusion bodies. Solubilised inclusion bodies containing alpha and beta chain were combined. Refolded TCRs were then purified by anion exchange and size exclusion chromatography using established methods Boulter, et al. (2003), Protein Eng. 16, 707-711; Liddy, et al. (2012), Nature medicine vol. 18,6: 980-7)

To assess the ability of the native TCRs to recognise the target pHLA complex, binding parameters were obtained by Surface Plasmon Resonance (SPR). Binding to both oxidised and reduced versions of the target peptide were tested independently (position M6 of the target peptide PYLGQMINL can exist in both oxidised and reduce form). SPR measurements were carried out on a BIAcore 8K, BIAcore 3000 or BIAcore T200 instrument. Briefly, biotinylated class I HLA-A*24 molecules were refolded with the peptide of interest and purified using available methods (O'Callaghan et al. (1999), Anal Biochem 266(1): 9-15; Garboczi, et al. (1992), Proc Natl Acad Sci USA 89(8): 3429-3433). Biotinylated peptide-HLA monomers were immobilized on to streptavidin-coupled CM-5 sensor chips. Equilibrium binding constants were determined using serial dilutions of soluble TCR. $K_D$ values were obtained by non-linear curve fitting using Prism software and the Langmuir binding isotherm, bound=C*Max/(C+KD), where "bound" is the equilibrium binding in response units at injected TCR concentration C and Max is the maximum binding. Measurements were performed at 25° C., unless otherwise indicated, in Dulbecco's PBS buffer, supplemented with 0.005% P20.

Eleven native TCRs were identified that bound to the target pHLA complex with affinities in the low μM range. Chain usage and CDR3 sequences of each TCR was determined. The results are summarised in the table below.

| TCR | Source | Chain pairing (TRAV/TRBV) | aCDR3 | bCDR3 | Binding affinity $K_D$ (μM) Red/Ox |
|---|---|---|---|---|---|
| S1 | T cell clone | 24/25 | AFISWRSSGDKLT (SEQ ID NO: 86) | ASSSPLSGPLASPLH (SEQ ID NO: 87) | 85/nt |
| S2 | Phage library | 12/7-9 | AVRGGGADGLT (SEQ ID NO: 88) | ASSLVGTEAF (SEQ ID NO: 89) | 1.2/nt |
| S3 | Phage library | 12/6-5 | AAHPGGTSYGKLT (SEQ ID NO: 90) | ASTPWLGIQGYT (SEQ ID NO: 91) | 7.8/nt |
| S4 | Phage library | 12-2/6-2/3 | AVNGPNNAGNMLT (SEQ ID NO: 92) | ASSPGGFGQPQH (SEQ ID NO: 93) | 18.9/nt |
| S5 | Phage library | 12-2/6-1 | AVNKGFQKLV (SEQ ID NO: 94) | ASSEGWGGQPQH (SEQ ID NO: 95) | 14.5/nt |
| S6 | Phage library | 21/7-9 | AVPNPSARQLT (SEQ ID NO: 96) | ASSLEGQGVEQF (SEQ ID NO: 97) | 126/241 |

-continued

| TCR Source | Chain pairing (TRAV/TRBV) | aCDR3 | bCDR3 | Binding affinity $K_D$ (μM) Red/Ox |
|---|---|---|---|---|
| S7 Phage library | 21/7-9 | APAAAAGNKLT (SEQ ID NO: 98) | ASSLGHKSYEQY (SEQ ID NO: 99) | 42/117 |
| S8 Phage library | 21/7-9 | AVDSSNTGKLI (SEQ ID NO: 100) | ASSSYHAYGYT (SEQ ID NO: 101) | 141/44 |
| S9 T cell clone | 21/5-6 | AVGRDYGQNFV (SEQ ID NO: 102) | ASSYQGFNQPQH (SEQ ID NO: 103) | 55/100 |
| S10 T cell clone | 27/5-6 | GAIWSTLGRLY (SEQ ID NO: 104) | SSFKGVNQPQH (SEQ ID NO: 105) | 53/193 |
| S11 T cell clone | 8-2/9-1 | VVSAPNRDDKII (SEQ ID NO: 7) | ASSVWSSGGASAGELF (SEQ ID NO: 17) | 27/36 | nt = not tested

To determine the specificity of each native TCR to the target pHLA complex binding to mimetic peptides was assessed. Potential mimetic peptides were first identified by searching the human proteome for sequences that differ by up to 3 amino acids from the target peptide. In each case binding of the mimetic peptides to HLA-A*24 was confirmed. Four mimetic peptides were identified and are shown in the table below. Positions that differ from the target peptide are underlined. The interaction between each native TCR and mimetic peptides was carried out using SPR methods as described above.

| Mimetic ID | Peptide (SEQ ID) | Protein |
|---|---|---|
| Mim1 | PYTGQQISL (SEQ ID NO: 81) | PLEC |
| Mim2 | PYLGQAPFL (SEQ ID NO: 82) | SYNRG |
| Mim3 | PYLSTMINY (SEQ ID NO: 83) | PLCB4 |
| Mim4 | PYLGSKISL (SEQ ID NO: 84) | LSM14B |

Ten of the eleven native TCRs demonstrated detectable recognition of one or more mimetic pHLA complex (FIG. 1). TCR S11 did not bind of any of the four mimetics.

Figure 2:
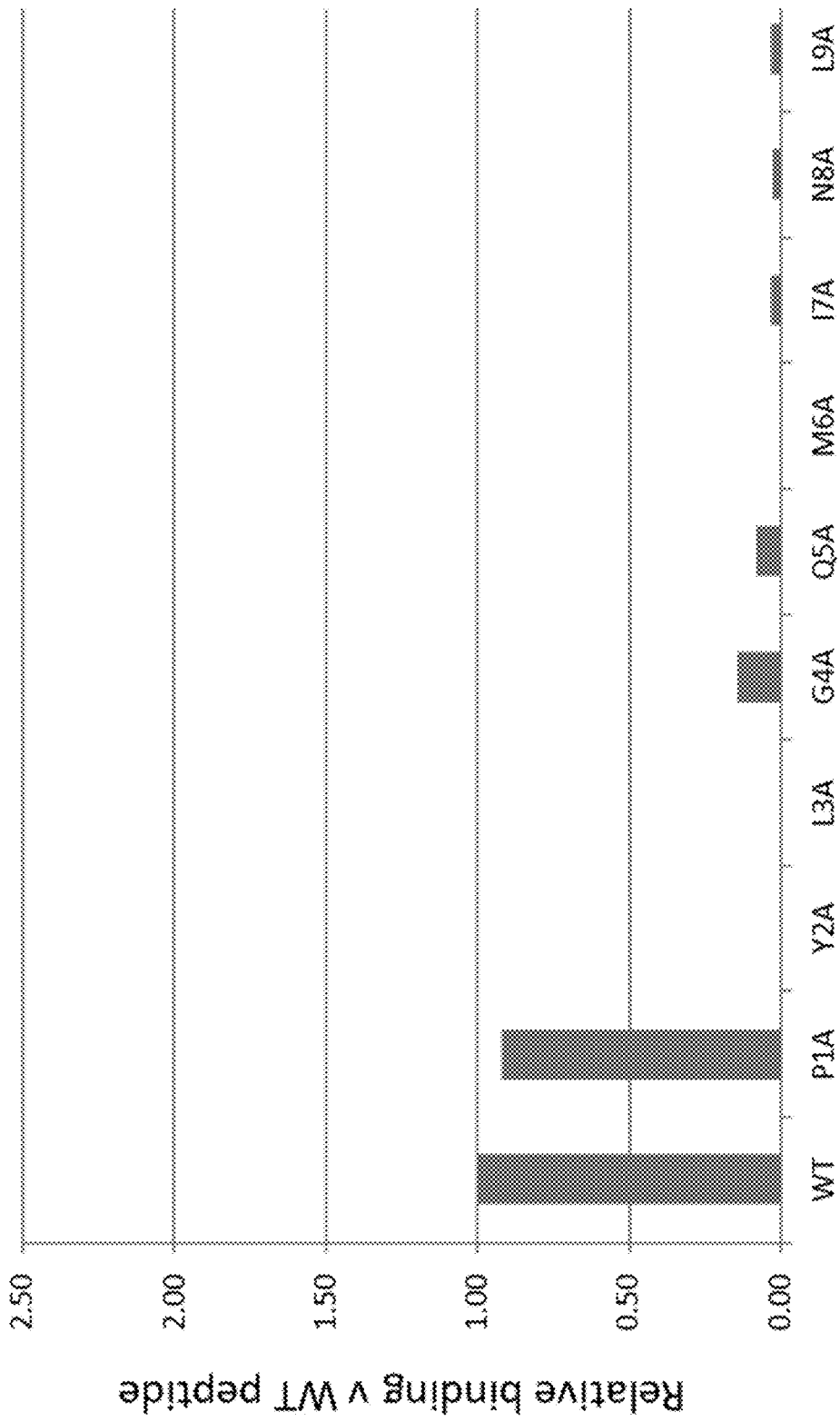
FIG. 2 is a bar graph showing the results of an alanine scanning experiment for the native S11 TCR. Relative binding vs the wildtype target peptide (PYLGQMINL, SEQ ID NO: 1) is shown for each mutant peptide having an alanine mutation at the specified position, as described in Example 1.

The recognition profile of native TCR S11 was further characterised using single alanine substitutions of the target peptide and testing for binding using SPR. The data show that substitutions with alanine at 8 of 9 peptide positions abolishes TCR binding, indicating that the S11 TCR has a high level of specificity for the target pHLA (FIG. 2).

S11 TCR was additionally assessed for binding to a panel of 18 irrelevant peptide HLA-A*24 complexes that are naturally presented. For the SPR measurements, the irrelevant pHLAs were divided into three groups and loaded onto one of three flow cells. Soluble TCR was injected at concentrations of 85.8, 42.9 and 21.4 μM over all flow cells. No significant binding was detected at either concentration indicting that the soluble WT TCR has a high degree to specificity for the peptide-HLA-A*24 complex.

Example 2—Identification of TCR Variants with Improved Binding

TCR S11 was used as a template to identify mutations with higher affinity as previously described (Li et al. (2005), Nat. Biotechnol. 23, 349-354). Briefly, TCR phage libraries were generated using NNK oligonucleotides to generate mutations in the complementarity-determining regions (CDRs). Additional improvements in TCR affinities were achieved in second-generation libraries using TCRs isolated from the first round. Combinations of mutated alpha and beta chains were subsequently selected.

To assess binding, soluble TCRs comprising mutated alpha and beta chains were first prepared as bispecific molecules, by fusing an antiCD3 scFv fragment to the N terminus of the TCR beta chain. Binding molecules in this format are ImmTAC® molecules including, for example, tebentafusp, sold under the brand name KIMMTRAK®. Such molecules are referred to as "TCR-anti-CD3 fusion" below.

TCR-anti-CD3 fusion molecules comprising mutated alpha and beta chains were expressed in E. coli and purified as previously described. The yield was calculated from the concentration of purified material as determined by absorbance at 280 nm using a Nanodrop spectrophotometer.

Binding to target was assessed by SPR using a similar method as described above. For high affinity interactions binding parameters were determined by single cycle kinetics analysis. Five different concentrations of TCR-anti-CD3 fusion were injected over a flow cell coated with ~100-200 RU (or 50-100 RU for Biacore 8K instrument) of peptide-HLA complex using a flow rate of 50-60 μl min-1. Typically, 60-120 μl (or approx. 240 μl for Biacore 8K instrument) of TCR-anti-CD3 fusion was injected at a top concentration of between 50-100 nM (or 2-50 nM for Biacore 8K instrument), with successive 2 fold dilutions used for the other four injections. The lowest concentration was injected first. To measure the dissociation phase, buffer was injected until≥10% dissociation occurred, typically after 1-3 hours. Kinetic parameters were calculated using BIAevaluation® software. The dissociation phase was fitted to a single exponential decay equation enabling calculation of half-life. The equilibrium constant KD was calculated from koff/kon.

In a first round of mutagenesis TCR variants were identified with binding affinities for the target pHLA (reduced form) greater (i.e. stronger) than WT and in the range 25 nM-171 nM, as shown in the table below.

| Molecule ID | TRAV SEQ ID NO | TRBV SEQ ID NO | PYL (red) $K_D$ (μM) | PYL (red) $T\frac{1}{2}$ (sec) | PYL (ox) $K_D$ (μM) | PYL (ox) $T\frac{1}{2}$ (sec) | Yield (mg/L) |
|---|---|---|---|---|---|---|---|
| awtbwt | 3 | 13 | 27.1 | 36.1 | nt | nt | 13.8 |
| a9bwt | 22 | 13 | 0.166 | 34 | 0.266 | 21 | 2.3 |
| awtb10 | 3 | 106 | 0.025 | 356 | 0.048 | 126 | 0.3 |
| a9b12 | 22 | 107 | 0.014 | 286 | 0.055 | 96 | 0.02 |
| a9b13 | 22 | 108 | 0.171 | 142 | 0.255 | 109 | 0.36 | nt = not tested

Variant a9bwt was selected as a template for further engineering.

In a further round of mutagenesis TCR variants were identified with binding affinities for the target pHLA (reduced form) in the range 3 nM-37 nM, as shown in the table below.

| Molecule ID | TRAV SEQ ID NO | TRBV SEQ ID NO | PYL (red) $K_D$ (nM) | PYL (red) $T\frac{1}{2}$ (sec) | PYL (ox) $K_D$ (nM) | PYL (ox) $T\frac{1}{2}$ (sec) | Yield (mg/L) |
|---|---|---|---|---|---|---|---|
| a18bwt | 24 | 13 | 7.86 | 1090 | 12.4 | 605 | 4.15 |
| a19bwt | 109 | 13 | 3.00 | 2360 | 5.13 | 1320 | 2.18 |
| a20bwt | 110 | 13 | 23.6 | 470 | 28.8 | 257 | 3.86 |
| a23bwt | 111 | 13 | 19.8 | 213 | 28.1 | 121 | 4.04 |
| a9b16 | 22 | 112 | 37.3 | 923 | 26.6 | 336 | 0.48 |
| a9b17 | 22 | 113 | 22.0 | 438 | 15.4 | 189 | 2.62 |
| a9b19 | 22 | 114 | 7.25 | 513 | 9.23 | 283 | 0.67 |
| a9b20 | 22 | 115 | 3.79 | 1850 | 7.48 | 915 | 2.33 |

Further combinations of mutated TCRs chains gave rise to TCR variants with binding affinities for the target pHLA (reduced form) in the range 101 pM-1.3 nM, as shown in the table below.

| Molecule ID | TRAV SEQ ID NO | TRBV SEQ ID NO | PYL (red) $K_D$ (pM) | PYL (red) $T\frac{1}{2}$ (min) | PYL (ox) $K_D$ (pM) | PYL (ox) $T\frac{1}{2}$ (min) | Yield (mg/L) |
|---|---|---|---|---|---|---|---|
| a18b17 | 24 | 113 | 1300 | 61.5 | 1200 | 30 | 3.65 |
| a18b20 | 24 | 115 | 101 | 438 | 265 | 243 | 5.11 |
| a20b17 | 110 | 113 | 1360 | 50 | 265 | 20.8 | 3.21 |
| a20b19 | 110 | 114 | 213 | 102 | 758 | 57.6 | 1.14 |
| a20b20 | 110 | 115 | 192 | 321 | 553 | 173 | 3.88 |
| a23b17 | 111 | 113 | 667 | 43 | 486 | 19.8 | 3.32 |
| a23b19 | 111 | 114 | 142 | 71 | 753 | 40.8 | 1.92 |
| a23b20 | 111 | 115 | 122 | 221 | 364 | 112.8 | 4.78 |

TCR alpha and beta chains a18 and b19 were selected for combination with additional mutant chains. The table below shows TCR variants with binding affinities for the target pHLA (reduced form) in the range 17.7 PM-817 pM, as shown in the table below.

| Molecule ID | TRAV SEQ ID NO | TRBV SEQ ID NO | PYL (red) $K_D$ (pM) | PYL (red) $T\frac{1}{2}$ (h) | PYL (ox) $K_D$ (pM) | PYL (ox) $T\frac{1}{2}$ (h) | Yield (mg/L) |
|---|---|---|---|---|---|---|---|
| a18b19 | 24 | 114 | 100 | 4.0 | 277 | 2.3 | 2.38 |
| a18b29 | 24 | 116 | 204 | 18.1 | 577 | 1.93 | 0.98 |
| a18b32 | 24 | 117 | 205 | 5 | 471 | 3.13 | 2.1 |
| a25b19 | 118 | 114 | 92 | 6.44 | 177 | 3.52 | 2.17 |
| a26b19 | 119 | 114 | 44.2 | 12.58 | 90.1 | 7.47 | 2.36 |
| a18b39 | 24 | 120 | 817 | 6.3 | 2170 | 3 | 0.47 |

-continued

| Molecule ID | TRAV SEQ ID NO | TRBV SEQ ID NO | PYL (red) $K_D$ (pM) | PYL (red) T½ (h) | PYL (ox) $K_D$ (pM) | PYL (ox) T½ (h) | Yield (mg/L) |
|---|---|---|---|---|---|---|---|
| a18b42 | 24 | 121 | 725 | 10.02 | 1110 | 0.85 | 2.39 |
| a18b49 | 24 | 31 | 84.5 | 8.86 | 166 | 5.36 | 1.56 |
| a18b50 | 24 | 123 | 134 | 12.19 | 594 | 2.11 | 1.14 |
| a18b51 | 24 | 124 | 17.7 | >20 | 28.4 | >20 | 4.47 |

These data demonstrate that soluble high affinity TCR variants of S11 TCR can be produced that have supraphysiological affinity and binding half-life for target.

Example 3—TCR-Anti-CD3 Fusion Molecules Demonstrate Potent T Cell Activation in the Presence of Antigen Positive Target Cells T cell activation was determined by measuring IFNγ secretion using an ELISpot assay. Assays were performed using a human IFN-γ ELISPOT kit (BD Biosciences) according to the manufacturer's instructions. Peripheral blood mononuclear cells (PBMC), isolated from fresh donor blood, were used as effector cells.

In this example the following cancer cells lines were used as antigen positive target cells: CHP-212 (neuroblastoma); HT144 (melanoma); RMGI (ovarian carcinoma). In addition, the following antigen negative cell lines were used: SW620 (colon adenoncarcinoma); NUDUL1 (undifferentiated lymphoma). Data were plotted using PRISM software and $EC_{50}$ values were calculated from the curves.

In each case concentration dependent T cell reactivity was observed in the presence of antigen positive cells, as shown in the table below.

| Molecule ID | TRAV SEQ ID | TRBV SEQ ID | Antigen positive cell line CHP-212 (pM) | Antigen positive cell line HT144 (pM) | Antigen positive cell line RMGI (pM) |
|---|---|---|---|---|---|
| a18b17 | 24 | 113 | 1000 | 567 | 286 |
| a18b20 | 24 | 115 | 524 | 148 | 32.8 |
| a20b17 | 110 | 113 | 606 | 403 | 366 |
| a20b19 | 110 | 114 | 435 | 276 | 51.4 |
| a20b20 | 110 | 115 | 196 | 203 | 40.9 |
| a23b17 | 111 | 113 | 1470 | 400 | 181 |
| a23b19 | 111 | 114 | 314 | 199 | 53.5 |
| a23b20 | 111 | 115 | 478 | 155 | 38.0 |
| a18b19 | 24 | 114 | 223 | 101 | 25.1 |
| a18b29 | 24 | 116 | nt | 560 | 37.4 |
| a18b32 | 24 | 117 | nt | 411 | 89.1 |
| a25b19 | 118 | 114 | 165 | 37.6 | 8.14 |
| a26b19 | 119 | 114 | 158 | 32.8 | 5.28 |
| a18b39 | 24 | 120 | 305 | 289 | 38.8 |
| a18b42 | 24 | 121 | 409 | 204 | 39.5 |
| a18b49 | 24 | 31 | 46.9 | 38.9 | 6.98 |
| a18b50 | 24 | 123 | 154 | 44.1 | 8.76 |
| a18b51 | 24 | 124 | 80 | 35 | 5.01 | nt = not tested

Figure 3:
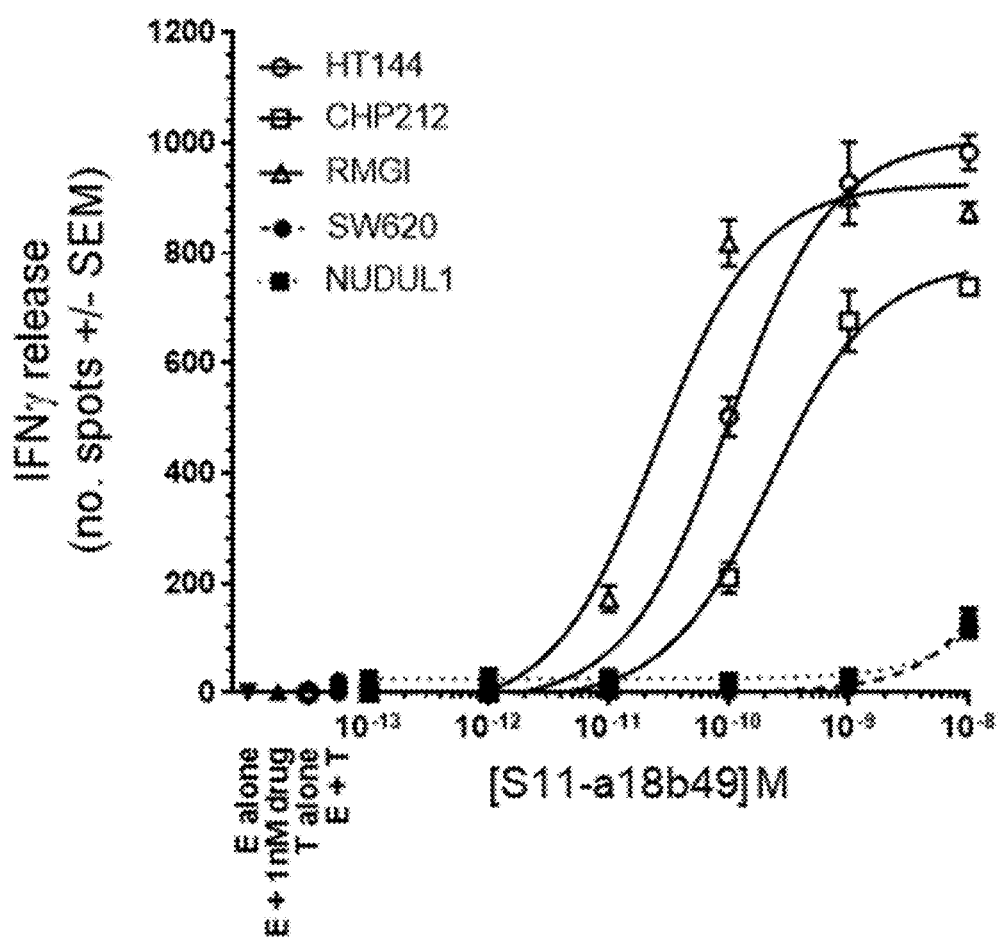
FIG. 3 is a series of line graphs showing T cell activation for selected mutated TCRs when fused to an anti-CD3 scFv, as described in Example 3.
Figure 3:
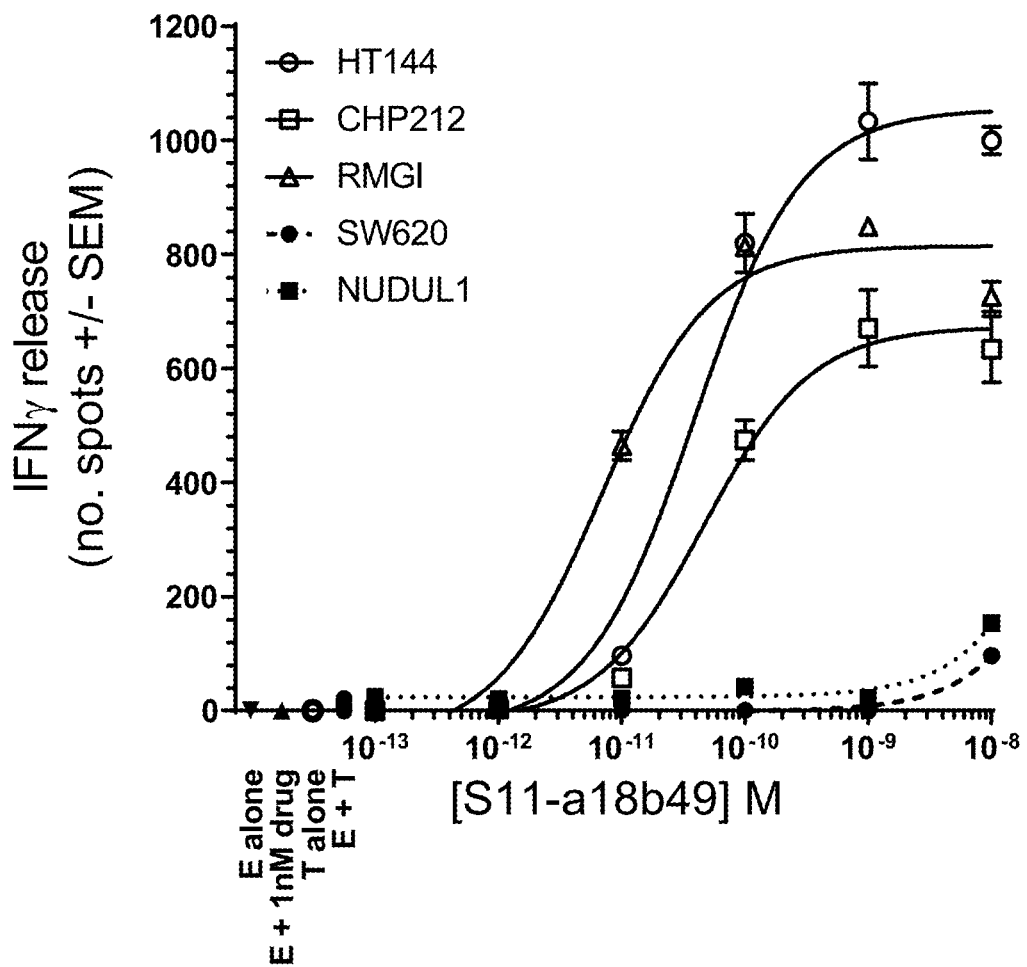
Figure 3:
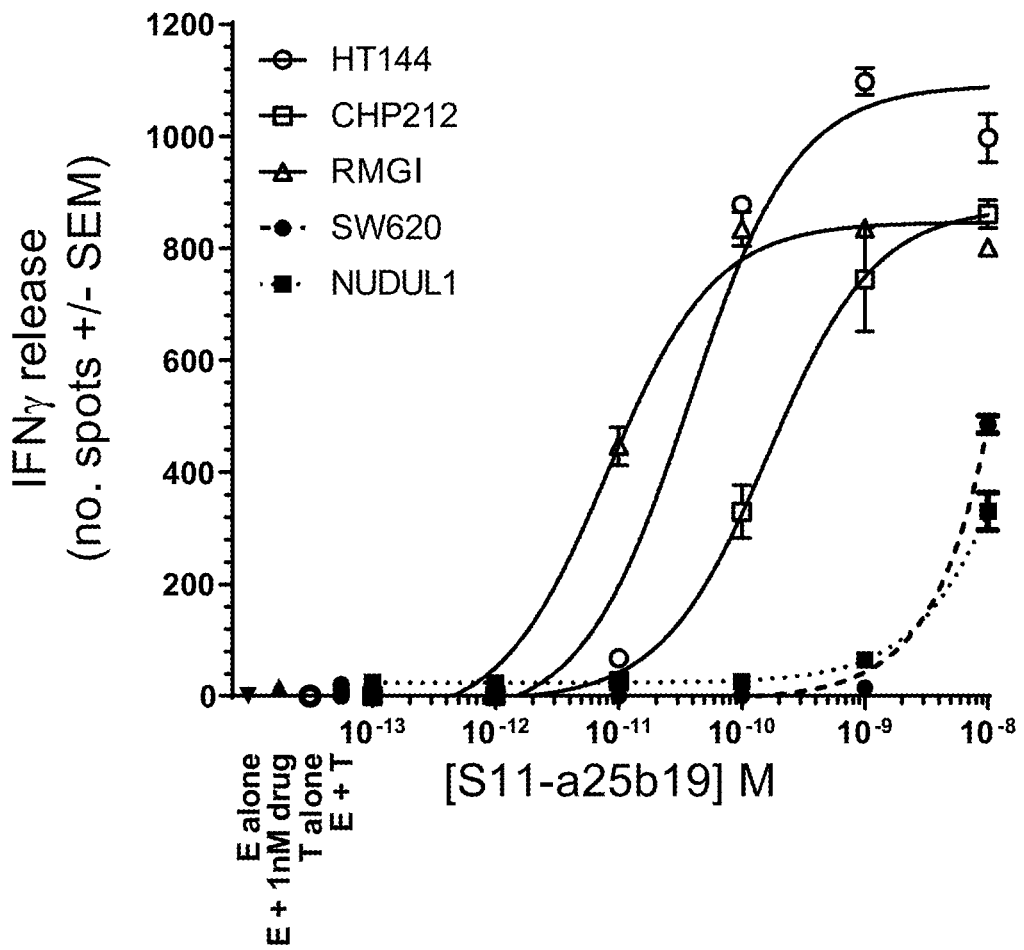
Figure 3:
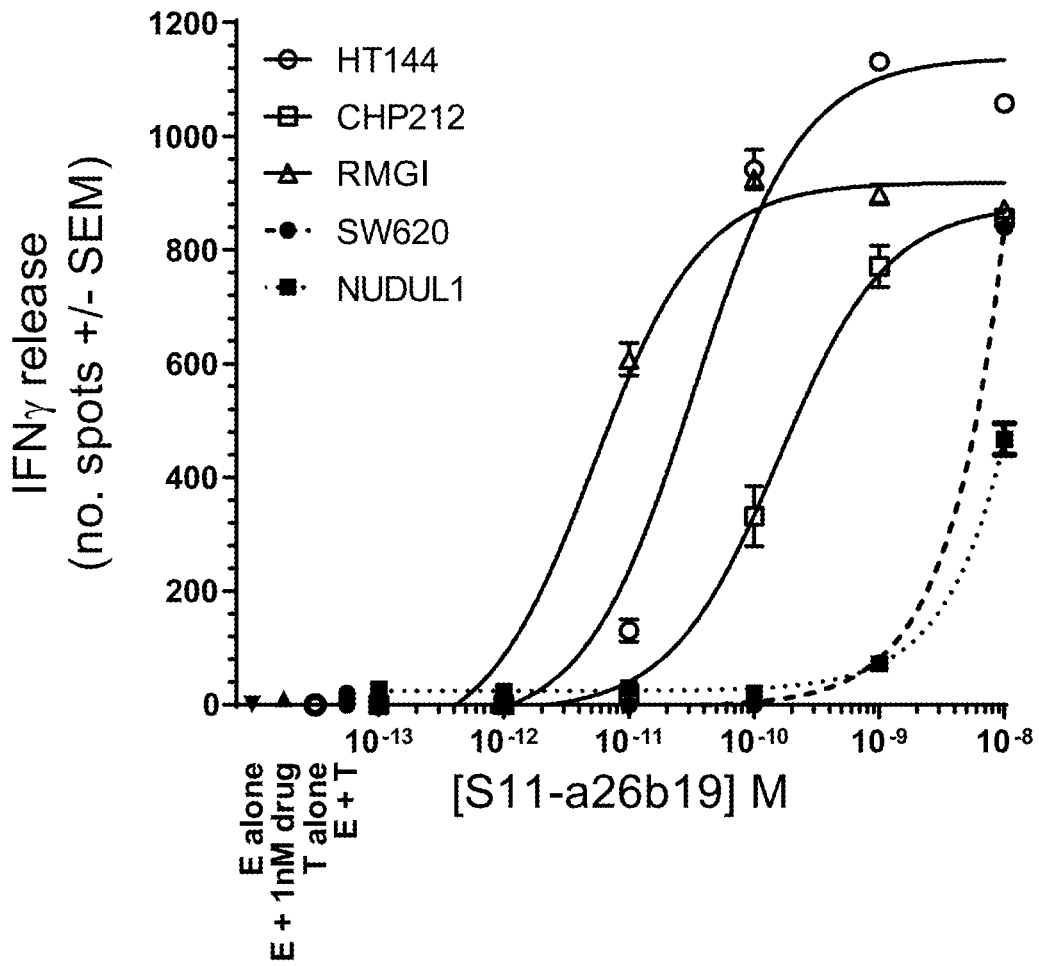

FIG. 3 shows graphical data for four exemplary TCR-anti-CD3 fusion molecules from the table above (a18b19; a18b49; a25b19; and a26b19). In each case T cell reactivity was observed against antigen positive cells in the low pM range. No detectable reactivity to antigen negative cells lines was observed at TCR-anti-CD3 fusion concentrations below 1 nM, indicating a wide therapeutic window between on target and non-specific binding. These data demonstrate that TCR-anti-CD3 fusion molecules can mediate potent redirection of T cell against antigen positive cells lines.

Example 4—TCR-Anti-CD3 Fusion Molecules Demonstrate a Wide Affinity Window Between Recognition of Target and Mimetic pHLA Complexes To further confirm the specificity of TCR-anti-CD3 fusion molecules, SPR was performed as described above to compare target binding with recognition against the four mimetic peptides identified above.

Figure 4:
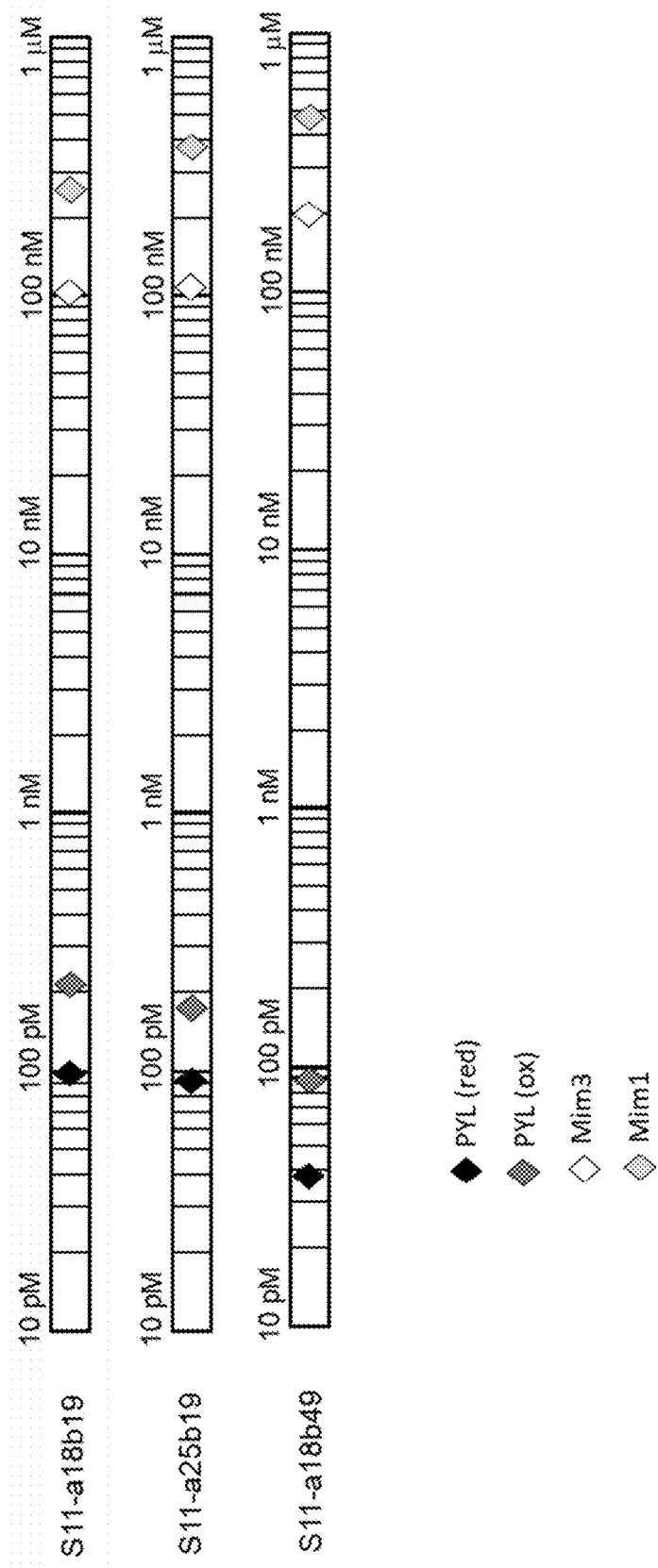
FIG. 4 shows the affinity window (difference in affinity between the target peptide complex and similar mimetic peptides) for selected mutated TCRs, as described in Example 4.

No binding was observed to Mim2 and Mim4. Binding to Mim1 and Mim3 was detected, however, the interactions were weak, especially compared to recognition of the target. The data are shown in the table below. FIG. 4 shows a graphical representation of the data.

| Molecule ID | PYL (red) $K_D$ (pM) | PYL (red) T½ (h) | PYL (ox) $K_D$ (pM) | PYL (ox) T½ (h) | Mim1 $K_D$ (nM) | Mim1 T½ (sec) | Mim3 $K_D$ (nM) | Mim3 T½ (sec) |
|---|---|---|---|---|---|---|---|---|
| a18b19 | 100 | 4 | 227 | 2.3 | 252 | 5 | 104 | 10 |
| a25b19 | 92 | 6.4 | 177 | 3.5 | 380 | 8 | 112 | 22 |
| a18b49 | 39 | 7.9 | 89 | 5.9 | 469 | 7 | 200 | 7 |

These data demonstrate that there is a wide affinity window between binding to target and binding to mimetics of at least 2-3 logs.

Example 5—TCR-Anti-CD3 Fusion Molecules do not Activate T Cells in the Presence Cells Derived from Normal Tissues at Concentrations within a Therapeutic Range To further determine their suitability for therapeutic use TCR-anti-CD3 fusion molecules were tested for non-specific activation in the presence of normal cells derived from healthy human tissues using the same ELISPOT methodology as described above. The panel of normal cells used in this example were derived from pulmonary, cardiac and muscle tissues: Pulmonary—bronchial epithelial cells (HBEpiC14); Muscle—skeletal muscle myoblasts (HS-KMM21); Cardiac—aortic endothelial cells (HAoEC3a); Pulmonary—fibroblasts (HPF18). HT144 and SW620 cells were used as target positive and target negative cell lines respectively.

Figure 5:
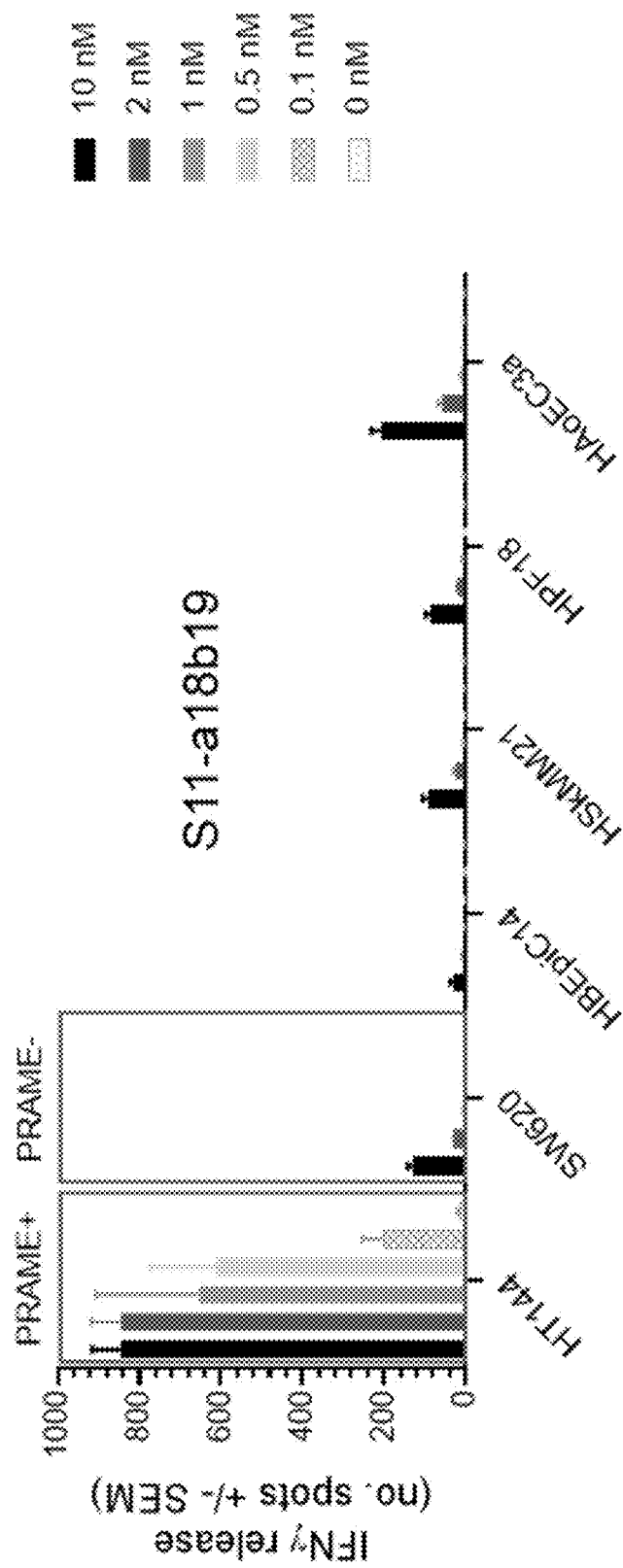
Figure 5:
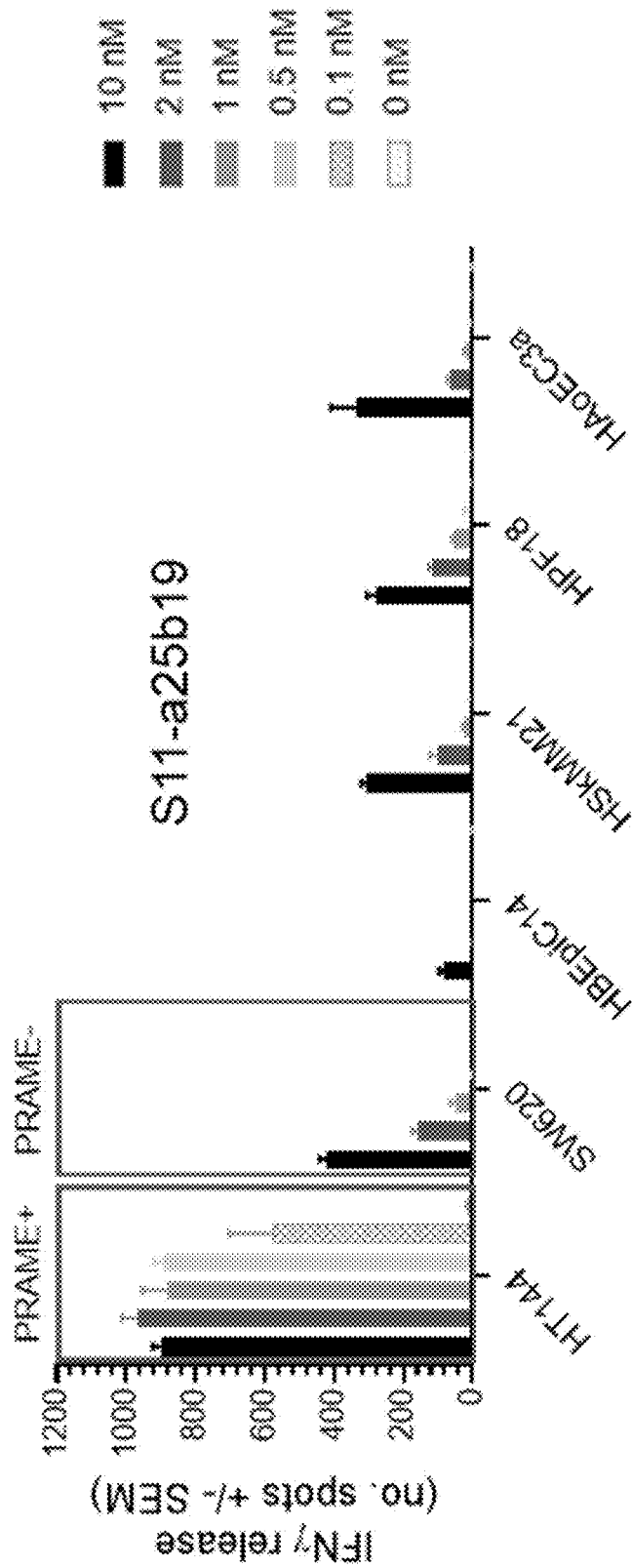
Figure 5:
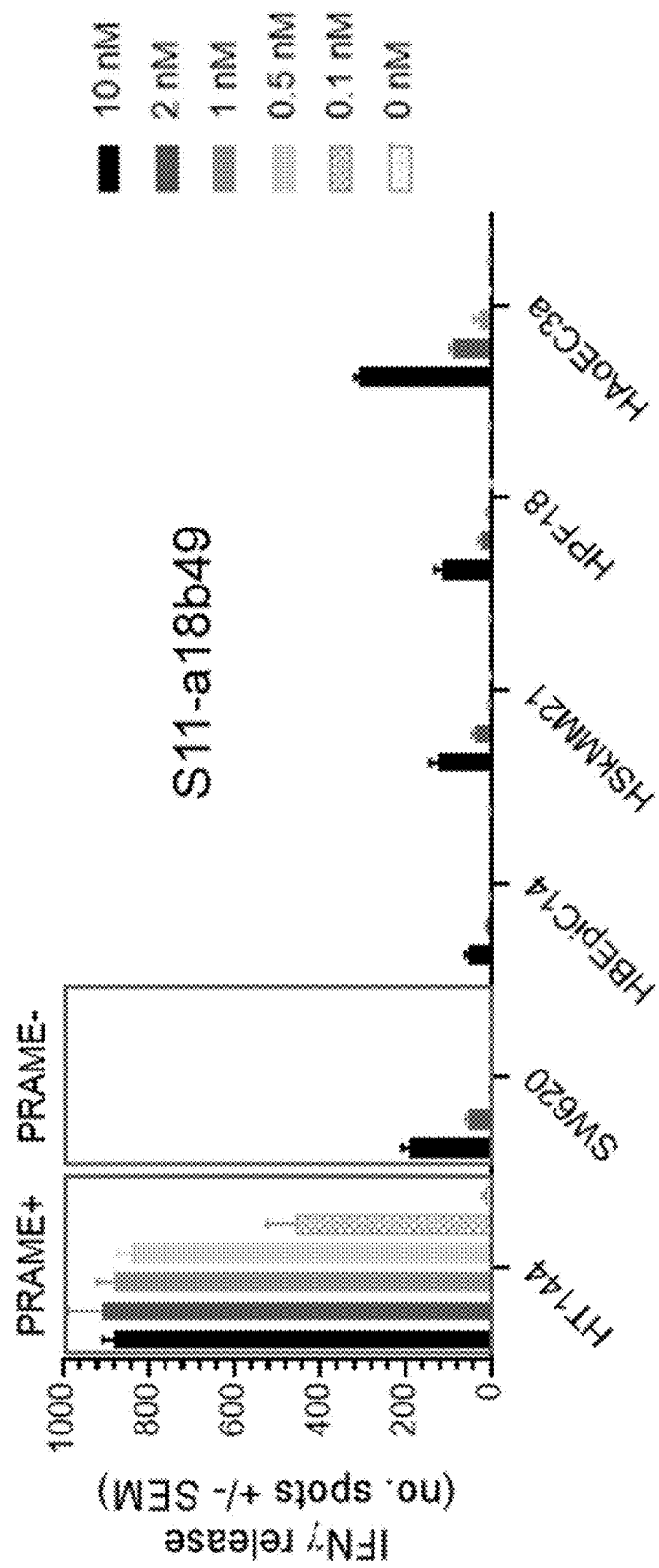

Results are shown in FIG. 5 for three TCR-anti-CD3 fusion molecules: a18b19, a25b19, a18b49. The data demonstrate that there is minimal reactivity against normal cells at concentrations below 1 nM. Further analysis indicated an approximate 200-fold window between the lowest concentration giving rise to reactivity against antigen positive cells (5 pM) and the lowest concentration were reactivity against normal cells is observed (1 nM).

Molecule a18b49 was selected for further optimisation.

Example 6—Further Amino Acid Substitutions Reduce Manufacturing Liabilities while Retaining Other Desirable Therapeutic Properties Additional amino acid substitutions were made in the TCR alpha and beta chain variable domain of a18 and b49 chains to improve manufacturability while maintaining affinity, potency and specificity of the corresponding TCR-anti-CD3 fusion molecule.

Firstly, five deamidation prone residues were identified based on sequence analysis; three in the alpha chain and two in the beta chain. Deamidation was abundant at four of five sites, and for four of five sites deamidation was shown to increase in abundance upon 2 weeks at +30° C., as shown in the table below.

| Location of deamidation | Fold deamidation (+30 C., 2 weeks) |
|---|---|
| Chain a18, N53 | >3.5 |
| Chain a18, N61 | minor |
| Chain a18, N99 | >6 |
| | (lower than 1% @ 2 weeks) |
| Chain b49, N51 | >1.9 |
| Chain b49, N98 | >2 |

To reduce deamidation risk, various amino acid substitutions were tested at each site and at flanking positions. It was found that incorporating V at position 54 and Q at position 61 of the alpha chain, and A at position 52 and I at position 98 of the beta chain (based on the numbering of a18 and b49) substantially reduced the presence of deamidation, while maintaining the other desirable characteristics.

Secondly, amino acid substitutions were identified that served to increase the thermal stability of the molecule as determined by differential scanning fluorimetry (DSF). Using DFS the melting temperature (Tm) of a18b49 was determined as =53.7° C. Five mutations were identified, one alpha chain mutation and four beta chain framework mutations were identified which increased the Tm: R98H in the alpha chain, based on numbering of a18, and T13K, L43P, I47F, F90I in the beta chain, based on the numbering of b49.

Molecules combining these mutations were prepared and tested

Binding

Binding to target was determined by SPR as described above at both 25° C. and 37° C.

Results shown in the table below demonstrate that the molecules retained pM affinity.

|  |  |  | PYL (red) 25° C. | | PYL (red) 37° C. | | |
|---|---|---|---|---|---|---|---|
| Molecule ID | TRAV (SEQ ID) | TRBV (SEQ ID) | $K_D$ (pM) | T½ (h) | $K_D$ (pM) | T½ (min) | Yield (mg/L) |
| a18b49 | 24 | 31 | 39 | 7.9 | 320 | 39 | 4.3 |
| a77b150 | 26 | 34 | 169 | 2.0 | 602 | 12 | 5.1 |
| a77b152 | 26 | 40 | 87 | 3.3 | 310 | 23 | 9.9 |
| a90b150 | 29 | 34 | 67 | 5.3 | 316 | 31 | 9.6 |
| a90b152 | 29 | 40 | 43 | 8.4 | 275 | 48 | 10.4 |

Potency—T Cell Activation

Potency was determined in cellular assays. In this example, the TCR-anti-CD3 fusion molecules comprise a variant antiCD3 sequence, termed U28, which has been described previously (WO 2020/157210) for molecules a77b150, a90b152. T cell activation was determined by IFNγ ELISPOT assays as described above. The following cancer cells lines were used as antigen positive target cells: HT144 (melanoma); RMGI (ovarian carcinoma) and SKNAS (neuroblastoma). In addition, the following antigen negative cell line was used: SW620 (colon adenoncarcinoma). Data were plotted using PRISM software and $EC_{50}$ values were calculated from the curves.

Figure 6:
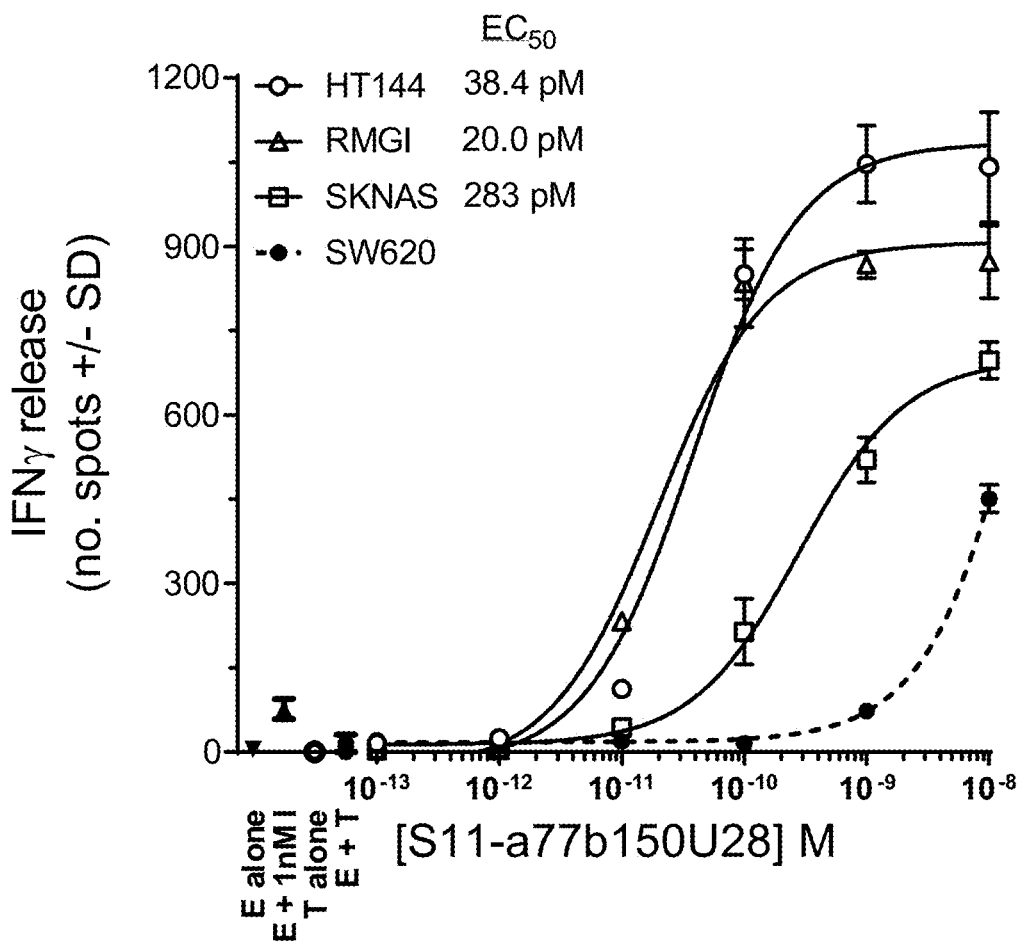
Figure 6:
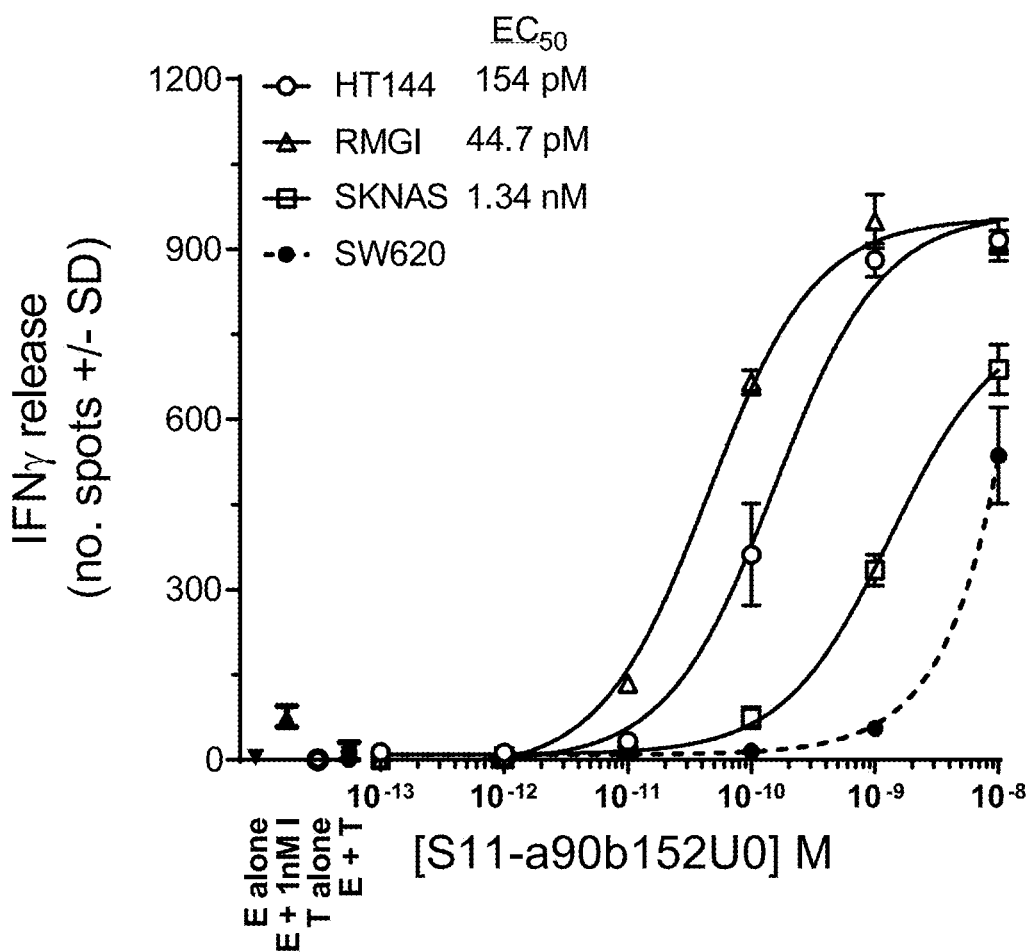
Figure 6:
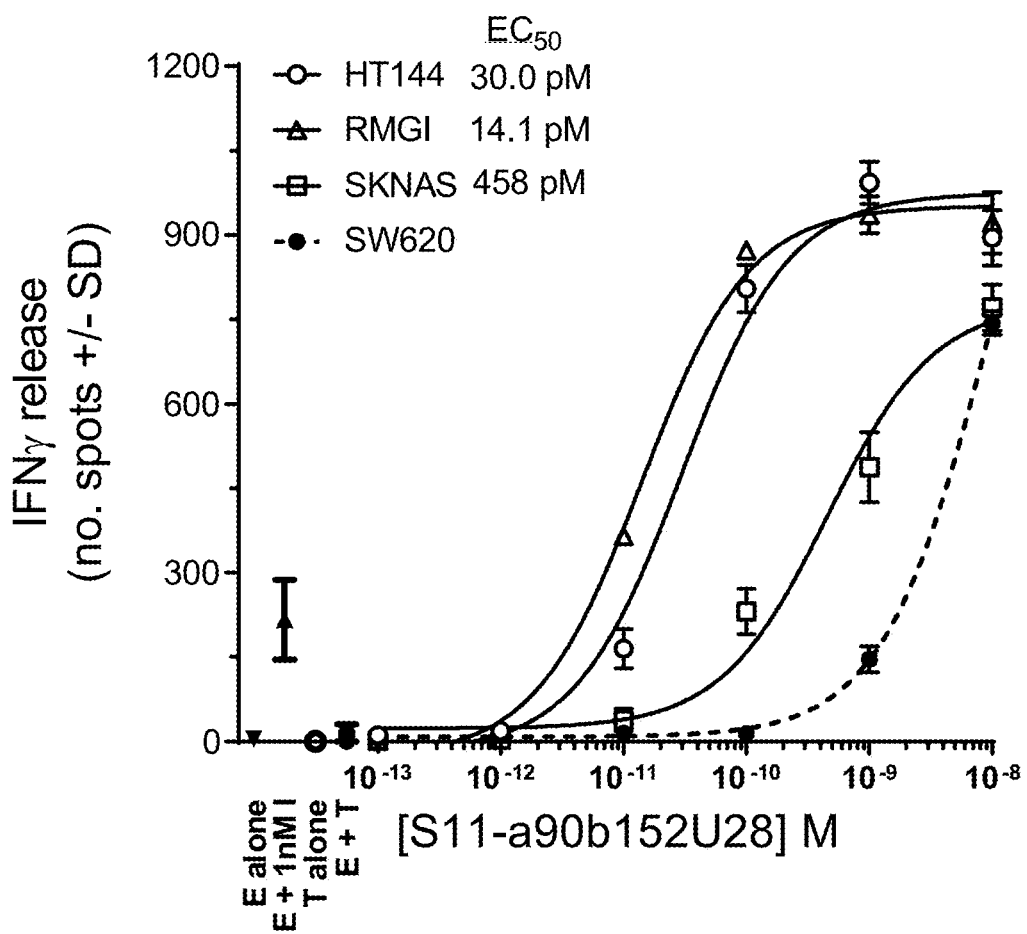

The resulting data are shown in FIG. 6.

Potency—Cell Killing

To determine the ability of the a77b150U28, a90b152U0, a90b152U28 to kill antigen positive cancer cells, a killing assay was performed using the xCelligence platform (Agilent) with appropriate 96 well plates for impedance reading (xCELLigence E-plate 96 PET part number 300600900). PBMCs were used as effector cells. Target cells were grown for 24h in E-plates, prior to addition of effector cells and test molecule. In this example HT144 (melanoma) and HEC-6 (endometrial adenocarcinoma) cells were used as target positive cancer cells. Cell lines were titrated to optimise the number of cells per wells to reach a cell index of approximately 1 after 24h in culture in E-plates HT144—10,000 cells/well; HEC6—5,000 cells/well. To avoid too rapid depletion of nutrient in media, effectors are plated at a different ratio depending on the target cell numbers (HT144, E:T ratio=5:1; HEC6 E:T ratio=10:1). The percentage of cytolysis was determined using the normalised Cell Index (impedance measurement) at various time points over 73 h. Does response curves were plotted using % cytolysis at 73 h. Ec50 values were calculated from were calculated from the curves and are shown in the table below.

|  | $EC_{50}$% cytolysis at 73 h (pM) | | |
|---|---|---|---|
| Cell line | a77b150U28 | a90b152U0 | a90b152U28 |
| HT144 | 16.9 | 22.5 | 10.2 |
| HEC6 | 3.93 | 5.97 | 1.37 |

These data demonstrate that the TCR-anti-CD3 fusion molecules mediate potent activation of T cells and killing of cancer cells, with Ec50 values in the low pM range.

Normal Cell Reactivity

Reactivity against normal cells was carried out as described above, with TCR-anti-CD3 fusion molecules a77b150U28, a90b152U0, a90b152U28. The table below shows the lowest concentration at which reactivity was observed against cells derived from normal tissues. Pulmonary—fibroblasts (HPF18); Muscle—skeletal muscle myoblasts (HSkMM21); Cardiac—aortic endothelial cells (HAoEC3a).

| Cell line | a77b150U28 | a90b152U0 | a90b152U28 |
|---|---|---|---|
| HPF18 | 1.11 nM | 3.33 nM | 1.11 nM |
| HSkMM21 | 3.33 nM | 3.33 nM | 1.11 nM |
| HAoEC3a | 1.11 nM | 1.11 nM | 0.37 nM |

No substantial reactivity was observed at concentrations below 1 nM.

Binding to Mimetic Peptides

TCR-anti-CD3 fusion molecule a90b152U28 was assessed for binding to mimetic peptides using SPR as described above at both 25° C. and 37° C.

| | 25° C. | |
|---|---|---|
| Peptide | $K_D$ (nM) | T ½ (sec) |
| Mim1 (PLEC) | 59 | 16 |
| Mim3 (PLCB4) | 157 | 12 |
| Mim2 (SYNRG) | nb | — |
| Mim4 (LSM14B) | nb | — | nb = no detectable binding

Again, no binding was observed to peptides Mim2 and Mim4. Binding to mim 1 and Mim3 was in the nM range. Therefore, a wide affinity window is maintained between the target and mimetic peptides.

Serum Stability

TCR-anti-CD3 fusion molecules were diluted in human serum (10 µg/ml) and incubated at 37° C. for up to 168 hours. The presence of high and low molecular weight species (HMW/LMW), as well as % monomer was determined by SEC UPLC. The data are provided in the table below.

| Molecule ID | % Total HMW | % Monomer | % Total LMW | Increase HMW |
|---|---|---|---|---|
| a77b150U28 Control | 0.4 | 98.3 | 1.2 | — |
| a77b150U28 +37 C. | 16.9 | 83.0 | 0.3 | 16.5 |
| a90b152U28 Control | 0.2 | 99.8 | 0 | — |
| a90b152U28 +37 C. | 6.1 | 93.9 | 0.03 | 5.9 |

These data show a77b150U28 and a90b152U28 have acceptable stability in human serum.

In total these data confirm that TCR-anti-CD3 fusion molecules of the invention have desirable therapeutic properties.

Example 7—Structural Analysis of TCR-pHLA Binding

Structural analysis of the S11 TCR bound to the PYLGQMINL (SEQ ID NO: 1) HLA-A24 complex was performed using x-ray crystallography. Unique structural features that confer potency and specificity were identified.

Methods

X-ray crystallography. Crystals were grown by vapor diffusion via the sitting drop technique using the MRC 2-well crystallisation plates. 150 nL of 10 to 15 mg/mL TCR-pHLA complex (mixed at a 1:1.1 molar ratio) was added to 150 nL of reservoir solution using the Gryphon dispensing robot (Art Robbins). The plates were then incubated at 20° C. and imaged using ROCK IMAGER 1000 (Formulatrix). Crystals selected for further analysis were cryoprotected with 30% ethylene glycol and then flash-cooled in liquid nitrogen. Diffraction data were collected at several different beamlines at the Diamond Light Source (Didcot, UK) and processed through xia2 DIALS (Winter (2010). J Appl Crystallogr. 43, 186-190, Winter et al. (2018). Acta Crystallogr Sect D Struct Biology. 74, 85-97) or xia2 3dii (Kabsch (2010). Acta Crystallogr Sect D Biological Crystallogr. 66, 125-132) or autoPROC (Vonrhein et al. (2011). Acta Crystallogr Sect D Biological Crystallogr. 67, 293-302) automated pipelines. TCR-pHLA complex structures were solved by molecular replacement using Phaser (McCoy et al. (2007). J. Appl. Crystallogr. 40, 658-674), models built using Coot (Emsley et al. (2010). Acta Crystallogr Sect D Biological Crystallogr. 66, 486-501), and refined using refmac (Kovalevskiy et al. (2018). Acta Crystallogr. Sect. D, Struct. Biol. 74, 215-227), all within the CCP4 suite (Agirre et al. (2023). Acta Crystallogr. Sect. D, Struct. Biol. 79, 449-461). Molecular replacement search models were identified as follows: for the different TCR molecules, the PDB was searched for structures of proteins with high sequence similarity to alpha and beta sequences separately and these were used as models. For HLA-A2-B2m, the PDB 6RPA (TCR removed) was used. For computational modelling of TCR referred to herein as "a90b152", Molecular Operating Environment (MOE) package (version 2022.02, Chemical Computing Group ULC, Canada) was used with "S11" TCR as template and refined using QuickPrep.

TCR docking geometry angle calculations: The calculation of the following angles was adopted from Rudolph et al. (2006). Annu Rev Immunol. 24, 419-466.
 a. Crossing angle. This angle was calculated by generating two vectors: an HLA groove vector and a TCR cystine vector (or "TCR interdomain vector"). The HLA groove vector follows the two parallel HLA helices with the direction N-terminus to C-terminus of HLA helix 1 and passing through the HLA centroid. The TCR cystine vector (or "TCR interdomain vector") connects the characteristic cystines (i.e., the intrachain disulfide bonds) in the two variable regions and points from the intrachain disulfide bond in the alpha chain variable region to the intrachain disulfide bond in the beta chain variable region. The crossing angle was defined by the angle between the TCR cystine vector and the HLA groove vector.
 b. Tilt angle. The TCR symmetry vector represents the pseudo-two-fold symmetry axis of the TCR variable subunits and points in direction of its CDRs and passes through the TCR centroid. The tilt angle was calculated between the TCR symmetry axis and the HLA groove vector.
 c. Roll angle. A second HLA vector (HLA v2) was generated perpendicular to the HLA groove vector and points from HLA helix 1 to HLA helix 2. The two vectors meet at the centroid of the HLA helices. The roll angle was calculated between HLA v2 and the TCR symmetry vector.

Interaction analysis. Residues between TCR and pHLA were identified to be in contact if the distance measurement between any atom from a TCR residue was within or equal to 4.1 Å to any atom from a peptide or an HLA residue.
Results
The crystal structure showed that S11 bound to its cognate pHLA (i.e., a PYLGQMINL (SEQ ID NO: 1) HLA-A24 complex) with a crossing angle of approximately 43 degrees. Four of the six CDRs (αCDR3, βCDR1, βCDR2 and βCDR3) directly interacted with the PYLGQMINL (SEQ ID NO:1) peptide and made contacts peptide residues between positions 1 to 8. The TCR beta chain, especially CDR3β, dominated the interaction between the TCR and the peptide. The following tables provide a summary of buried surface area and binding geometry calculations for the interaction between the S11 TCR and PYLGQMINL (SEQ ID NO: 1) HLA-A24 complex.

| Buried surface area | | | | |
|---|---|---|---|---|
| Chains | TCR on peptide | TCR on HLA | TCR on HLA helix 1 | TCR on HLA helix 2 |
| Alpha chain (%) | 38.4% | 49.5% | 41.1% | 59.5% |
| Beta chain (%) | 61.6% | 50.5% | 58.9% | 40.5% |
| Total BSA (Å²) | 400 | 943.9 | 499.7 | 457.3 |

| Binding geometry angles | | |
|---|---|---|
| Crossing | Tilt | Roll |
| 42.9 | 3.9 | −1.2 |

Identification of Peptide and TCR CDR Residues Critical for Binding

Figure 8:
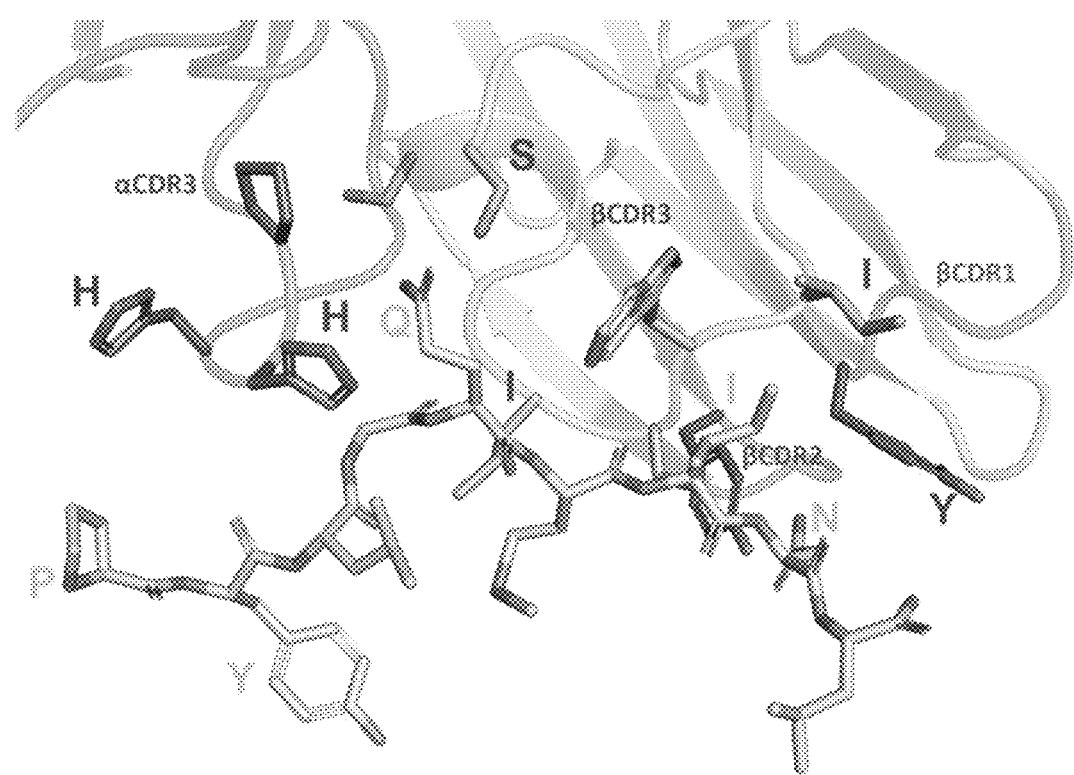

The crystal structure of the S11 TCR bound to PYLGQMINL (SEQ ID NO: 1) in complex with HLA-A24 was further analyzed to identify critical residues within the interface between the peptide and the TCR CDRs. As can be seen in the crystal structure represented in FIG. 7, peptide positions P1, Q5, I7 and N8 of PYLGQMINL (SEQ ID NO: 1) formed the key antigenic contact points on the peptide, with the residues at these positions having exposed side chains facing the TCR interface. High affinity variants of the S11 TCR, as described in Examples 1-6, have enhanced contacts to these four exposed peptide positions, resulting from inclusion of bulkier residues within the TCR CDRs. For example, the TCR variant referred to herein as "a90b152" includes bulkier residues at key CDR positions near the peptide (i.e. R98H and R97H in aCDR3, A103S, S98I and V95I in bCDR3, and L30Y in bCDR1) and has an affinity for pHLA complex in the low pM range. The interface between the a90b152 and the PYLGQMINL (SEQ ID NO: 1) peptide was computationally modelled based on the TCR crystal structure of S11 and is shown in FIG. 8.

The CDR residues of S11 TCR critical for binding to the PYLGQMINL (SEQ ID NO: 1) peptide were also determined from the crystal structure based on proximity between the residues. The following table indicates these residues in bold and double underlined text:

| CDR1α | CDR2α | CDR3α | CDR1β | CDR2β | CDR3β |
|---|---|---|---|---|---|
| SSY SPS | YTSA ATLV | VVSAPNR DDKII | SGDLS | YYN GEE | ASSVWSSG GASAGELF |

To demonstrate that high affinity TCR variants as described in examples 1-6 maintain the same or similar peptide contacts as the S11 TCR, the peptide-contacting CDR residues of the TCR variant a90b152 were determined by computational modelling, using the crystal structure of the S11 TCR bound to PYLGQMINL (SEQ ID NO: 1) in complex with HLA-A24 as a template. The CDR positions of a90b152 that were critical for binding to the PYLGQMINL (SEQ ID NO: 1) peptide were similar to the S11 TCR and are shown in the table below.

| CDR1α | CDR2α | CDR3α | CDR1β | CDR2β | CDR3β |
|---|---|---|---|---|---|
| SSY SPS | YIGN VTLV | VVGAPHH NDKII | SGD YS | YYN AEE | ASSIWSIGG ASSGNLSF |

Comparison of S11 TCR Structure with Alternative Scaffold TCRs

Additional crystal structures were obtained for TCRs derived from different native TCRs and were used to compare the close contact points and interaction profile to that of S11 TCR. As shown in the table below, direct contacts between S11 TCR and PYLGQMINL (SEQ ID NO: 1)-peptide resulted in the the greatest number of peptide contacts (8 residues), with none of the other TCRs having contacts to more than 6 peptide residues. Furthermore, only S11 TCR demonstrated contacts with the exposed proline residue at position 1 of the peptide. These data indicate that binding geometry appears to be vital for generating a maximum interface with peptide resulting in a highly specific interaction.

The following table provides a comparison of S11 TCR binding geometry with alternative TCRs

| TCR | Peptide contacts (bold) | Crossing angle (°) | Tilt angle (°) | Roll angle (°) | BSA on peptide (Å²) |
|---|---|---|---|---|---|
| S11 | PYLGQMINL | 42.9 | 3.9 | −1.2 | 400 |
| S6 | PYLGQMINL | 351.4 | 7.3 | −33.4 | 221 |
| S7 | PYLGQMINL | 46.8 | −19.9 | −6.2 | 269.6 |
| S8 | PYLGQMINL | 57.4 | −24.6 | −4.8 | 297.7 |
| S9 | PYLGQMINL | 11.4 | 6.3 | 7.2 | 333.5 |
| S10 | PYLGQMINL | 11.5 | 7 | 9.1 | 297.8 |

The invention claimed is:

1. A binding molecule comprising a TCR alpha chain variable domain and a TCR beta chain variable domain, wherein the binding molecule has the property of binding to PYLGQMINL (SEQ ID NO: 1) in complex with HLA-A24, wherein each of the alpha chain variable domain and the beta chain variable domain comprises FR1-CDR1-FR2-CDR2-FR3-CDR3-FR4, where FR is a framework region and CDR is a complementarity determining region, wherein (a) the alpha chain CDRs have the following sequences:

```
CDR1
                                        (SEQ ID NO: 5)
SSYSPS,

CDR2
                                       (SEQ ID NO: 27)
YIGNVTLV,

CDR3
                                       (SEQ ID NO: 30)
VVGAPHHNDKII,
``` and (b) the beta chain CDRs have the following sequences:

```
CDR1
                                       (SEQ ID NO: 32)
SGDYS

CDR2
                                       (SEQ ID NO: 35)
YYNAEE

CDR3
                                       (SEQ ID NO: 41)
ASSIWSIGGASSGNLS.
```

2. The binding molecule of claim 1, wherein the alpha chain variable domain framework regions comprise the following sequences:
FR1 —AQSVTQLDSHVSVSEGTPVLLRCNYS (SEQ ID NO: 8), optionally with one, two or three mutations therein,
FR2 —LFWYVQHPNKGLQLLLK (SEQ ID NO: 9), optionally with one, two or three mutations therein,
FR3 —KGINGFEAEFKKSETSFHLTKPSAHMS-DAAEYFC (SEQ ID NO: 10), optionally with one, two or three mutations therein,
FR4 —FGKGTRLHILP (SEQ ID NO: 11), optionally with one, two or three mutations therein,
and/or
the beta chain variable domain framework regions comprise the following sequences:
FR1 —DSGVTQTPKHLITATGQRVTLRCSPR (SEQ ID NO: 18), optionally with one, two or three mutations therein,
FR2 —VYWYQQSLDQGLQFLIQ (SEQ ID NO: 19), optionally with one, two or three mutations therein,
FR3 —RAKGNILERFSAQQFPDLHSELNLSSLEL-GDSALYFC (SEQ ID NO: 20), optionally with one, two or three mutations therein,
FR4 —FGEGSRLTVL (SEQ ID NO: 21), optionally with one, two or three mutations therein.

3. The binding molecule of claim 2, wherein the alpha chain variable domain framework regions comprise a N61Q mutation, numbered according to SEQ ID NO: 3.

4. The binding molecule of claim 2, wherein the beta chain variable domain framework regions comprise one or more of the following mutations T13K, L43P, I47F, L61P and F90I, numbered according to SEQ ID NO: 13.

5. The binding molecule of claim 1, wherein the alpha chain variable domain comprises the amino acid sequence provided in SEQ ID NO: 29 and the beta chain variable domain comprises the amino acid sequence provided in SEQ ID NO: 40.

6. The binding molecule of claim 1, which comprises the extracellular region of a TCR alpha chain constant domain, optionally truncated at the C terminus by up to 15 amino acids, and/or the extracellular region of a TCR beta chain constant domain, optionally truncated at the C terminus by up to 15 amino acids.

7. The binding molecule of claim 6, wherein a non-native covalent disulphide bond links a residue of the TCR alpha chain constant domain to a residue of the TCR beta chain constant domain.

8. The binding molecule of claim 6, wherein
the extracellular region of the TCR alpha chain constant domain comprises the amino acid sequence provided in SEQ ID NO: 4, and/or
the extracellular region of the TCR beta chain constant domain comprises the amino acid sequence provided in SEQ ID NO: 48.

9. The binding molecule of claim 1 any one of the preceding claims, which is in single chain format of the type Vα-L-Vβ, Vβ-L-Vα, Vα-Cα-L-Vβ, or Vα-L-Vβ-Cβ, wherein Vα and Vβ are TCR α and β variable regions respectively, Cα and Cβ are TCR α and β constant regions respectively, and L is a linker sequence.

10. The binding molecule of claim 1, which comprises two or more polypeptide chains, wherein the TCR alpha chain variable domain and the TCR beta chain variable domain are comprised in separate polypeptide chains.

11. The binding molecule of claim 1, comprising
a TCR alpha chain comprising the amino acid sequence of SEQ ID NO: 49 and a TCR beta chain comprising the amino acid sequence of SEQ ID NO: 50.

12. The binding molecule of claim 1 optionally wherein the binding molecule is bispecific.

13. The binding molecule of claim 12, comprising an antigen-binding moiety that comprises a heavy chain variable region (VH) and an antibody light chain variable region (VL), wherein the antigen-binding moiety is capable of binding to a CD3 antigen.

14. The binding molecule of claim 13, wherein the binding molecule comprises a single chain variable fragment (scFv) comprising the VH and the VL.

15. The binding molecule of claim 13, wherein
(a) the VH comprises CDRs having the following sequences:

```
CDR1
                                      (SEQ ID NO: 56)
GYSFTGYT
or (SEQ ID NO: 62)
GYSFTGYA;

CDR2
                                      (SEQ ID NO: 57)
INPYKGVS;
and

CDR3
                                      (SEQ ID NO: 58)
ARSGYYGDSDWYFDV,
``` and
(b) the VL comprises CDRs having the following sequences:

```
CDR1
                                      (SEQ ID NO: 52)
QDIRNY;

CDR2
YTS;
and

CDR3
                                      (SEQ ID NO: 54)
QQGNTLPWT.
```

16. The binding molecule of claim 13, wherein the VH or VL is covalently linked to the C- or N-terminus of the TCR alpha chain or TCR beta chain, optionally via a linker sequence.

17. The binding molecule of claim 16, wherein the VH or VL is covalently linked to the C- or N-terminus of the TCR alpha chain or TCR beta chain via a linker sequence selected from GGGGS (SEQ ID NO: 64), GGGSG (SEQ ID NO: 70), GGSGG (SEQ ID NO: 71), GSGGG (SEQ ID NO: 72), GSGGGP (SEQ ID NO: 73), GGEPS (SEQ ID NO: 74), GGEGGGP (SEQ ID NO: 75), GGEGGGSEGGGS (SEQ ID NO: 76), GGGSGGGG (SEQ ID NO: 77), GGGGSGGGGSGGGGSGGGGSGGGS (SEQ ID NO: 59), GGGGSGGGGSGGGGSGGGGS (SEQ ID NO: 78), EAAAK (SEQ ID NO: 79) and EAAAKEAAAKEAAAK (SEQ ID NO: 80).

18. The binding molecule of claim 16, wherein the C-terminus of the VH is covalently linked to the N-terminus of the TCR beta chain, optionally via a linker comprising the amino acid sequence provided in SEQ ID NO: 64.

19. The binding molecule of claim 18, comprising an alpha chain amino acid sequence as set forth in SEQ ID NO: 49 and a beta chain-anti-CD3 fusion sequence as set forth in SEQ ID NO: 69.

20. The binding molecule of claim 13, comprising
a first polypeptide chain which comprises the TCR alpha chain variable domain and the antibody VH or VL; and
a second polypeptide chain which comprises the TCR beta chain variable domain and the other of the antibody VH and VL,
wherein the respective polypeptide chains associate such that the binding molecule is capable of simultaneously binding the PYLGQMINL (SEQ ID NO: 1) HLA-A24 complex and the antigen of the antibody.

21. The binding molecule of claim 1, comprising an Fc domain.

22. A pharmaceutical composition comprising the binding molecule of claim 1, together with one or more pharmaceutically acceptable carriers or excipients.

* * * * *

UNITED STATES PATENT AND TRADEMARK OFFICE
CERTIFICATE OF CORRECTION

PATENT NO. : 12,134,647 B2
APPLICATION NO. : 18/405910
DATED : November 5, 2024
INVENTOR(S) : Jakub Jaworski et al.

Page 1 of 1

It is certified that error appears in the above-identified patent and that said Letters Patent is hereby corrected as shown below:

In the Claims

Column 106 Line 43 (Claim 8): "and/or" should be replaced with --and--.

Column 106 Lines 47-48 (Claim 9): "any one of the preceding claims" should be deleted.

Signed and Sealed this
Twenty-eighth Day of January, 2025

Coke Morgan Stewart
*Acting Director of the United States Patent and Trademark Office*